(12) United States Patent
McCall et al.

(10) Patent No.: US 9,370,522 B2
(45) Date of Patent: Jun. 21, 2016

(54) HETEROCYCLIC COMPOUNDS FOR THE INHIBITION OF PASK

(71) Applicant: BioEnergenix, LLC, San Francisco, CA (US)

(72) Inventors: John M. McCall, Boca Grande, FL (US); Donna L. Romero, Chesterfield, MO (US); Michael Clare, Skokie, IL (US)

(73) Assignee: BioEnergenix, LLC, San Francisco, CA (US)

( * ) Notice: Subject to any disclaimer, the term of this patent is extended or adjusted under 35 U.S.C. 154(b) by 0 days.

(21) Appl. No.: 14/604,802

(22) Filed: Jan. 26, 2015

(65) Prior Publication Data

US 2015/0141422 A1        May 21, 2015

Related U.S. Application Data

(62) Division of application No. 12/727,231, filed on Mar. 19, 2010, now abandoned.

(60) Provisional application No. 61/299,192, filed on Jan. 28, 2010, provisional application No. 61/161,436, filed on Mar. 19, 2009.

(51) Int. Cl.
| | |
|---|---|
| *C07D 241/44* | (2006.01) |
| *A61K 31/5377* | (2006.01) |
| *C07D 241/42* | (2006.01) |
| *A61K 31/47* | (2006.01) |
| *A61K 31/498* | (2006.01) |
| *C07D 405/14* | (2006.01) |
| *C07D 401/04* | (2006.01) |
| *C07D 405/04* | (2006.01) |
| *C07D 409/04* | (2006.01) |

(52) U.S. Cl.
CPC ............ *A61K 31/5377* (2013.01); *A61K 31/47* (2013.01); *A61K 31/498* (2013.01); *C07D 241/42* (2013.01); *C07D 241/44* (2013.01); *C07D 401/04* (2013.01); *C07D 405/04* (2013.01); *C07D 405/14* (2013.01); *C07D 409/04* (2013.01)

(58) Field of Classification Search
CPC .................................................... C07D 241/44
See application file for complete search history.

(56) References Cited

U.S. PATENT DOCUMENTS

2003/0059917 A1    3/2003    McKnight et al.

FOREIGN PATENT DOCUMENTS

| WO | WO2007146747 | 12/2007 |
|---|---|---|
| WO | 2008148867 A2 | 12/2008 |
| WO | 2011028947 A2 | 3/2011 |

OTHER PUBLICATIONS

Lundholt, BK, Identification of Akt Pathway Inhibitors Using Redistribution Screening on the FLIPR and the IN Cell 3000 Analyzer, Journal of Biomolecular Screening, 2005, 20-29.

Hui, X, Synthesis and antiprotozoal activity of some new synthetic substituted quinoxalines, Bioorganic & Medicinal Chemistry Letters 16 (2006) 815-820.

Sanchez Maya, AB, New naphthylcombretastatins. Modifications on the ethylene bridge, Bioorganic & Medicinal Chemistry 13 (2005) 2097-2107.

Rong, F, Structure-activity relationship (SAR) studies of quinoxalines as novel HCV NS5B RNA-dependent RNA polymerase inhibitors, Bioorganic & Medicinal Chemistry Letters 17 (2007) 1663-1666.

*Primary Examiner* — Brian McDowell
(74) *Attorney, Agent, or Firm* — Dennis A. Bennett; Brock Levin

(57) ABSTRACT

Disclosed herein are new heterocyclic compounds having structural Formula IIa

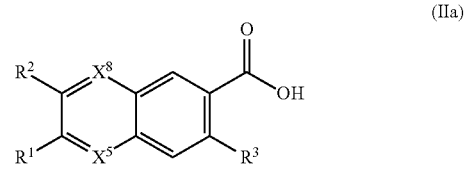

(IIa)

and compositions and their application as pharmaceuticals for the treatment of disease. Methods of inhibiting PAS Kinase (PASK) activity in a human or animal subject are also provided for the treatment of diseases such as diabetes mellitus.

1 Claim, No Drawings

HETEROCYCLIC COMPOUNDS FOR THE INHIBITION OF PASK

This application claims the benefit of priority of U.S. patent application Ser. No. 12/727,231, filed Mar. 19, 2010, which itself claims priority to U.S. Provisional Applications No. 61/161,436, filed Mar. 19, 2009, and No. 61/299,192, filed Jan. 28, 2010, the disclosures of which are hereby incorporated by reference as if written herein in their entireties.

Disclosed herein are new heterocyclic compounds and compositions and their application as pharmaceuticals for the treatment of disease. Methods of inhibiting PAS Kinase (PASK) activity in a human or animal subject are also provided for the treatment of diseases such as diabetes mellitus.

The regulation of glycogen metabolism is critical for the maintenance of glucose and energy homeostasis in mammals. Glycogen, a large branched polymer of glucose, acts as a reserve of carbon and energy in a variety of organisms. In mammals, the most important stores are found in the liver and skeletal muscle (1). Liver glycogen is required to efficiently buffer blood glucose levels during fasting, whereas muscle glycogen is primarily used locally as a fuel for muscle contraction (2). Dysregulation of glycogen metabolism has been implicated in the development of many diseases, including type 2 diabetes mellitus (3, 4).

The synthesis of glycogen is primarily controlled through regulation of the enzyme glycogen synthase (GYS, various isoforms), which catalyzes bulk glycogen synthesis (5, 6, 7). The muscle isoform of glycogen synthase (GYS1) is inactivated by reversible phosphorylation that occurs at nine distinct sites within the enzyme (8, 9, 10). In the best characterized form of glycogen synthase, the phosphorylation sites are clustered at the N and C termini (14). Glycogen synthase kinase-3 (GSK-3), an insulin-dependent kinase which has long been implicated in the stepwise phosphorylation of four key sites in the C terminus of glycogen synthase including Ser-640 (one of the most important endogenous regulatory phosphorylation sites in mammalian glycogen synthase (15, 32) and Ser-644 (10, 11-13, 24, 25). GSK-3, however, is not the sole kinase that phosphorylates C-terminal regulatory sites; GSK-3-independent mechanisms also exist, since serine-to-alanine substitutions at Ser-7 and Ser-10 block GSK-3-mediated phosphorylation of the important regulatory sites Ser-640 and Ser-644, and phosphorylation at these sites still occurs.

PASK (purine-analog sensitive kinase, PAS kinase) is a PAS domain-containing serine/threonine kinase, and genetic experiments in *S. cerevisiae* yeast have implicated PASK as a physiological regulator of glycogen synthase and glycogen accumulation (16, 17). As with the entire glycogen synthase regulatory system, PASK is highly conserved from yeast to man. Human PASK (hPASK) phosphorylates glycogen synthase primarily at Ser-640, causing near complete inactivation. It is interesting to note that the exact site of PASK-dependent phosphorylation is similar but not identical in yeast and mammalian glycogen synthase (18, 19); yeast PASK phosphorylates glycogen synthase at the site analogous to Ser-644, four residues C-terminal (18). It appears that the hPASK mid region (residues 444-955) is required for efficient phosphorylation of glycogen synthase in vitro and for interaction with glycogen synthase in cells: an hPASK mutant (Δ955) lacking the noncatalytic N terminus was unable to efficiently phosphorylate glycogen synthase. Since this region is not required for the phosphorylation of generic, nonphysiological substrates, such as histones and synthetic peptides, it has been proposed that the mid region of hPASK is essential for substrate-targeting. A similar substrate region has been discovered in many protein kinases (26-29). Unlike GSK-3, the activity of hPASK has been shown to be independent of insulin and probably regulated instead by a more direct metabolic signal (23).

Genetic and proteomic screens using yeast PASK identified a number of substrates and implicated this kinase in the regulation of carbohydrate metabolism and translation (18). It has previously been shown that yeast PASK phosphorylates glycogen synthase in vitro and that strains lacking the PASK genes (PSK1 and PSK2) had elevated glycogen synthase activity and an approximately 5- to 10-fold accumulation of glycogen relative to wild-type strains, consistent with impaired ability to phosphorylate glycogen synthase in vivo (18). Because glycogen synthesis and translation are two processes tightly regulated in response to nutrient availability and because PAS domains are frequently involved in metabolic sensing, a role for PASK in the cellular response to metabolic status has been proposed. Indeed, it was recently demonstrated that mammalian PASK plays a role in the cellular response to nutrients. The catalytic activity of PASK in pancreatic islet β-cells is rapidly increased in response to glucose addition, and PASK is required for the glucose-responsive expression of some β-cell genes, including preproinsulin (23).

PASK catalytic activity is not responsive to glucose alone, however. The interaction between the hPASK midregion and glycogen synthase is regulated by at least two factors. First, the PAS domain of PAS kinase plays a negative role in regulating this interaction. If the PAS domain is deleted or disrupted, hPASK associates more stably with glycogen synthase. PAS domain function is usually controlled by the metabolic status of the host cell, as has been suggested for the PASK PAS domain (23). This observation raises the intriguing possibility that the hPASK-glycogen synthase interaction is regulated by the metabolic status of the cell, thereby enabling an additional layer of metabolic regulation of glycogen synthesis. Second, glycogen negatively regulates the hPASK-glycogen synthase interaction, which would initially seem counterintuitive, since glycogen would thereby stimulate its own continued synthesis. It is possible, however, that this mechanism exists to spatially coordinate the synthesis of glycogen. It is becoming increasingly apparent that glycogen is synthesized in cells in a highly organized spatial pattern (30). Perhaps one function of hPASK is to maintain free, unlocalized glycogen synthase in a phosphorylated, inactive form until it is properly localized to an existing, properly organized glycogen particle. These data strongly suggest that the hPASK midregion plays an important role in targeting hPASK catalytic activity to specific substrates within the cell.

Since hPASK has been recently implicated in glucose-sensing and glucose-responsive transcription, it appears likely that glucose signaling by means of hPASK affects glycogen metabolism in vivo. It is well-established that derangement in glycogen metabolism is one of the hallmarks of both Type 1 and Type 2 diabetes (20) and related conditions (21), including a panoply of life-threatening cardiovascular conditions (22). Using PASK1 mice, it has further been demonstrated that PASK is indeed required for normal insulin secretion by pancreatic β cells, and that PASK deletion results in nearly complete resistance to the phenotypes caused by a high-fat diet, including obesity, insulin resistance and hepatic fat accumulation. Therefore, PASK inhibition would comprise a system for the metabolic control of glucose utilization and storage in mammalian cells, and offer a new method to treat metabolic diseases including but not limited to diabetes and its complications, the metabolic syndrome, insulin resistance, and various cardiovascular conditions.

Novel compounds and pharmaceutical compositions, certain of which have been found to inhibit PASK have been discovered, together with methods of synthesizing and using the compounds including methods for the treatment of PASK-mediated diseases in a patient by administering the compounds.

In certain embodiments of the present invention, a compound has structural Formula I:

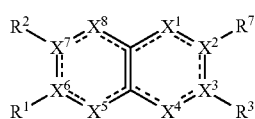

(I)

or a pharmaceutically acceptable salt, ester, or prodrug thereof, wherein:
$X^1$ is chosen from CH, C—COOH, N, and a bond;
$X^2$, $X^3$, $X^6$, $X^7$, and $X^8$, are independently chosen from C, CH, and N;
$X^4$ is chosen from CH, N, NH, O and S;
$X^5$ is chosen from CH, N, and a bond;
$R^1$ is chosen from phenyl and heteroaryl, either of which may be optionally substituted;
$R^2$ is chosen from alkyl, phenyl, and heteroaryl, any of which may be optionally substituted;
$R^3$ is chosen from null, hydrogen, hydroxyl, $C_1$-$C_5$ alkyl, and $C_1$-$C_5$ alkoxy;
$R^7$ is chosen from hydrogen, $COOR^8$, cyano, CHCH-$COOR^8$, $CH_2OH$, $C(O)NHOR^8$, and $SO_2NR^{8a}R^{8b}$;
$R^8$, $R^{8a}$, and $R^{8b}$ are chosen from hydrogen and $C_1$-$C_5$ alkyl, or $R^{8a}$ and $R^{8b}$ can be combined to form a heterocycloalkyl; and
each dashed line is optionally a bond, provided that the bicyclic ring system formed is aromatic.

Certain compounds disclosed herein may possess useful PASK modulating activity, and may be used in the treatment or prophylaxis of a disease or condition in which PASK plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for modulating PASK. Other embodiments provide methods for treating a PASK-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of PASK.

In certain embodiments compounds of Formula I are provided wherein $R^1$ is chosen from phenyl and heteroaryl and has one or more substitutents chosen from the following group: hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^4$, $NHSO_2NHR^4$, $NHCOR^4$, $NHCONHR^4$, $CONHR^4$, $CONR^{4a}R^{4b}$, hydroxy and $OCF_3$; $R^4$, $R^{4a}$ and $R^{4b}$ are independently chosen from $C_1$-$C_6$ alkyl, aryl, heteroaryl, aralkyl and heteroaralkyl, any of which may be optionally substituted; and $R^6$ is chosen from hydrogen and $C_1$-$C_5$ alkyl.

In certain embodiments compounds of Formula I are provided wherein $R^2$ is chosen from alkyl, phenyl and heteroaryl and has one or more substitutents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^5$, $NHSO_2NHR^5$, $NHCOR^5$, $NHCONHR^5$, $CONHR^5$, $CONR^{5a}R^{5b}$, hydroxy and $OCF_3$; $R^5$, $R^{5a}$ and $R^{5b}$ are independently chosen from $C_1$-$C_6$ alkyl, aryl, heteroaryl, aralkyl and heteroaralkyl, any of which may be optionally substituted; and $R^6$ is chosen from hydrogen and $C_1$-$C_5$ alkyl.

In certain embodiments, the compound has structural Formula IIa:

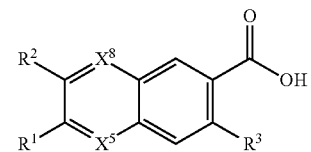

(IIa)

or a salt, ester or prodrug thereof, wherein:
$X^5$ and $X^8$ are independently chosen from CH and N, wherein at least one of $X^5$ and $X^8$ is N;
$R^1$ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^4$, $NHSO_2NHR^4$, $NHCOR^4$, $NHCONHR^4$, $CONHR^4$, $CONR^{4a}R^{4b}$, hydroxy, $OCF_3$;
$R^2$ is chosen from alkyl, aryl and heteroaryl, any of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^5$, $NHSO_2NHR^5$, $NHCOR^5$, $NHCONHR^5$, $CONHR^5$, $CONR^{5a}R^{5b}$, hydroxy, $OCF_3$;
$R^3$ is chosen from null, hydrogen, hydroxyl, $C_1$-$C_5$ alkyl, and $C_1$-$C_5$ alkoxy;
$R^4$, $R^{4a}$ and $R^{4b}$ are independently chosen from $C_1$-$C_6$ alkyl, aryl, heteroaryl, aralkyl and heteroaralkyl, any of which may be optionally substituted;
$R^5$, $R^{5a}$, and $R^{5b}$ are independently chosen from $C_1$-$C_6$ alkyl, aryl, heteroaryl, aralkyl and heteroaralkyl, any of which may be optionally substituted; and
$R^6$ is chosen from hydrogen and $C_1$-$C_5$ alkyl.

In further embodiments, $X^5$ and $X^8$ are N

In certain embodiments, the compound has structural Formula IIb:

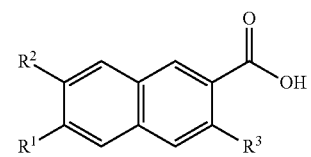

(IIb)

or a salt, ester or prodrug thereof, wherein:
$R^1$ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^4$, $NHSO_2NHR^4$, $NHCOR^4$, $NHCONHR^4$, $CONHR^4$, $CONR^{4a}R^{4b}$, hydroxy, $OCF_3$;

$R^2$ is chosen from alkyl, aryl and heteroaryl, any of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^5$, $NHSO_2NHR^5$, $NHCOR^5$, $NHCONHR^5$, $CONHR^5$, $CONR^{5a}R^{5b}$, hydroxy, $OCF_3$;

$R^3$ is chosen from null, hydrogen, hydroxyl, $C_1$-$C_5$ alkyl, and $C_1$-$C_5$ alkoxy; $R^4$, $R^{4a}$ and $R^{4b}$ are independently chosen from $C_1$-$C_6$ alkyl, aryl, heteroaryl, aralkyl and heteroaralkyl, any of which may be optionally substituted;

$R^5$, $R^{5a}$ and $R^{5b}$ are independently chosen from $C_1$-$C_6$ alkyl, aryl, heteroaryl, aralkyl and heteroaralkyl, any of which may be optionally substituted; and $R^6$ is chosen from hydrogen and $C_1$-$C_5$ alkyl.

In certain embodiments, the compound has structural Formula IIc:

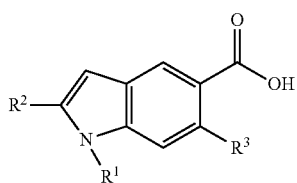

(IIc)

or a salt, ester or prodrug thereof, wherein:

$R^1$ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^4$, $NHSO_2NHR^4$, $NHCOR^4$, $NHCONHR^4$, $CONHR^4$, $CONR^{4a}R^{4b}$, hydroxy, $OCF_3$;

$R^2$ is chosen from alkyl, aryl and heteroaryl, any of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^5$, $NHSO_2NHR^5$, $NHCOR^5$, $NHCONHR^5$, $CONHR^5$, $CONR^{5a}R^{5b}$, hydroxy, $OCF_3$;

$R^3$ is chosen from null, hydrogen, hydroxyl, $C_1$-$C_5$ alkyl, and $C_1$-$C_5$ alkoxy;

$R^4$, $R^{4a}$ and $R^{4b}$ are independently chosen from $C_1$-$C_6$ alkyl, aryl, heteroaryl, aralkyl and heteroaralkyl, any of which may be optionally substituted;

$R^5$, $R^{5a}$, and $R^{5b}$ are independently chosen from $C_1$-$C_6$ alkyl, aryl, heteroaryl, aralkyl and heteroaralkyl, any of which may be optionally substituted; and $R^6$ is chosen from hydrogen and $C_1$-$C_5$ alkyl.

In certain embodiments, the compound has structural Formula IId:

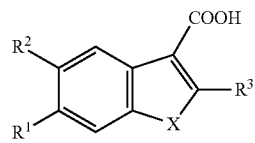

(IId)

or a salt, ester or prodrug thereof, wherein:

X is chosen from NH, S and O;

$R^1$ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^4$, $NHSO_2NHR^4$, $NHCOR^4$, $NHCONHR^4$, $CONHR^4$, $CONR^{4a}R^{4b}$, hydroxy, $OCF_3$;

$R^2$ is chosen from alkyl, aryl and heteroaryl, any of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^5$, $NHSO_2NHR^5$, $NHCOR^5$, $NHCONHR^5$, $CONHR^5$, $CONR^{5a}R^{5b}$, hydroxy, $OCF_3$;

$R^3$ is chosen from null, hydrogen, hydroxyl, $C_1$-$C_5$ alkyl, and $C_1$-$C_5$ alkoxy;

$R^4$, $R^{4a}$ and $R^{4b}$ are independently chosen from $C_1$-$C_6$ alkyl, aryl, heteroaryl, aralkyl and heteroaralkyl, any of which may be optionally substituted;

$R^5$, $R^{5a}$, and $R^{5b}$ are independently chosen from $C_1$-$C_6$ alkyl, aryl, heteroaryl, aralkyl and heteroaralkyl, any of which may be optionally substituted; and $R^6$ is chosen from hydrogen and $C_1$-$C_5$ alkyl.

In certain embodiments, the compound has structural Formula IIe:

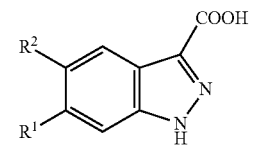

(IIe)

or a salt, ester or prodrug thereof, wherein:

$R^1$ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^4$, $NHSO_2NHR^4$, $NHCOR^4$, $NHCONHR^4$, $CONHR^4$, $CONR^{4a}R^{4b}$, hydroxy, $OCF_3$;

$R^2$ is chosen from alkyl, aryl and heteroaryl, any of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^5$, $NHSO_2NHR^5$, $NHCOR^5$, $NHCONHR^5$, $CONHR^5$, $CONR^{5a}R^{5b}$, hydroxy, $OCF_3$;

$R^4$, $R^{4a}$ and $R^{4b}$ are independently chosen from $C_1$-$C_6$ alkyl, aryl, heteroaryl, aralkyl and heteroaralkyl, any of which may be optionally substituted;

$R^5$, $R^{5a}$, and $R^{5b}$ are independently chosen from $C_1$-$C_6$ alkyl, aryl, heteroaryl, aralkyl and heteroaralkyl, any of which may be optionally substituted; and $R^6$ is chosen from hydrogen and $C_1$-$C_5$ alkyl.

In certain embodiments, the compound has structural Formula IIf:

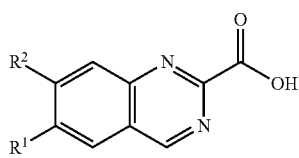

(IIf)

or a salt, ester or prodrug thereof, wherein:

$R^1$ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^4$, $NHSO_2NHR^4$, $NHCOR^4$, $NHCONHR^4$, $CONHR^4$, $CONR^{4a}R^{4b}$, hydroxy, $OCF_3$;

$R^2$ is chosen from alkyl, aryl and heteroaryl, any of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, hydroxyalkyl, nitro, COOH, $NR^6SO_2R^5$, $NHSO_2NHR^5$, $NHCOR^5$, $NHCONHR^5$, $CONHR^5$, $CONR^{5a}R^{5b}$, hydroxy, $OCF_3$;

$R^4$, $R^{4a}$ and $R^{4b}$ are independently chosen from $C_1$-$C_6$ alkyl, aryl, heteroaryl, aralkyl and heteroaralkyl, any of which may be optionally substituted;

$R^5$, $R^{5a}$, and $R^{5b}$ are independently chosen from $C_1$-$C_6$ alkyl, aryl, heteroaryl, aralkyl and heteroaralkyl, any of which may be optionally substituted; and $R^6$ is chosen from hydrogen and $C_1$-$C_5$ alkyl.

Further provided is a compound having structural Formula IIa for use in the manufacture of a medicament for the prevention or treatment of a disease or condition ameliorated by the inhibition of PASK.

Further provided is a pharmaceutical composition comprising a having structural Formula IIa together with a pharmaceutically acceptable carrier.

Further provided is a method of inhibiting PASK comprising contacting PASK with a compound having structural Formula IIa.

Further provided is a method of treatment of a PASK-mediated disease comprising the administration of a therapeutically effective amount of a compound having structural Formula IIa to a patient in need thereof.

In an embodiment, said disease is chosen from cancers, diabetes, insulin resistance, dyslipidemia, non-alcoholic fatty liver disease (NAFLD), and non-alcoholic steatohepatitis (NASH).

Further provided is a method of treatment of a PASK-mediated disease comprising the administration of:
(a) a therapeutically effective amount of a compound having structural Formula IIa; and
(b) another therapeutic agent.

As used herein, the terms below have the meanings indicated.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C:C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, iso-propylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl(hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 3 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain hydrocarbon radical, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be substituted or quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom chosen from O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, 3,4-methylenedioxyphenyl and the like. The heterocycle groups may be optionally substituted unless specifically prohibited.

The term "hydrazinyl" as used herein, alone or in combination, refers to two amino groups joined by a single bond, i.e., —N—N— and not embodied in a ring.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently chosen from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either 1) monocyclic heteroaryl comprising five or six ring members, of which between one and four said members may be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO₃H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)₂—.

The term "N-sulfonamido" refers to a RS(=O)₂NR'— group with R and R' as defined herein.

The term "S-sulfonamido" refers to a —S(=O)₂NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethoxy" refers to a X₃CO— group where X is a halogen.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently chosen from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aralkyl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N₃, SH, SCH₃, C(O)CH₃, CO₂CH₃, CO₂H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH₂CH₃), fully substituted (e.g., —CF₂CF₃), monosubstituted (e.g., —CH₂CH₂F) or substituted at a level anywhere in-between fully substituted and monosubstituted (e.g., —CH₂CF₃). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R″ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"PASK inhibitor" as used herein refers to a compound that exhibits an ($IC_{50}$, $EC_{50}$) with respect to PASK activity of no more than about 100 μM and more typically not more than about 50 μM, as measured in the PASK assay described generally hereinbelow. $IC_{50}$ is that concentration of inhibitors which reduces the activity of PASK to half-maximal level. Certain compounds disclosed herein have been discovered to exhibit inhibition against PASK.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of a compound as disclosed herein, and at least one other agent chosen from the group comprising:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidinedione derivative (glitazone) such as pioglitazone or rosiglitazone; and a non-glitazone type PPARδ agonist e.g. GI-262570;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine or cannabinoid receptor antagonists;

d) anti-hypertensive agents, e.g., loop diuretics such as ethacrynic acid, furosemide and torsemide; diuretics such as thiazide derivatives, chlorothiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutral endopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin n antagonists such as candesartan, eprosartan, irbesartan, losartan, tehnisartan and valsartan, in particular valsartan; renin inhibitors such as aliskiren, terlakiren, ditekiren, RO 66-1132, RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors;
e) an HDL increasing compound;
f) cholesterol absorption modulator such as etizimibe and KT6-971;
g) Apo-A1 analogues and mimetics;
h) thrombin inhibitors such as Ximelagatran;
i) aldosterone inhibitors such as anastrazole, fadrazole, and eplerenone;
j) inhibitors of platelet aggregation such as aspirin, and clopidogrel bisulfate;
k) estrogen, testosterone, a selective estrogen receptor modulator, and a selective androgen receptor modulator;
l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, and compounds decreasing the protein kinase activity such as a PDGF receptor tyrosine kinase inhibitor such as miatinib; and
m) an agent interacting with a 5-HT3 receptor and/or an agent interacting with 5-HT4 receptor such as tegaserod described in the U.S. Pat. No. 5,510,353 as example 13, tegaserod hydrogen maleate, cisapride, and cilansetron.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating PASK-mediated disorders in a human or animal subject in need of such treatment comprising administering to said subject an amount of a compound disclosed herein effective to reduce or prevent said disorder in the subject, optionally in combination with at least one additional agent that is known in the art. In a related aspect, certain embodiments provide therapeutic compositions comprising at least one compound disclosed herein in combination with one or more additional agents for the treatment of PASK-mediated disorders.

Recent studies have found that elevated medium glucose concentrations caused post-translational activation of PASK. It has also been demonstrated that PASK activity is required for glucose-stimulated insulin expression, as shown by studies in PASK1 mice. It has also been demonstrated that PASK deletion results in nearly complete resistance to the phenotypes caused by a high-fat diet, including obesity, insulin resistance and hepatic fat accumulation. It has been postulated that this protection may be due to an increase in AMPK expression in each of the relevant tissues. PASK deletion abrogates nearly all of the maladaptive phenotype associated with a high-fat diet, possibly in part via maintenance of AMPK expression. Increasing AMPK signaling is a proven therapeutic strategy, as illustrated by Metformin, which acts by increasing the phosphorylation and activation of AMPK. Inhibition of PASK signaling elicits similar beneficial effects, but through a distinct mechanism. This complementary therapeutic strategy, either alone or in combination, can be efficacious in the treatment of metabolic diseases. In any case, it appears that PASK inhibition can provide an effective therapeutic strategy for the treatment of diseases, for example Type 2 diabetes, insulin resistance in general, and the metabolic syndrome.

Metabolic syndrome (also known as metabolic syndrome X) is characterized by having at least three of the following symptoms: insulin resistance; abdominal fat—in men this is defined as a 40 inch waist or larger, in women 35 inches or larger; high blood sugar levels—at least 110 milligrams per deciliter (mg/dL) after fasting; high triglycerides—at least 150 mg/dL in the blood stream; low HDL-less than 40 mg/dL; pro-thrombotic state (e.g. high fibrinogen or plasminogen activator inhibitor in the blood); or blood pressure of 130/85 mmHg or higher. A connection has been found between metabolic syndrome and other conditions such as obesity, high blood pressure and high levels of LDL cholesterol, all of which are risk factors for cardiovascular diseases. For example, an increased link between metabolic syndrome and atherosclerosis has been shown. People with metabolic syndrome are also more prone to developing type 2 diabetes, as well as PCOS (polycystic ovarian syndrome) in women and prostate cancer in men.

As described above, insulin resistance can be manifested in several ways, including type 2 diabetes. Type 2 diabetes is the condition most obviously linked to insulin resistance. Compensatory hyperinsulinemia helps maintain normal glucose levels-often for decades, before overt diabetes develops. Eventually the beta cells of the pancreas are unable to overcome insulin resistance through hypersecretion. Glucose levels rise, and a diagnosis of diabetes can be made. Patients with type 2 diabetes remain hyperinsulinemic until they are in an advanced stage of disease. As described above, insulin resistance can also correlate with hypertension. One half of patients with essential hypertension are insulin resistant and hyperinsulinemic, and there is evidence that blood pressure is linked to the degree of insulin resistance. Hyperlipidemia, too, is associated with insulin resistance. The lipid profile of patients with type 2 diabetes includes increased serum very-low-density lipoprotein cholesterol and triglyceride levels and, sometimes, a decreased low-density lipoprotein cholesterol level. Insulin resistance has been found in persons with low levels of high-density lipoprotein. Insulin levels have also been linked to very-low-density lipoprotein synthesis and plasma triglyceride levels.

Accordingly, also disclosed are methods of treating insulin resistance in a subject comprising selecting a subject in need of treatment for insulin resistance; and administering to the subject an effective amount of a compound that inhibits PASK.

Specific diseases to be treated by the compounds, compositions, and methods disclosed herein are those mediated at least in part by PASK. Accordingly, disclosed herein are methods: for reducing glycogen accumulation in a subject; for raising HDL or HDLc, lowering LDL or LDLc, shifting LDL particle size from small dense to normal LDL, lowering VLDL, lowering triglycerides, or inhibiting cholesterol absorption in a subject; for reducing insulin resistance, enhancing glucose utilization or lowering blood pressure in a subject; for reducing visceral fat in a subject; for reducing serum transaminases in a subject; or for treating disease; all comprising the administration of a therapeutic amount of a compound as described herein, to a patient in need thereof. In further embodiments, the disease to be treated may be a metabolic disease. In further embodiment, the metabolic disease may be chosen from: obesity, diabetes melitus, especially Type 2 diabetes, hyperinsulinemia, glucose intolerance, metabolic syndrome X, dyslipidemia, hypertriglyceridemia, hypercholesterolemia, and hepatic steatosis. In other embodiments, the disease to be treated may be chosen from: cardiovascular diseases including vascular disease, atherosclerosis, coronary heart disease, cerebrovascular disease, heart failure and peripheral vessel disease. In preferred embodiments, the methods above do not result in the induction or maintenance of a hypoglycemic state.

Additionally, the PASK modulators disclosed herein may be used to treat proliferative disorders such as cancers. Hematological and non-hematological cancers which may be treated or prevented include but are not limited to multiple myeloma, acute and chronic leukemias including Acute Lymphocytic Leukemia (ALL), Chronic Lymphocytic Leukemia (CLL), and Chronic Myelogenous Leukemia (CLL), lymphomas, including Hodgkin's lymphoma and non-Hodgkin's lymphoma (low, intermediate, and high grade), malignancies of the brain, head and neck, breast, lung, reproductive tract, upper digestive tract, pancreas, liver, renal, bladder, prostate and colon/rectum.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

REFERENCES CITED

The following is a list of references cited herein which, while not necessarily comprehensive, is provided for the convenience of the reader. All references, patents, and patent applications cited herein are hereby incorporated by reference as if written herein in their entireties. When the teachings of these references contradict the teachings presented expressly herein, the present disclosure controls.

1. Roach, P. J. et al. (2001) in The Endocrine Pancreas and Regulation of Metabolism, eds. Cherrington, A. D. & Jefferson, L. S. (Oxford Univ. Press, New York), pp. 609-647.
2. Bergstrom, J. et al. (1967) Acta Physiol. Scand. 71, 140-150.
3. Cline, G. W. et al. (1994) J. Clin. Invest. 94, 2369-2376.
4. Shulman, G. I. et al. G. (1990) N. Engl. J. Med. 322, 223-228.
5. Cohen, P. (1982) Nature 296, 613-620.
6. Roach, P. J. (1986) in The Enzymes, eds. Boyer, P. D. & Krebs, E. G. (Academic, Orlando, Fla.), Vol. 17, pp. 499-539.
7. Cohen, P. (1986) in The Enzymes, eds. Boyer, P. D. & Krebs, E. G. (Academic, Orlando, Fla.), Vol. 17, pp. 461-497.
8. Friedman, D. L. & Larner, J. (1963) Biochemistry 128, 669-675.
9. Larner, J. (1990) Adv. Enzymol. Relat. Areas Mol. Biol. 63, 173-231.
10. Roach, P. J. (1990) FASEB J. 4, 2961-2968.
11. Skurat, A. V., et al. (1994) J. Biol. Chem. 269, 25534-25542.
12. Flotow, H. & Roach, P. J. (1989) J. Biol. Chem. 264, 9126-9128.
13. Nakielny, S., Campbell, D. G. & Cohen, P. (1991) Eur. J. Biochem. 199, 713-722.
14. Wilson W A et al., *Proc Natl Acad Sci USA*. 2005 Nov. 15; 102(46):16596-601, FIG. 6
15. Skurat, A. V. & Roach, P. J. (1995) J. Biol. Chem. 270, 12491-12497.
16. Hardy, T. A. & Roach, P. J. (1993) J. Biol. Chem. 268, 23799-23805
17. Francois, J. & Parrou, J. L. (2001) FEMS Microbiol. Rev. 25, 125-145.
18. Rutter, J., Probst, B. L. & McKnight, S. L. (2002) Cell 111, 17-28.
19. Rutter, J et al. (2001) Proc. Natl. Acad. Sci. USA 98, 8991-8996.
20. Roden M, Bernroider E: *Best Pract Res Clin Endocrinol Metab.* 2003 Sep. 17(3):365-83
21. Van Steenbergen W, Lanckmans S: *Int J Obes Relat Metab Disord.* 1995 Sep. 19 Suppl 3: S27-36.
22. Arad M et al., *Circ Res.* 2007 Mar. 2; 100(4): 474-88
23. da Silva Xavier, G. et al. (2004) Proc. Natl. Acad. Sci. USA 101, 8319-8324.
24. 33Picton, C. et al. (1982) FEBS Lett. 150, 191-196.
25. DePaoli-Roach, A. A. et al., (1983) J. Biol. Chem. 258, 10702-10709.
26. Elia, A. E. et al. (2003) Science 299, 1228-1231.
27. Gao, T. et al. (1997) Neuron 19, 185-196.
28. Wilson, W. A. et al. (1999) Mol. Cell. Biol. 19, 7020-7030.
29. Yedovitzky, M. et al. (1997) J. Biol. Chem. 272, 1417-1420.
30. Fernandez-Novell, J. M., et al. (2002) FEBS Lett. 531, 222-228.

General Synthetic Methods for Preparing Compounds

The following schemes can generally be used to practice the present invention. Example compounds can be prepared using the appropriate scheme.

Scheme 1.

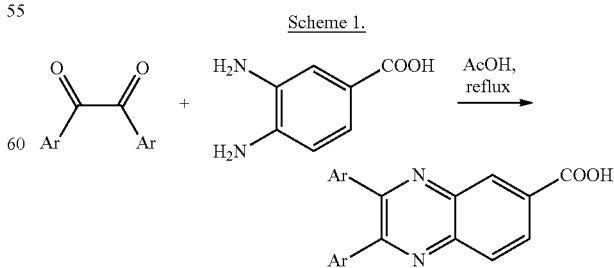

Bioorg. Med. Chem. 13 (2005) 2097-2107.

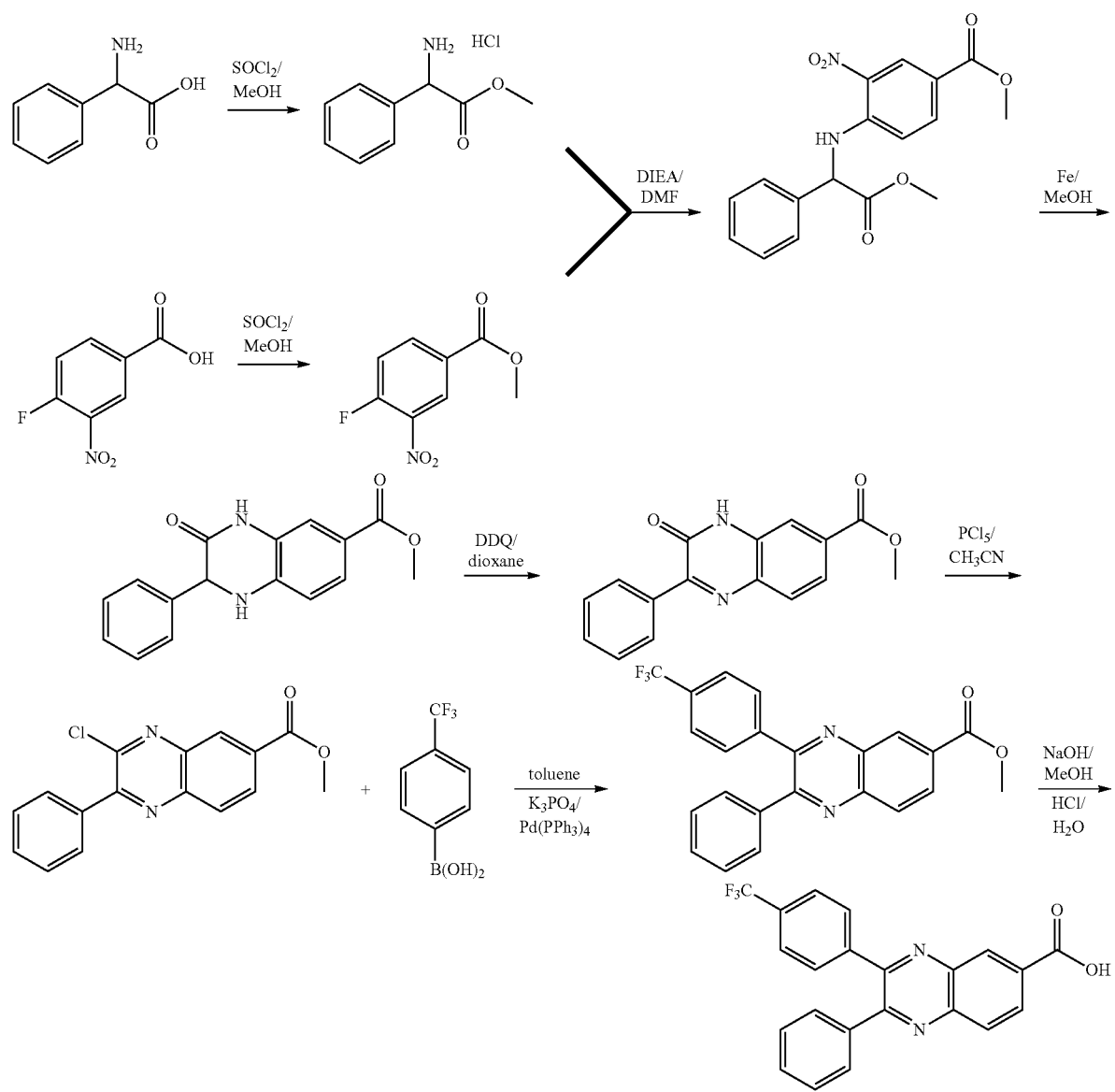
Scheme 2.
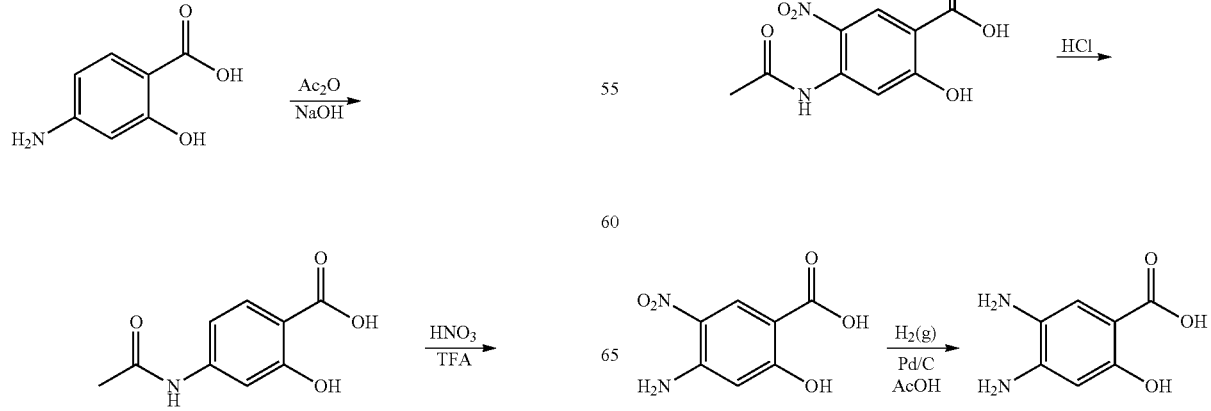
Scheme 3.

Scheme 4.
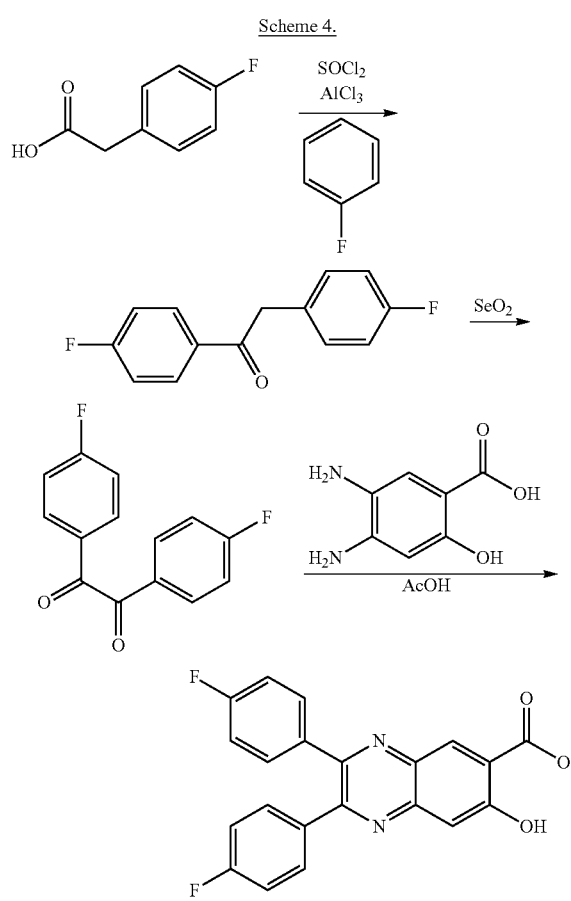
Scheme 5.
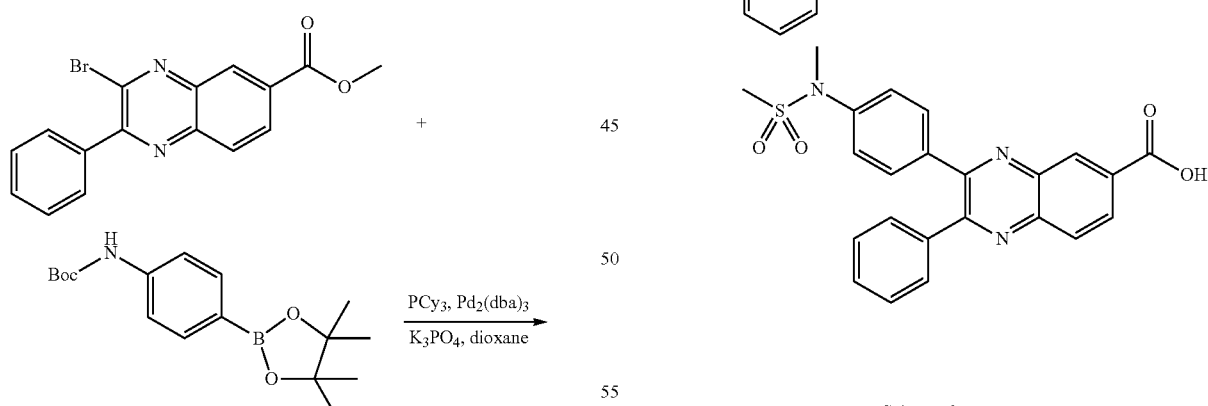
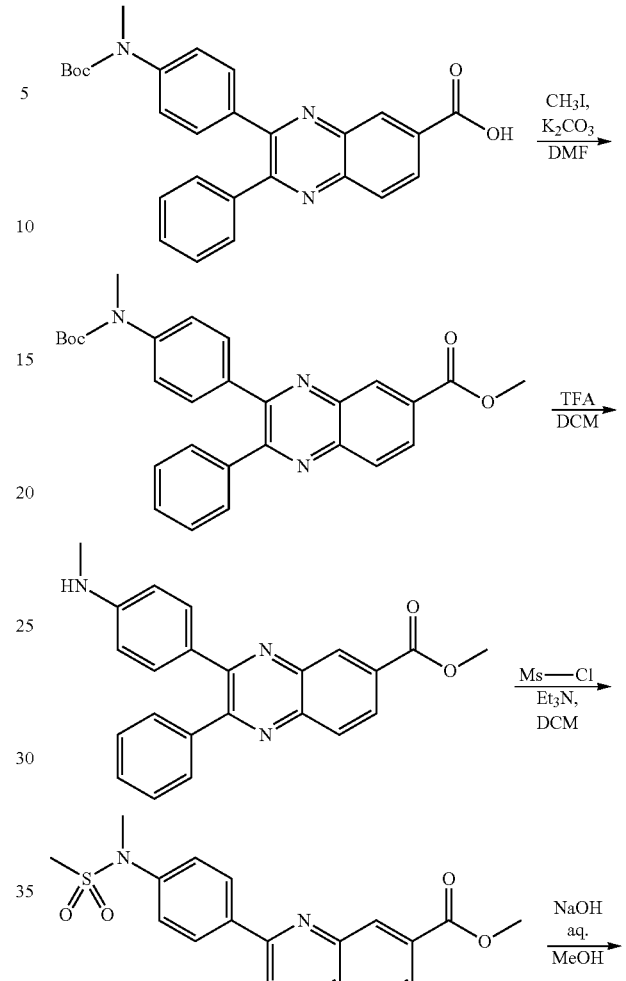
Scheme 6.
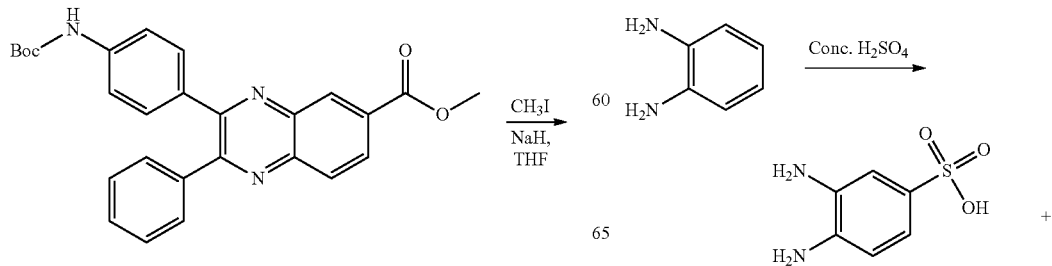

29
-continued
30
-continued
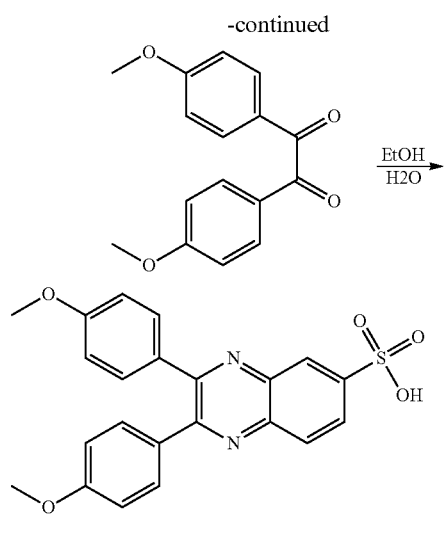
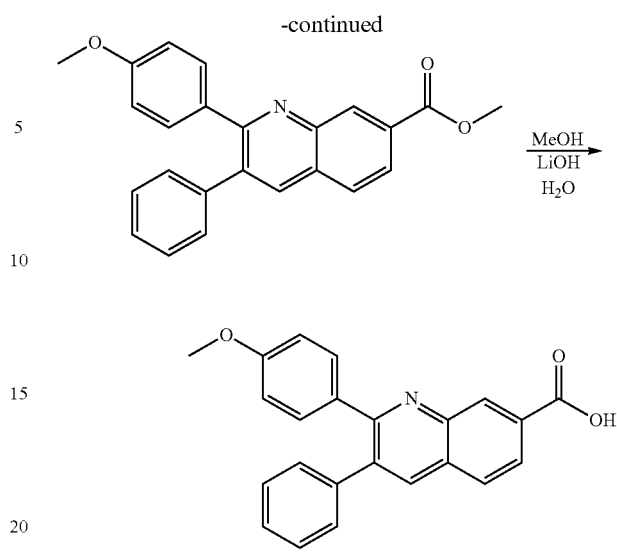
Scheme 7.
Scheme 8.
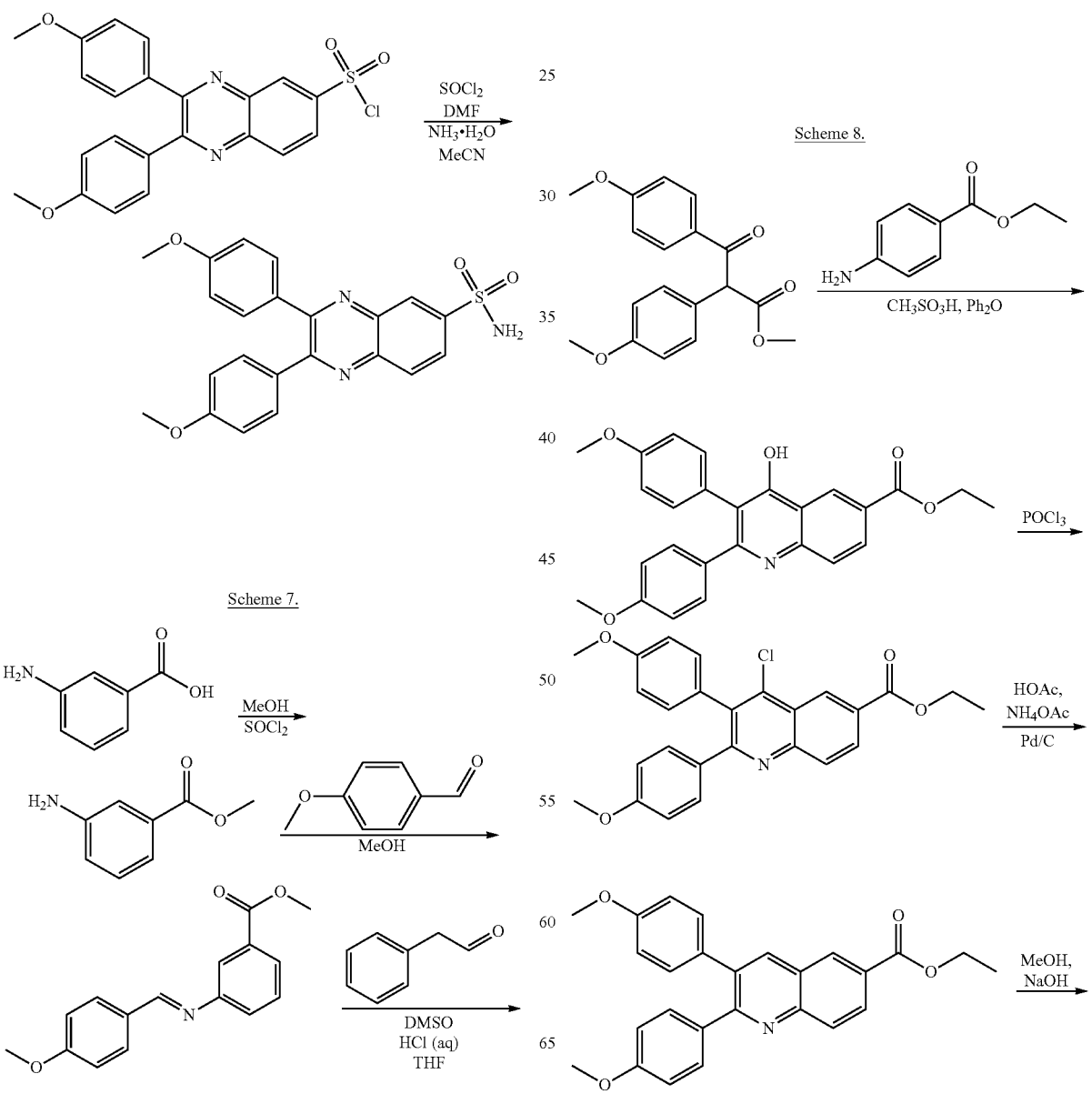

-continued

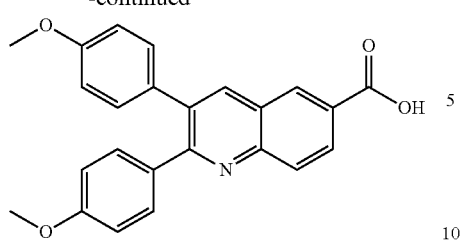

The invention is further illustrated by the following examples, which can be made by the methods above or by one skilled in the art without undue experimentation, or can be purchased from commercial sources.

EXAMPLE 1

2,3-Di-(3-hydroxyphenyl)quinoxaline-6-carboxylic acid

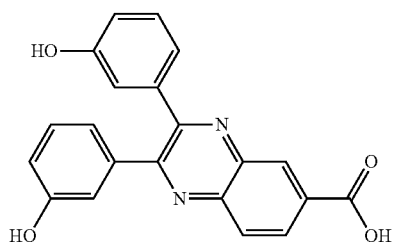 [SMILES: O=C(O)c1ccc2nc(-c3cccc(O)c3)c(-c3cccc(O)c3)nc2c1]

EXAMPLE 2

2,3-Di-(2-hydroxyphenyl)quinoxaline-6-carboxylic acid

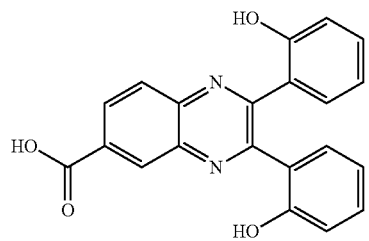 [SMILES: O=C(O)c1ccc2nc(-c3ccccc3O)c(-c3ccccc3O)nc2c1]

EXAMPLE 3

7-Hydroxy-2-phenyl-3-methylquinoxaline-6-carboxylic acid

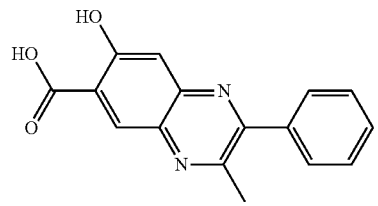 [SMILES: Cc1nc2cc(C(=O)O)c(O)cc2nc1-c1ccccc1]

EXAMPLE 4

2,3-Di-(3,4-dimethoxyphenyl)quinoxaline-6-carboxylic acid

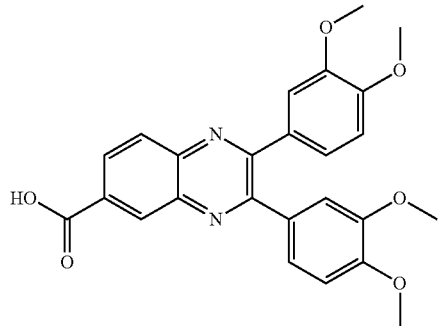 [SMILES: COc1ccc(-c2nc3ccc(C(=O)O)cc3nc2-c2ccc(OC)c(OC)c2)cc1OC]

EXAMPLE 5

2,3-Di-(4-fluorophenyl)quinoxaline-6-carboxylic acid

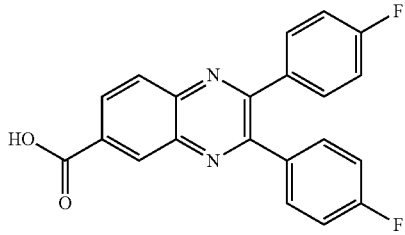 [SMILES: O=C(O)c1ccc2nc(-c3ccc(F)cc3)c(-c3ccc(F)cc3)nc2c1]

EXAMPLE 6

2,3-Di-(3,4-methylenedioxyphenyl)quinoxaline-6-carboxylic acid

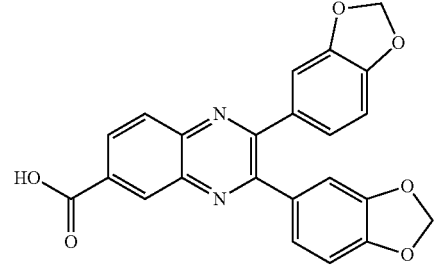 [SMILES: O=C(O)c1ccc2nc(-c3ccc4c(c3)OCO4)c(-c3ccc4c(c3)OCO4)nc2c1]

EXAMPLE 7

2,3-Di-(4-methylphenyl)quinoxaline-6-carboxylic acid

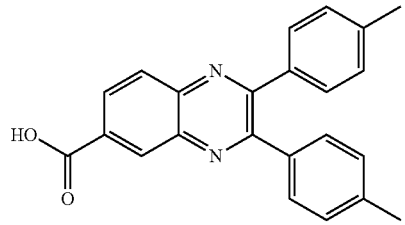 [SMILES: Cc1ccc(-c2nc3ccc(C(=O)O)cc3nc2-c2ccc(C)cc2)cc1]

EXAMPLE 8

2,3-Diphenylquinoxaline-6-carboxylic acid

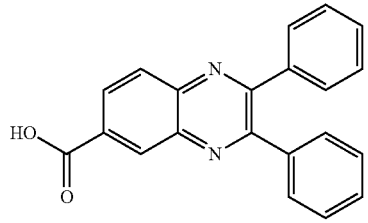 [SMILES: O=C(O)c1ccc2nc(-c3ccccc3)c(-c3ccccc3)nc2c1]

EXAMPLE 9

2,3-Di-(2-furyl)quinoxaline-6-carboxylic acid

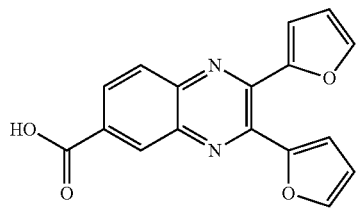 [SMILES: O=C(O)c1ccc2nc(-c3ccco3)c(-c3ccco3)nc2c1]

EXAMPLE 10

2,3-Di-(3,4-methylenedioxyphenyl)quinoxaline-7-hydroxy-6-carboxylic acid

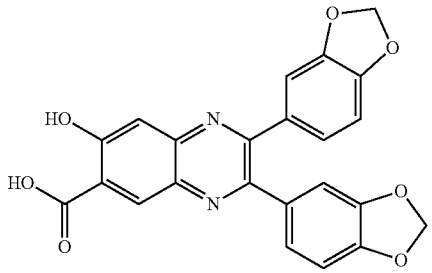 [SMILES: O=C(O)c1cc2nc(-c3ccc4c(c3)OCO4)c(-c3ccc4c(c3)OCO4)nc2cc1O]

EXAMPLE 11

2,3-Di-(4-ethoxyphenyl)quinoxaline-6-carboxylic acid

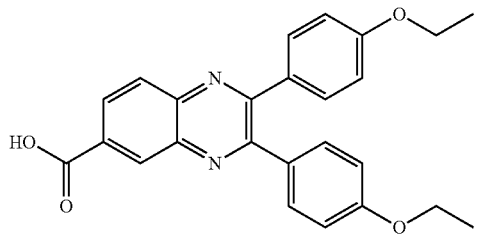 [SMILES: CCOc1ccc(-c2nc3ccc(C(=O)O)cc3nc2-c2ccc(OCC)cc2)cc1]

EXAMPLE 12

2-(Furan-2-yl)-3-phenylquinoxaline-6-carboxylic acid

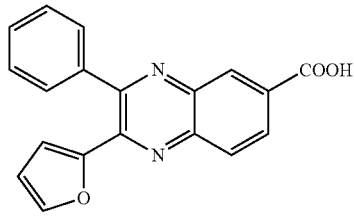 [SMILES: O=C(O)c1ccc2nc(-c3ccco3)c(-c3ccccc3)nc2c1]

A solution of 1-(furan-2-yl)-2-phenylethane-1,2-dione (100 mg, 0.50 mmol, 1.00 equiv) and 3,4-diaminobenzoic acid (76 mg, 0.50 mmol, 1.00 equiv) in AcOH (3 mL) was stirred under reflux for 3 hrs in a 50-mL round-bottom flask. The resulting mixture was concentrated under vacuum, quenched with water. Solids were collected by filtration affording 43 mg (27%) of 2-(furan-2-yl)-3-phenylquinoxaline-6-carboxylic acid as a grey solid.

LC-MS (ES, m/z): [M+H]+ calculated for $C_{19}H_{13}N_2O_3$: 317. Found: 317.

$^1$H-NMR (400 MHz, DMSO, ppm): δ 13.40 (1H, s), 8.57-8.62 (1H, d), 8.15-8.31 (2H, m), 7.85-7.84 (1H, d), 7.53-7.60 (5H, m), 6.57 (1H, s), 6.33-6.36 (1H, m).

EXAMPLE 13

2-Phenyl-3-(4-(trifluoromethyl)phenyl)quinoxaline-6-carboxylic acid

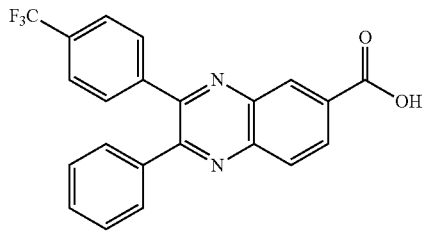

Step 1. Methyl 4-fluoro-3-nitrobenzoate

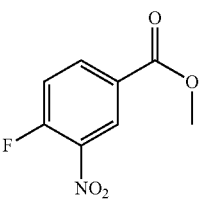

Thionyl chloride (24 g, 201.68 mmol, 1.01 equiv) was added dropwise with stirring at 0° C. to a solution of 4-fluoro-3-nitrobenzoic acid (37 g, 200.00 mmol, 1.00 equiv) in MeOH (400 mL) and allowed to react, with stifling, for 3 hrs under reflux. The resulting mixture was concentrated under vacuum, diluted with 500 mL of EA, and washed with 3×200 mL of saturated $NaHCO_3$ and 1×200 mL of brine. The mixture was dried over anhydrous sodium sulfate and concentrated under vacuum affording 40 g (crude) of methyl 4-fluoro-3-nitrobenzoate as a white solid.

Step 2. Methyl 4-(2-methoxy-2-oxo-1-phenylethylamino)-3-nitrobenzoate

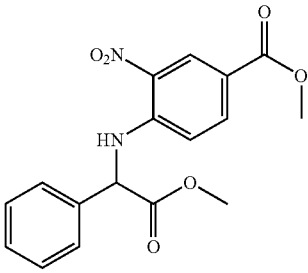 [SMILES: COC(=O)c1ccc(NC(C(=O)OC)c2ccccc2)c([N+](=O)[O-])c1]

Methyl 2-amino-2-phenylacetate hydrochloride (500 mg, 2.48 mmol, 1.00 equiv) in DMF (5 mL), methyl 4-fluoro-3-nitrobenzoate (1.0 g, 5.03 mmol, 2.00 equiv), and DIEA (1 g, 7.75 mmol, 3.13 equiv) were combined in a 50-mL round-bottom flask and allowed to react, with stifling, overnight at room temperature. The reaction was then quenched by the addition of 100 mL of water. The solids were collected by filtration, resulting in 0.9 g (crude) of methyl 4-(2-methoxy-2-oxo-1-phenylethylamino)-3-nitrobenzoate as a yellow solid.

Step 3. Methyl 3-oxo-2-phenyl-1,2,3,4-tetrahydroquinoxaline-6-carboxylate

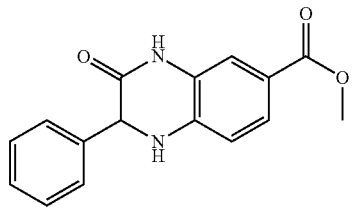 [SMILES: COC(=O)c1ccc2c(c1)NC(=O)C(c1ccccc1)N2]

To a solution of methyl 4-(2-methoxy-2-oxo-1-phenylethylamino)-3-nitrobenzoate (350 mg, 1.02 mmol, 1.00 equiv) in MeOH (10 mL) was added Fe (280 mg, 5.00 mmol, 5.00 equiv) and saturated $NH_4Cl$ (3 mL), and the resulting solution was allowed to react, with stifling, for 2 hrs while the temperature was maintained at reflux in an oil bath. The solids were collected by filtration and discarded. The resulting solution was concentrated under vacuum giving 0.8 g (crude) of methyl 3-oxo-2-phenyl-1,2,3,4-tetrahydroquinoxaline-6-carboxylate as a yellow solid.

Step 4. Methyl 3-oxo-2-phenyl-3,4-dihydroquinoxaline-6-carboxylate

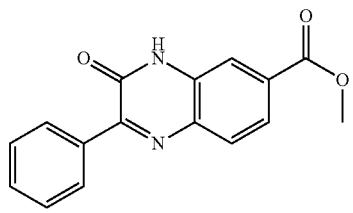 [SMILES: COC(=O)c1ccc2nc(-c3ccccc3)c(=O)[nH]c2c1]

A solution of methyl 3-oxo-2-phenyl-1,2,3,4-tetrahydroquinoxaline-6-carboxylate (400 mg, 0.57 mmol, 1.00 equiv, 40%) in dioxane (30 mL) and DDQ (340 mg, 1.50 mmol, 2.64 equiv) was allowed to react, with stirring, for 3 hrs at room temperature in a 50-mL round-bottom flask. The solids were collected by filtration and discarded. The resulting mixture was washed with 1×20 mL of saturated $K_2CO_3$, and the organic layer was concentrated in vacuo to result in 10 mg (6%) of methyl 3-oxo-2-phenyl-3,4-dihydroquinoxaline-6-carboxylate as a yellow solid.

Step 5. Methyl 3-chloro-2-phenylquinoxaline-6-carboxylate

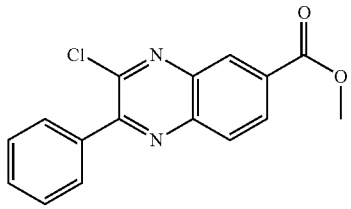 [SMILES: COC(=O)c1ccc2nc(-c3ccccc3)c(Cl)nc2c1]

Methyl 3-oxo-2-phenyl-3,4-dihydroquinoxaline-6-carboxylate (100 mg, 0.36 mmol, 1.00 equiv) and $PCl_5$ (220 mg, 1.07 mmol, 3.00 equiv) in $CH_3CN$ (10 mL) was allowed to react, with stifling, for 5 hrs while the temperature was maintained at reflux in an oil bath. The reaction was then quenched by the addition of 50 mL of water, and the pH value of the solution was adjusted to 9 with saturated $K_2CO_3$. The resulting solution was extracted with 3×50 mL of ethyl acetate, the organic layers combined and dried over anhydrous sodium sulfate, and concentrated under vacuum, affording 60 mg (56%) of methyl 3-chloro-2-phenylquinoxaline-6-carboxylate as a yellow solid.

Step 6. Methyl 2-phenyl-3-(4-(trifluoromethyl)phenyl)quinoxaline-6-carboxylate

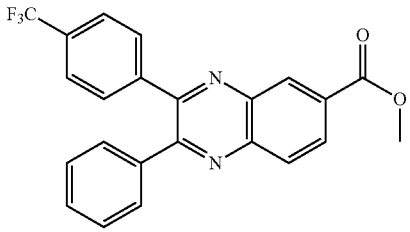 [SMILES: COC(=O)c1ccc2nc(-c3ccccc3)c(-c3ccc(C(F)(F)F)cc3)nc2c1]

A suspension of methyl 3-chloro-2-phenylquinoxaline-6-carboxylate (100 mg, 0.33 mmol, 1.00 equiv), 4-(trifluoromethyl)phenylboronic acid (69.9 mg, 0.37 mmol, 1.10 equiv), $K_3PO_4$ (142 mg, 0.67 mmol, 2.00 equiv), $Pd(PPh_3)_4$ (11 mg, 0.01 mmol, 0.03 equiv) in toluene (1 mL) was placed in a 10-mL sealed tube under an inert atmosphere allowed to react, with stifling, overnight at 100° C. in an oil bath. The reaction was quenched by the addition of 20 mL of water, and the solids were collected by filtration, resulting in 80 mg (59%) of methyl 2-phenyl-3-(4-(trifluoromethyl)phenyl)quinoxaline-6-carboxylate as a yellow solid.

Step 7. 2-phenyl-3-(4-(trifluoromethyl)phenyl)quinoxaline-6-carboxylic acid

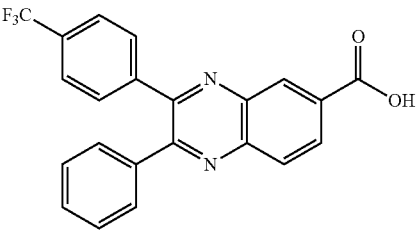

A solution of methyl 2-phenyl-3-(4-(trifluoromethyl)phenyl)quinoxaline-6-carboxylate (80 mg, 0.20 mmol, 1.00 equiv) in MeOH (10 mL) and NaOH (23.5 mg, 3.00 equiv) was placed in a 50-mL round-bottom flask and allowed to react, with stirring, for 3 hrs while the temperature was maintained at 50° C. in an oil bath. The pH value of the solution was adjusted to 3 with HCl (2N). The resulting solids were collected by filtration, yielding 35 mg (45%) of 2-phenyl-3-(4-(trifluoromethyl)phenyl)quinoxaline-6-carboxylic acid as a yellow solid.

LC-MS (ES, m/z): [M+H]$^+$ calculated for $C_{22}H_{14}F_3N_2O_2$: 395. Found: 395.

$^1$H-NMR (400 MHz, CD$_3$OD, ppm): δ 8.21 (1H, s), 7.70-7.73 (5H, d, J=14.4 Hz), 7.54-7.55 (2H, d, J=6 Hz), 7.42-7.46 (4H, t).

EXAMPLE 14

3-Methyl-2-phenylquinoxaline-6-carboxylic acid

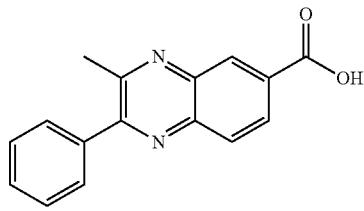 [SMILES: Cc1nc2cc(C(=O)O)ccc2nc1-c1ccccc1]

Step 1. Methyl 3-methyl-2-phenylquinoxaline-6-carboxylate

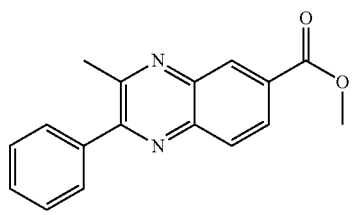 [SMILES: COC(=O)c1ccc2nc(-c3ccccc3)c(C)nc2c1]

A suspension of methyl 3-chloro-2-phenylquinoxaline-6-carboxylate (100 mg, 0.34 mmol, 1.00 equiv), Pd$_2$(dba)$_3$ (12 mg, 0.01 mmol, 0.04 equiv), x-phos (6 mg, 0.01 mmol, 0.04 equiv), and Al(CH$_3$)$_3$ (0.5 mL, 3.00 equiv, 2.5M) in 1,4-dioxane (3 mL) was placed in a 10-mL sealed tube under an inert atmosphere allowed to react, with stirring, for 6 hr while the temperature was maintained at 100° C. in an oil bath. The reaction progress was monitored by TLC (ethyl acetate:petroleum ether (1:1)). The resulting mixture was concentrated under vacuum. The residue was purified via silica gel column (ethyl acetate/petroleum ether (1:20)) yielding 60 mg (64%) of methyl 3-methyl-2-phenylquinoxaline-6-carboxylate as a yellow solid.

Step 2. 3-methyl-2-phenylquinoxaline-6-carboxylic acid

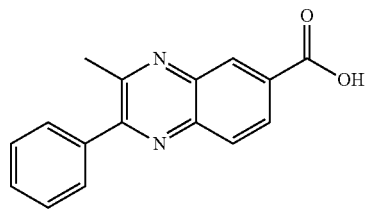 [SMILES: Cc1nc2cc(C(=O)O)ccc2nc1-c1ccccc1]

A solution of methyl 3-methyl-2-phenylquinoxaline-6-carboxylate (90 mg, 0.32 mmol, 1.00 equiv) and LiOH (20.7 mg, 0.90 mmol, 5.00 equiv) in 1,4-dioxane/H$_2$O (9/3 mL) was placed in a 50-mL round-bottom flask and allowed to react, with stirring, for 1 hr while the temperature was maintained at reflux in an oil bath. The resulting mixture was concentrated under vacuum, and the pH adjusted to 4 with HCl (1M). The solids were collected by filtration and dried in an oven under reduced pressure, yielding 30 mg (33%) of 3-methyl-2-phenylquinoxaline-6-carboxylic acid as a white solid.

LC-MS (ES, m/z): [M+H]+ calculated for $C_{16}H_{12}N_2O_2$: 265. Found: 265.

$^1$H-NMR (300 MHz, DMSO, ppm): δ 2.884 (3H, s), 7.578-7.595 (3H, m), 7.719 (2H, m), 8.225-8.253 (1H, d, 8.4 Hz), 8.407-8.434 (1H, d, 8.1 Hz), 8.936 (1H, s).

EXAMPLE 15

Methyl 2-phenyl-3-p-tolylquinoxaline-6-carboxylate

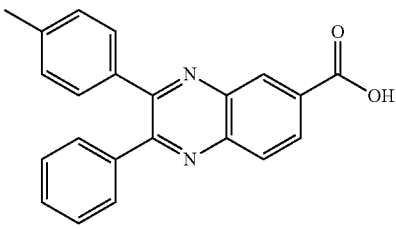 [SMILES: Cc1ccc(-c2nc3cc(C(=O)O)ccc3nc2-c2ccccc2)cc1]

Step 1. Methyl 2-phenyl-3-p-tolylquinoxaline-6-carboxylate

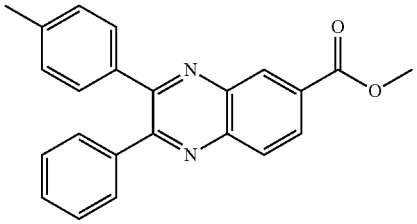

The ester product was obtained via a Suzuki coupling reaction using the method previously shown in Example 13, Step 6. Methyl 3-chloro-2-phenylquinoxaline-6-carboxylate (100 mg, 0.34 mmol, 1.00 equiv) and p-tolylboronic acid (54 mg, 0.4 mmol, 1.10 equiv) were used as starting materials and chromatography was performed with ethyl acetate/petroleum ether (1:20) as the eluent, affording 90 mg (76%) of methyl 2-phenyl-3-p-tolylquinoxaline-6-carboxylate as a yellow solid.

Step 2. 2-Phenyl-3-p-tolylquinoxaline-6-carboxylic acid

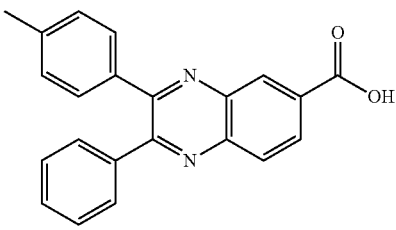 [SMILES: Cc1ccc(-c2nc3cc(C(=O)O)ccc3nc2-c2ccccc2)cc1]

The carboxylic acid product was obtained via deprotection of the ester using the same method as Example 14, step 2, using methyl 2-phenyl-3-p-tolylquinoxaline-6-carboxylate-6-carboxylate (50 mg, 0.14 mmol, 1.00 equiv) as the reactant, affording 30 mg (60%) of 2-phenyl-3-p-tolylquinoxaline-6-carboxylic acid as a white solid.

LC-MS (ES, m/z): [M+H]+ calculated for $C_{22}H_{16}N_2O_2$: 341. Found 341.

$^1$H-NMR (300 MHz, DMSO, ppm): δ 2.387 (3H, s), 7.173-7.200 (2H, m), 7.379-7.434 (5H, m), 7.525-7.548 (2H, m), 8.136-8.166 (1H, d, 9 Hz), 8.379-8.409 (1H, d, 9 Hz), 8.761 (1H, s).

EXAMPLE 16

3-(4-Ethoxyphenyl)-2-phenylquinoxaline-6-carboxylic acid

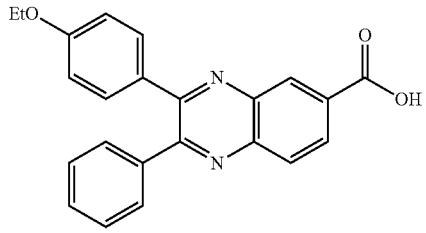 [SMILES: CCOc1ccc(-c2nc3cc(C(=O)O)ccc3nc2-c2ccccc2)cc1]

Step 1. Methyl 3-(4-ethoxyphenyl)-2-phenylquinoxaline-6-carboxylate

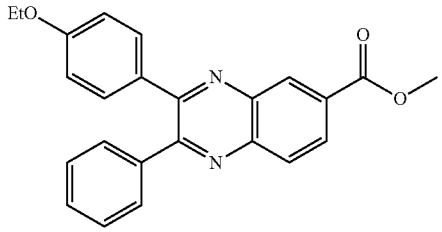 [SMILES: CCOc1ccc(-c2nc3cc(C(=O)OC)ccc3nc2-c2ccccc2)cc1]

The ester product was obtained via a Suzuki coupling reaction using the method previously shown in Example 13, Step 6, with methyl 3-chloro-2-phenylquinoxaline-6-carboxylate (100 mg, 0.34 mmol, 1.00 equiv) and 4-ethoxyphenylboronic acid (61 mg, 0.37 mmol, 1.10 equiv) As reactants. Purification via silica gel column (ethyl acetate/petroleum ether (1:5)) yielded 55 mg (43%) of methyl 3-(4-ethoxyphenyl)-2-phenylquinoxaline-6-carboxylate as a yellow powder.

Step 2. 3-(4-Ethoxyphenyl)-2-phenylquinoxaline-6-carboxylic acid

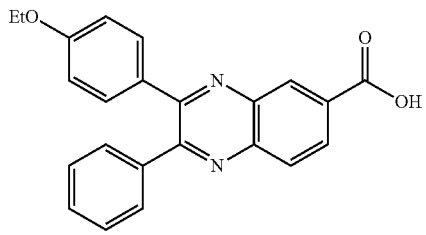 [SMILES: CCOc1ccc(-c2nc3cc(C(=O)O)ccc3nc2-c2ccccc2)cc1]

The carboxylic acid product was obtained via deprotection of the ester using the same method as Example 14, step 2, with methyl 3-(4-ethoxyphenyl)-2-phenylquinoxaline-6-carboxylate (55 mg, 0.14 mmol, 1.00 equiv) as the reactant, affording 45 mg (82%) of 3-(4-ethoxyphenyl)-2-phenylquinoxaline-6-carboxylic acid as a white solid.

LC-MS (ES, m/z): [M+H]+ calculated for $C_{23}H_{20}N_2O_3$: 371. Found: 371.

$^1$H-NMR (300 MHz, DMSO): δ 6.89 (2H, d, J=9 Hz), 7.42 (5H, t, J=9 Hz), 7.51 (2H, m), 8.07 (1H, d, J=8.4 Hz), 8.29 (1H, dd, J=1.5 Hz, 8.7 Hz), 8.54 (1H, s).

EXAMPLE 17

3-(3,4-Dimethoxyphenyl)-2-phenylquinoxaline-6-carboxylic acid

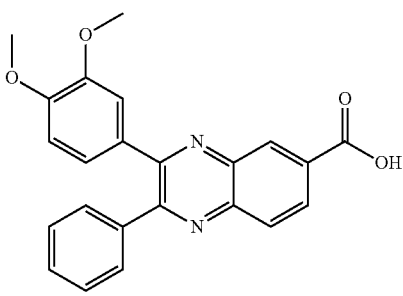 [SMILES: COc1ccc(-c2nc3cc(C(=O)O)ccc3nc2-c2ccccc2)cc1OC]

The ester product was obtained via a Suzuki coupling reaction using the method previously shown in Example 13, Step 6, with methyl 3-bromo-2-phenylquinoxaline-6-carboxylate (100 mg, 0.29 mmol, 1.00 equiv) and 3,4-dimethoxyphenylboronic acid (80 mg, 0.44 mmol, 1.50 equiv) as reactants. Purification by Prep-TLC (silica gel) yielded 50 mg (44%) of 3-(3,4-dimethoxyphenyl)-2-phenylquinoxaline-6-carboxylic acid as a yellow solid.

LC-MS: (ES, m/z): [M+H]+ calculated. for $C_{23}H_{18}N_2O_4$: 387. Found: 387.

$^1$H-NMR (DMSO, ppm): δ 3.529 (3H, s), 3.792 (3H, s), 6.966-7.024 (2H, m), 7.138-7.162 (1H, m), 7.435-7.510 (5H, m), 8.085-8.112 (1H, m), 8.321 (1H, m), 8.608 (1H, s).

EXAMPLE 18

3-(Naphthalen-2-yl)-2-phenylquinoxaline-6-carboxylic acid

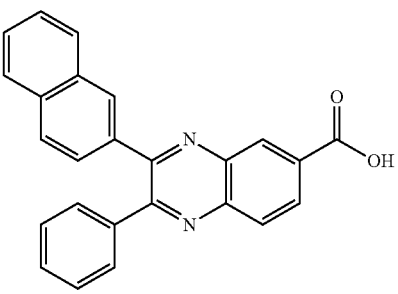 [SMILES: O=C(O)c1ccc2nc(-c3ccccc3)c(-c3ccc4ccccc4c3)nc2c1]

Step 1. Methyl 3-(naphthalen-2-yl)-2-phenylquinoxaline-6-carboxylate

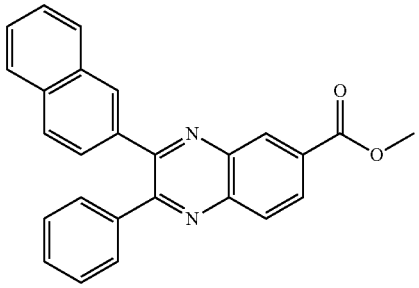 [SMILES: COC(=O)c1ccc2nc(-c3ccccc3)c(-c3ccc4ccccc4c3)nc2c1]

The ester product was obtained via a Suzuki coupling reaction using the method previously shown in Example 13, Step 6, with methyl 3-chloro-2-phenylquinoxaline-6-carboxylate (100 mg, 0.34 mmol, 1.00 equiv) and naphthalen-2-yl boronic acid (63 mg, 0.37 mmol, 1.10 equiv). Purification via silica gel column (ethyl acetate/petroleum ether (1:20)) yielded 62 mg (47%) of methyl 3-(naphthalen-2-yl)-2-phenylquinoxaline-6-carboxylate as a yellow solid.

Step 2. 3-(Naphthalen-2-yl)-2-phenylquinoxaline-6-carboxylic acid

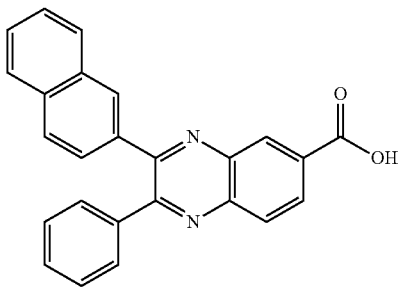 [SMILES: O=C(O)c1ccc2nc(-c3ccccc3)c(-c3ccc4ccccc4c3)nc2c1]

The carboxylic acid product was obtained via deprotection of the ester using the same method as Example 14, step 2, with methyl 3-(naphthalen-2-yl)-2-phenylquinoxaline-6-carboxylate (63 mg, 0.16 mmol, 1.00 equiv) as the reactant, yielding 49 mg (79%) of 3-(naphthalen-2-yl)-2-phenylquinoxaline-6-carboxylic acid as a yellow powder.

LC-MS (ES, m/z): [M+H]+ calculated for $C_{25}H_{17}N_2O_2$: 377. Found: 377.

$^1$H-NMR (300 MHz, DMSO): δ 7.34-7.42 (3H, m), 7.53-7.60 (5H, m), 7.87-7.96 (3H, m), 8.18 (1H, s), 8.27-8.37 (2H, m), 8.72 (2H, d, J=1.2 Hz).

EXAMPLE 19

3-(Naphthalene-1-yl)-2-phenylquinoxaline-6-carboxylic acid

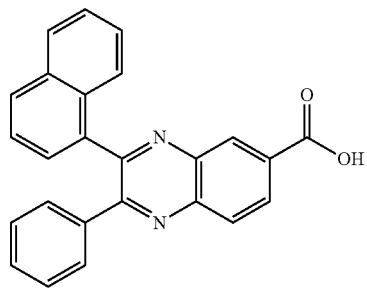 [SMILES: O=C(O)c1ccc2nc(-c3ccccc3)c(-c3cccc4ccccc34)nc2c1]

Step 1. Methyl 3-(naphthalen-1-yl)-2-phenylquinoxaline-6-carboxylate

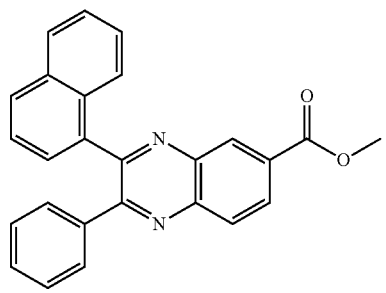 [SMILES: COC(=O)c1ccc2nc(-c3ccccc3)c(-c3cccc4ccccc34)nc2c1]

The ester product was obtained via a Suzuki coupling reaction using the method previously shown in Example 13, Step 6, using methyl 3-chloro-2-phenylquinoxaline-6-carboxylate (100 mg, 0.34 mmol, 1.00 equiv) and naphthalen-1-yl boronic acid (63 mg, 0.37 mmol, 1.10 equiv) as reactants. Purification via silica gel column (ethyl acetate/petroleum ether (1:20)) afforded 90 mg (69%) of methyl 3-(naphthalen-1-yl)-2-phenylquinoxaline-6-carboxylate as a yellow powder.

Step 2. 3-(Naphthalen-1-yl)-2-phenylquinoxaline-6-carboxylic acid

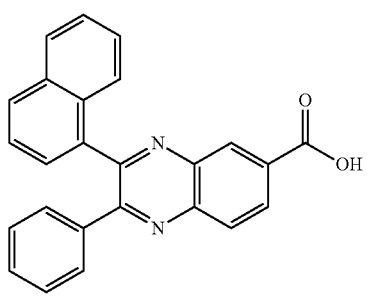 [SMILES: O=C(O)c1ccc2nc(-c3ccccc3)c(-c3cccc4ccccc34)nc2c1]

The carboxylic acid product was obtained via deprotection of the ester using the same method as Example 14, step 2, with methyl 3-(naphthalen-1-yl)-2-phenylquinoxaline-6-carboxylate (75 mg, 0.19 mmol, 1.00 equiv) as the reactant afforded 60 mg (78%) of 3-(naphthalen-1-yl)-2-phenylquinoxaline-6-carboxylic acid as a brown powder.

LC-MS (ES, m/z): [M+H]+ calcd for $C_{25}H_{17}N_2O_2$: 377. Found: 377.

$^1$H-NMR (300 MHz, DMSO): δ 7.16-7.25 (3H, m), 7.38-7.44 (3H, m), 7.49-7.55 (3H, m), 7.64-7.66 (1H, d, J=8.4 Hz), 7.98-8.04 (2H, m), 8.33-8.42 (2H, m), 8.68 (1H, s).

EXAMPLE 20

3-(Benzo[d][1,3]dioxol-5-yl)-2-phenylquinoxaline-6-carboxylic acid

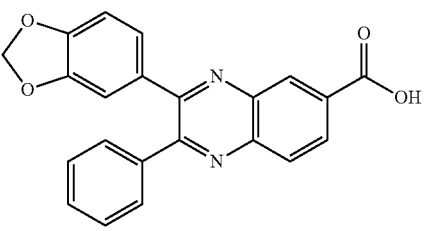 [SMILES: O=C(O)c1ccc2nc(-c3ccccc3)c(-c3ccc4c(c3)OCO4)nc2c1]

Step 1. 5-Bromobenzo[d][1,3]dioxole

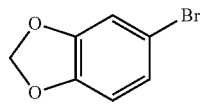

A solution of benzo[d][1,3]dioxole (6.1 g, 50.00 mmol, 1.00 equiv) and N-bromo-succinamide (NBS) (9.3 g, 52.5 mmol, 1.05 equiv) in CHCl$_3$ (25 mL) in a 100-mL round-bottom flask and allowed to react, with stirring, for 3 hr while the temperature was maintained at reflux. The resulting mixture was concentrated under vacuum and purified via silica gel column (ethyl acetate:petroleum ether (1:20)) giving 9.5 g (90%) of 5-bromobenzo[d][1,3]dioxole as yellow oil.

Step 2. Benzo[d][1,3]dioxol-5-ylboronic acid

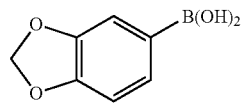

Butyl lithium (BuLi) (5.6 mL, 1.40 equiv) was added dropwise to a solution of 5-bromobenzo[d][1,3]dioxole (2 g, 9.95 mmol, 1.00 equiv) and triisopropyl borate (1.96 g, 14.00 mmol, 1.40 equiv) in THF (20 mL) at −78° C. in a 100-mL 3-necked round-bottom flask under an inert atmosphere of nitrogen. The mixture was stirred at room temperature for 4 hr, quenched with water (10 mL), and acidified with H$_2$SO$_4$ (4.9 g, 50.00 mmol, 5.00 equiv). The resulting solution was allowed to react, with stirring, overnight while the temperature was maintained at reflux. The solution was extracted with 3×50 mL of ethyl acetate and the organic layers combined, dried over anhydrous sodium sulfate and concentrated under vacuum. The resulting solid material was washed with 3×3 mL of ethyl acetate. This resulted in 0.5 g (30%) of benzo[d][1,3]dioxol-5-ylboronic acid as a white solid.

Step 3. 3-(benzo[d][1,3]dioxol-5-yl)-2-phenylquinoxaline-6-carboxylic acid

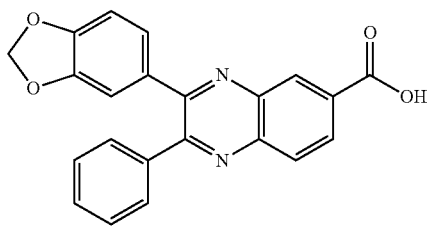 [SMILES: O=C(O)c1ccc2nc(-c3ccccc3)c(-c3ccc4c(c3)OCO4)nc2c1]

A suspension of methyl 3-bromo-2-phenylquinoxaline-6-carboxylate (80 mg, 0.23 mmol, 1.00 equiv), benzo[d][1,3]dioxol-4-ylboronic acid (59 mg, 0.36 mmol, 1.50 equiv), tricyclohexylphosphine (9 mg, 0.03 mmol, 0.14 equiv), Pd$_2$(dba)$_3$ (13 mg, 0.01 mmol, 0.06 equiv), and K$_3$PO$_4$ (149 mg, 0.80 mmol, 3.00 equiv). in dioxane/H$_2$O (1/0.5 mL) in a 10-mL sealed tube was allowed to react, with stifling, overnight at 95° C. The pH value of the solution was adjusted to 7 with HCl (1N). Purification via silica gel column (dichloromethane:methanol (1:10)) afforded 35 mg (40%) of 3-(benzo[d][1,3]dioxol-5-yl)-2-phenylquinoxaline-6-carboxylic acid as a yellow solid.

LC-MS (ES, m/z): [M+H]$^+$ calculated for C$_{22}$H$_{15}$N$_2$O$_5$: 371. Found: 371.

$^1$H-NMR (300 MHz, DMSO): δ 6.08 (2H, s), 6.91 (1H, d, J=8.1 Hz), 6.98 (1H, dd, J=1.8 Hz, 8.1 Hz), 7.01 (1H, d, J=1.5 Hz), 7.43 (2H, d, J=10.2 Hz), 7.56 (2H, dd, J=2.1 Hz, 7.2 Hz), 8.22 (1H, d, J=8.7 Hz), 8.30 (1H, dd, J=1.8 Hz, 8.7 Hz), 8.64 (1H, d, J=1.5 Hz).

EXAMPLE 21

2-Phenyl-3-(pyridin-4-yl)quinoxaline-6-carboxylic acid

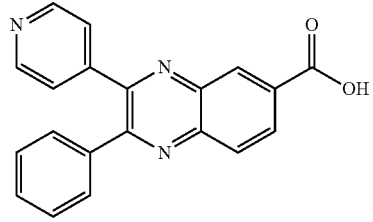 [SMILES: O=C(O)c1ccc2nc(-c3ccccc3)c(-c3ccncc3)nc2c1]

The product was obtained via a Suzuki coupling reaction using the method previously shown in Example 20, Step 3, with methyl 3-bromo-2-phenylquinoxaline-6-carboxylate (100 mg, 0.29 mmol, 1.00 equiv) and pyridin-4-yl boronic acid (54 mg, 0.44 mmol, 1.50 equiv) as reactants. Purification by Prep-TLC (silica gel) yielded 30 mg (30%) of 2-phenyl-3-(pyridin-4-yl)quinoxaline-6-carboxylic acid as a white solid.

LC-MS (ES, m/z): [M+H]+ calculated for C$_{20}$H$_{13}$N$_3$O$_2$: 328. Found: 328.

$^1$H-NMR (300 MHz, DMSO, ppm): δ 7.379-7.533 (7H, m), 8.175-8.198 (1H, m), 8.395 (1H, m), 8.592-8.649 (3H, m).

EXAMPLE 22

3-(4-Cyanophenyl)-2-phenylquinoxaline-6-carboxylic acid

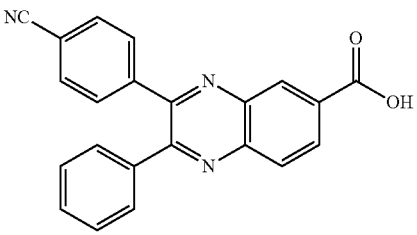 [SMILES: N#Cc1ccc(-c2nc3cc(C(=O)O)ccc3nc2-c2ccccc2)cc1]

Step 1. Methyl 3-(4-cyanophenyl)-2-phenylquinoxaline-6-carboxylate

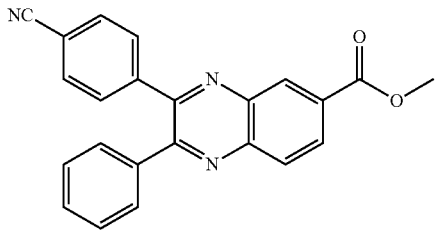 [SMILES: COC(=O)c1ccc2nc(-c3ccccc3)c(-c3ccc(C#N)cc3)nc2c1]

The ester product was obtained via a Suzuki coupling reaction using the method previously shown in Example 13, Step 6, with methyl 3-chloro-2-phenylquinoxaline-6-carboxylate (100 mg, 0.33 mmol, 1.00 equiv) and 4-cyanophenylboronic acid (74 mg, 0.50 mmol, 1.50 equiv) as reactants. Purification via silica gel column (ethyl acetate/petroleum ether (1:20 to 1:10)) afforded 90 mg (73%) of methyl 3-(4-cyanophenyl)-2-phenylquinoxaline-6-carboxylate as a yellow solid.

Step 2.
3-(4-cyanophenyl)-2-phenylquinoxaline-6-carboxylic acid

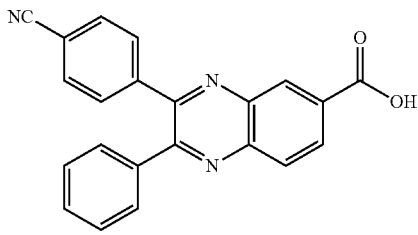 [SMILES: N#Cc1ccc(-c2nc3cc(C(=O)O)ccc3nc2-c2ccccc2)cc1]

A solution of methyl 3-cyano-2-phenylquinoxaline-6-carboxylate (50 mg, 0.17 mmol, 1.00 equiv) and NaOH (16 mg, 0.40 mmol, 3.00 equiv) in MeOH/H$_2$O (5/5 mL) in a 50-mL round-bottom flask was allowed to react, with stirring, for 1 hr at room temperature, followed by a further 1 hr at 50° C. in an oil bath. The reaction progress was monitored by TLC (ethyl acetate:petroleum ether (1:2)). The pH value of the solution was adjusted to 4 with 1N HCl, and the resulting mixture was concentrated under vacuum. The solids were collected by filtration and dried in an oven under reduced pressure, giving 30 mg (46%) of 3-(4-cyanophenyl)-2-phenylquinoxaline-6-carboxylic acid as a white solid.

LC-MS (ES, m/z) [M+H]+ calculated for C$_{22}$H$_{13}$N$_3$O$_2$: 352. Found: 352.

$^1$H-NMR (300 MHz, CDCl$_3$, ppm): δ 7.403-7.567 (5H, m), 7.669-7.735 (4H, m), 8.297-8.326 (1H, m), 8.484-8.518 (1H, m), 9.037 (1H, s).

EXAMPLE 23

3-(4-Methoxyphenyl)-2-phenylquinoxaline-6-carboxylic acid

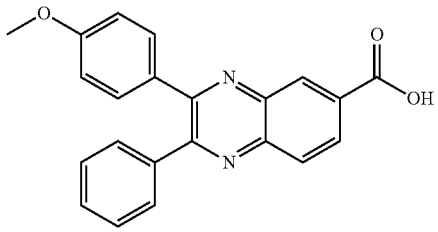

The product was obtained via a Suzuki coupling reaction using the method previously shown in Example 20, Step 3, with methyl 3-chloro-2-phenylquinoxaline-6-carboxylate (50 mg, 0.17 mmol, 1.00 equiv) and 4-methoxyphenylboronic acid (38 mg, 0.25 mmol, 1.50 equiv) as reactants. Purification via Prep-TLC (silica gel) yielded 25 mg (42%) of 3-(4-methoxyphenyl)-2-phenylquinoxaline-6-carboxylic acid as a yellow solid.

LC-MS (ES, m/z): [M+H]+ calculated for C$_{22}$H$_{16}$N$_2$O$_3$: 357. Found: 357.

$^1$H-NMR (300 MHz, DMSO, ppm): δ 3.790 (3H, s), 6.916-6.946 (2H, d, 9 Hz), 7.414-7.521 (7H, m), 7.998-8.027 (2H, d, 7.8 Hz), 8.332-8.359 (2H, d, 7.8 Hz), 8.537 (1H, s).

EXAMPLE 24

3-(Biphenyl-2-yl)-2-phenylquinoxaline-6-carboxylic acid

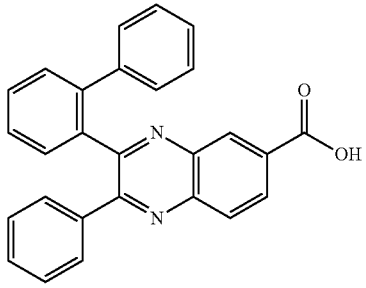 [SMILES: O=C(O)c1ccc2nc(-c3ccccc3)c(-c3ccccc3-c3ccccc3)nc2c1]

The product was obtained via a Suzuki coupling reaction using the method previously shown in Example 20, Step 3, with methyl 3-bromo-2-phenylquinoxaline-6-carboxylate (100 mg, 0.29 mmol, 1.00 equiv) and 2-diphenylboronic acid (87 mg, 0.44 mmol, 1.50 equiv) as reactants. Purification via Prep-TLC (dichloromethane:methanol (1:30)) afforded 48 mg (41%) of 3-(biphenyl-2-yl)-2-phenylquinoxaline-6-carboxylic acid as a white powder.

LC-MS (ES, m/z): [M+H]+ calculated for C$_{27}$H$_{19}$N$_2$O$_2$: 403. Found: 403.

$^1$H-NMR (300 MHz, DMSO): δ 6.38 (2H, d, J=7.5 Hz), 6.84 (2H, d, J=7.2 Hz), 6.97 (2H, t, J=7.8 Hz), 7.11 (3H, t, J=7.8 Hz), 7.28 (2H, t, J=6.9 Hz), 7.62 (2H, dd, J=6.9 Hz, 8.0 Hz), 7.90 (1H, dd, J=1.8 Hz, 5.7 Hz), 8.16 (1H, d, J=8.7 Hz), 8.31 (1H, dd, J=1.5 Hz, 9.3 Hz), 8.71 (1H, s).

EXAMPLE 25

2,3-Bis(4-fluorophenyl)-7-hydroxyquinoxaline-6-carboxylic acid

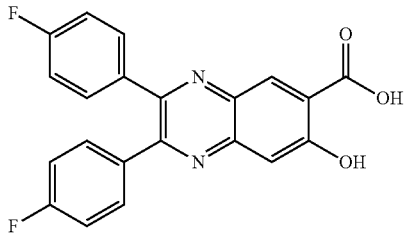 [SMILES: O=C(O)c1cc2nc(-c3ccc(F)cc3)c(-c3ccc(F)cc3)nc2cc1O]

Step 1. 4-acetamido-2-hydroxybenzoic acid

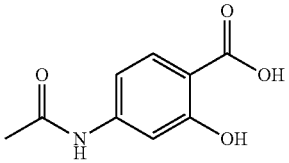

4-Amino-2-hydroxybenzoic acid (50 g, 3267 mmol, 1.00 equiv) was dissolved in H$_2$O (300 mL) and the pH was adjusted to 6 by addition of NaOH (10%). Ac2O (50 g, 490.20 mmol, 1.50 equiv) was added and the solution was allowed to react, with stirring, for 4 hr at 60° C. while the pH was maintained at 6-7 throughout the reaction by addition of 10% NaOH. Upon completion, the pH value of the solution was adjusted to 3-4 with concentrated HCl. The solids were collected by filtration, added to 200 mL of acetone, and stirred for 20 min. The solids were again collected by filtration, affording 61 g (91%) of 4-acetamido-2-hydroxybenzoic acid as a grey solid.

Step 2. 4-acetamido-2-hydroxy-5-nitrobenzoic acid

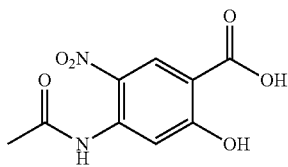 [SMILES: CC(=O)Nc1cc(O)c(C(=O)O)cc1[N+](=O)[O-]]

Nitric acid (fuming) (23.8 g, 378 mmol, 1.20 equiv) was added in portions under 50° C. to a mixture of 4-acetamido-2-hydroxybenzoic acid (61.4 g, 315 mmol, 1.00 equiv) and TFA (700 mL) in a 2-L round-bottom flask. The resulting solution was allowed to react, with stirring, for 3 hr at room temperature before being concentrated under vacuum. The residue was dissolved in 800 mL of acetone, stirred for 15 min. at reflux, then cooled. The solids were collected by filtration, giving 21.1 g (28%) of 4-acetamido-2-hydroxy-5-nitrobenzoic acid as an orange solid.

Step 3. 4-amino-2-hydroxy-5-nitrobenzoic acid

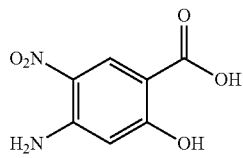 [SMILES: Nc1cc(O)c(C(=O)O)cc1[N+](=O)[O-]]

A mixture of 4-acetamido-2-hydroxy-5-nitrobenzoic acid (5 g, 20.8 mmol, 1.00 equiv) and HCl (aq.) (110 mL, 6N) in a 500-mL round-bottom flask was allowed to react, with stifling, for 2 hrs while the temperature was maintained at reflux. The mixture was cooled. The solids were collected by filtration, yielding 3.4 g (82%) of 4-amino-2-hydroxy-5-nitrobenzoic acid as a brown solid.

Step 4. 4,5-di(amino)-2-hydroxybenzoic acid

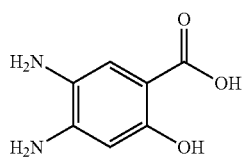 [SMILES: Nc1cc(O)c(C(=O)O)cc1N]

Under an $H_2(g)$ atmosphere, a suspension of 4-amino-2-hydroxy-5-nitrobenzoic acid (200 mg, 1.01 mmol, 1.00 equiv) and Pd/C (anhydrous) (0.1 g) in HOAc (15 mL) in a 50-mL round-bottom flask was allowed to react, with stirring, overnight at room temperature. The resulting solution was directly taken on to the next step without further purification.

Step 5. 1,2-bis(4-fluorophenyl)ethanone

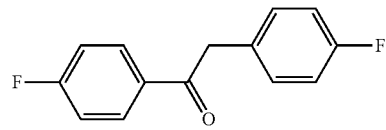 [SMILES: O=C(Cc1ccc(F)cc1)c1ccc(F)cc1]

A solution of 2-(4-fluorophenyl)acetic acid (5.0 g, 32.5 mmol, 1.00 equiv) in $SOCl_2$ (30 mL) was heated for 3 hr at reflux in a 50-mL round-bottom flask. Most of $SOCl_2$ was removed under vacuum, and the residue was added dropwise into a solution of $AlCl_3$ (12.8 g, 96.2 mmol, 3.00 equiv) and fluorobenzene (6.1 g, 63.54 mmol, 2.00 equiv) in DCM (20 mL) at 0° C. The resulting solution was allowed to react, with stirring, for 2 hrs at room temperature.

Step 6. 1,2-bis(4-fluorophenyl)ethane-1,2-dione

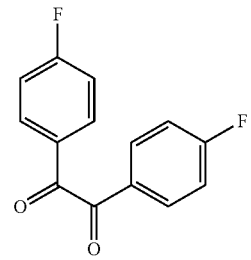 [SMILES: O=C(C(=O)c1ccc(F)cc1)c1ccc(F)cc1]

$SeO_2$ (191 mg, 1.72 mmol, 4.00 equiv) was added in batches to a solution of 1,2-bis(4-fluorophenyl)ethanone (100 mg, 0.43 mmol, 1.00 equiv) in DMSO (4.5 mL). The resulting solution was allowed to react, with stirring, for 2 hrs while the temperature was maintained at 100° C. in an oil bath. The solids were filtered out and discarded.

Step 7. 2,3-bis(4-fluorophenyl)-7-hydroxyquinoxaline-6-carboxylic acid

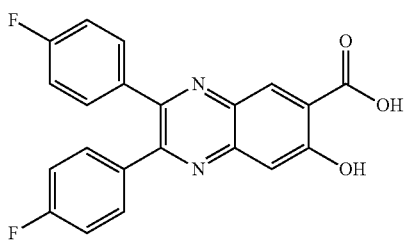 [SMILES: O=C(O)c1cc2nc(-c3ccc(F)cc3)c(-c3ccc(F)cc3)nc2cc1O]

A mixture of 1,2-bis(4-fluorophenyl)ethane-1,2-dione (175 mg, 0.71 mmol, 1.00 equiv) and 4,5-diamino-2-hydroxybenzoic acid (120 mg, 0.71 mmol, 1.00 equiv) in HOAc (3 mL) was allowed to react, with stifling, for 3 hrs while the temperature was maintained at 130° C. in an oil bath. The reaction solution was poured into 10 ml of $H_2O$. The resulting solid was filtered and purified by prep-HPLC, yielding 50 mg (19%) of 2,3-bis(4-fluorophenyl)-7-hydroxyquinoxaline-6-carboxylic acid as a yellow solid.

LC-MS (ES, m/z): [M+H]+ calculated for $C_{21}H_{13}F_2N_2O_3$: 379. Found: 379.

¹H-NMR (300 MHz, DMSO, ppm): δ 7.203-7.270 (4H, m), 7.476-7.553 (5H, m), 8.555 (1H, s).

EXAMPLE 26

2,3-Bis(4-chlorophenyl)-7-hydroxyquinoxaline-6-carboxylic acid

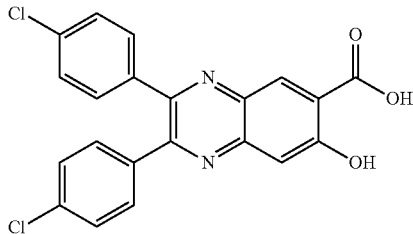 [SMILES: O=C(O)c1cc2nc(-c3ccc(Cl)cc3)c(-c3ccc(Cl)cc3)nc2cc1O]

Step 1. 1,2-bis(4-chlorophenyl)ethanone

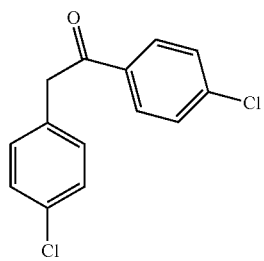 [SMILES: O=C(Cc1ccc(Cl)cc1)c1ccc(Cl)cc1]

The diaryl product was obtained using the same synthetic methods as shown in Example 25, step 5, using 2-(4-chlorophenyl)acetic acid (5 g, 29.2 mmol) and chlorobenzene (10.31 g, 91.2 mmol, 2.85 equiv) as reactants. The reaction was quenched by the addition of water/ice. The residue was dissolved in 3% HCl, extracted with 3×20 mL of dichloromethane, and the organic layers combined and concentrated under vacuum. Purification via silica gel column (ethyl acetate/petroleum ether (1:100)) yielded 4.63 g (54%) of 1,2-bis(4-chlorophenyl)ethanone as a white solid.

Step 2. 1,2-bis(4-chlorophenyl)ethane-1,2-dione

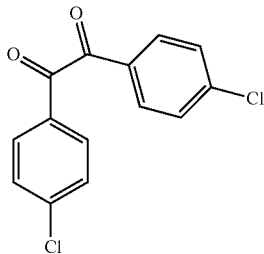 [SMILES: O=C(C(=O)c1ccc(Cl)cc1)c1ccc(Cl)cc1]

The dione product was obtained using the same synthetic methods as shown in Example 25, step 6, using 1,2-bis(4-chlorophenyl)ethanone (2.12 g, 8.00 mmol, 1.00 equiv) and SeO₂ (5.11 g, 46.0 mmol, 5.75 equiv) as reactants. The solution was allowed to react, with stifling, for 2 hr at 120° C., then diluted with ethyl acetate, washed with saturated aqueous NaCl, and concentrated under vacuum. This afforded 2.19 g (crude) of 1,2-bis(4-chlorophenyl)ethane-1,2-dione as a yellow solid.

Step 3. 2,3-bis(4-chlorophenyl)-7-hydroxyquinoxaline-6-carboxylic acid

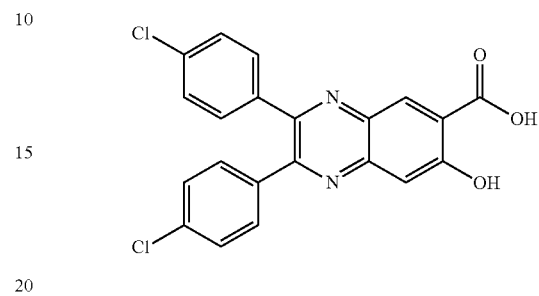

The diaryl product was obtained using the same synthetic methods as shown in Example 25, step 7, using 4,5-diamino-2-hydroxybenzoic acid (60 mg, 0.36 mmol, 1.00 equiv) and 1,2-bis(4-chlorophenyl)ethane-1,2-dione (100 mg, 0.36 mmol, 1.00 equiv) as reactants. This afforded 30 mg (20%) of 2,3-bis(4-chlorophenyl)-7-hydroxyquinoxaline-6-carboxylic acid as a yellow solid.

LC-MS (ES, m/z): [M+H]+ calculated for $C_{21}H_{13}Cl_2N_2O_3$: 412. Found: 412.

¹H-NMR (300 MHz, DMSO, ppm): δ 7.479-7.529 (9H, m), 8.558 (1H, s).

EXAMPLE 27

7-Hydroxy-2,3-bis(4-methoxyphenyl)quinoxaline-6-carboxylic acid

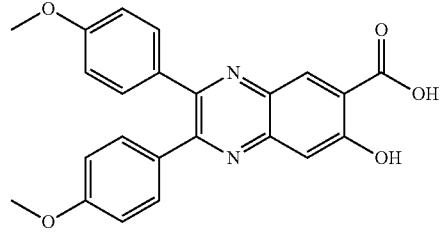 [SMILES: COc1ccc(-c2nc3cc(O)c(C(=O)O)cc3nc2-c2ccc(OC)cc2)cc1]

Step 1. 1,2-bis(4-methoxyphenyl)ethanone

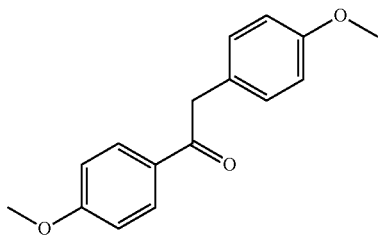

The diaryl product was obtained using the same synthetic methods as shown in Example 25, step 5, using 2-(4-methoxyphenyl)acetic acid (5.0 g, 30.1 mmol, 1.00 equiv) and anisole (16 g, 148.1 mmol, 5.00 equiv) as reactants. Purification via silica gel column (ethyl acetate/petroleum ether (1:10)) afforded 4.0 g (52%) of 1,2-bis(4-methoxyphenyl) ethanone as a white solid.

Step 2. 1,2-bis(4-methoxyphenyl)ethane-1,2-dione

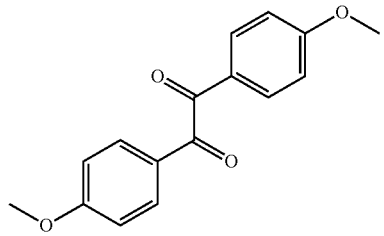

The dione product was obtained using the same synthetic methods as shown in Example 25, step 6, using 1,2-bis(4-methoxyphenyl)ethanone as a reactant. The reaction was quenched by the addition of 100 mL of water. The solids were collected by filtration and dried in a vacuum oven to afford 1.1 g (58%) of 1,2-bis(4-methoxyphenyl)ethane-1,2-dione as a yellow solid.

Step 3. 7-hydroxy-2,3-bis(4-methoxyphenyl)quinoxaline-6-carboxylic acid

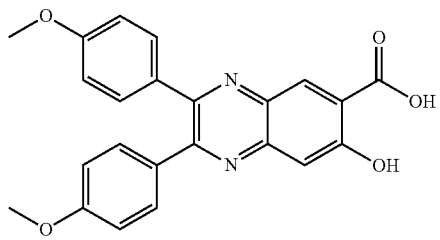 [SMILES: COc1ccc(-c2nc3cc(O)c(C(=O)O)cc3nc2-c2ccc(OC)cc2)cc1]

The diaryl product was obtained using the same synthetic methods as shown in Example 25, step 7, using 4,5-diamino-2-hydroxybenzoic acid (168 mg, 1.00 mmol, 1.00 equiv) and 1,2-bis(4-methoxyphenyl)ethane-1,2-dione (270 mg, 1.00 mmol, 1.00 equiv) as reactants, yielding 50 mg (12%) of 7-hydroxy-2,3-bis(4-methoxyphenyl)quinoxaline-6-carboxylic acid as a red solid.

EXAMPLE 28

7-Hydroxy-2,3-bis(4-hydroxyphenyl)quinoxaline-6-carboxylic acid

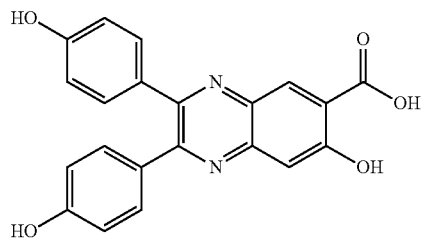 [SMILES: O=C(O)c1cc2nc(-c3ccc(O)cc3)c(-c3ccc(O)cc3)nc2cc1O]

BBr$_3$ (1.26 g, 5.02 mmol, 10.00 equiv) was added dropwise with stifling at 0° C. to a solution of 7-hydroxy-2,3-bis(4-methoxyphenyl)quinoxaline-6-carboxylic acid (200 mg, 0.50 mmol, 1.00 equiv) in DCM (20 mL) in a 50-mL round-bottom flask. The resulting solution was allowed to react, with stirring, overnight at room temperature. The reaction was quenched by the addition of 10 mL of 1N (aq) NaOH. The pH of the solution was adjusted to 3-4 with HCl (1M). The solution was extracted with 2×100 mL of CH$_2$Cl$_2$: MeOH (10:1), and the organic layers combined and concentrated under vacuum, yielding 120 mg (64%) of 7-hydroxy-2,3-bis(4-hydroxyphenyl)quinoxaline-6-carboxylic acid as a red solid.

LC-MS: (ES, m/z): [M+H]+ calculated for C$_{21}$H$_{15}$N$_2$O$_5$: 375. Found: 375.

$^1$H-NMR (300 MHz, DMSO, ppm): δ 6.767-6.795 (4H, m), 7.322-7.389 (4H, m), 7.436 (1H, s), 8.677 (1H, s).

EXAMPLE 29

7-Hydroxy-2,3-bis(3-hydroxyphenyl)quinoxaline-6-carboxylic acid

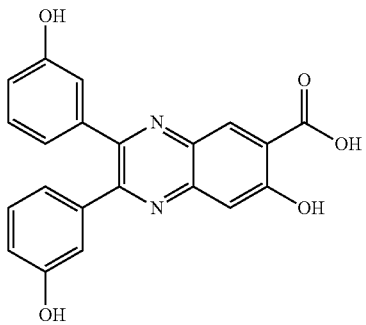 [SMILES: O=C(O)c1cc2nc(-c3cccc(O)c3)c(-c3cccc(O)c3)nc2cc1O]

Step 1. Methyl 3-methoxybenzoate

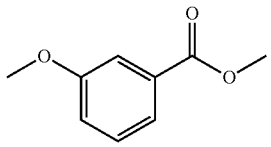

A solution of 3-methoxybenzoic acid (20 g, 131.58 mmol, 1.00 equiv) in MeOH (100 mL) and H$_2$SO$_4$ (13 g, 130.00 mmol, 1.00 equiv, 98%) was allowed to react, with stirring in a 250-mL round-bottom flask, overnight under reflux. The reaction was quenched by the addition of 100 mL of water/ice, extracted with 3×100 mL of dichloromethane, and the organic layers combined and dried over anhydrous sodium sulfate. The solids were filtered out. The resulting mixture was concentrated under vacuum yielding 21 g (96%) of methyl 3-methoxybenzoate as yellow oil.

Step 2.
2-hydroxy-1,2-bis(3-methoxyphenyl)ethanone

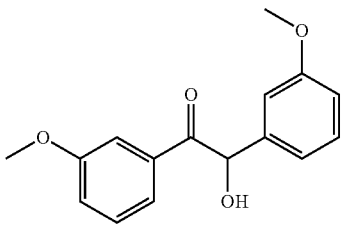 [SMILES: COc1cccc(C(=O)C(O)c2cccc(OC)c2)c1]

To a solution of naphthalene (12.4 g, 96.88 mmol, 3.23 equiv) in THF (100 mL) at −10° C. under an inert atmosphere was added Li (630 mg, 90.00 mmol, 3.00 equiv), and the resulting solution was allowed to react, with stifling, overnight at room temperature. Upon cooling to −78° C. a solution of methyl 3-methoxybenzoate (5 g, 30.12 mmol, 1.00 equiv) in THF (20 mL) was added and allowed to react, with stifling, for an additional 1 hr at room temperature. The reaction was quenched by 6.5 g of Me₃SiCl at 0° C. and stirred for 30 min. at room temperature. After further cooling to 0° C., 30 ml of H₂O was added dropwise, then extracted by ethyl acetate (100 mL for 3 times). The organic layers were concentrated and purified by column chromatography (petroleum ether: ethyl acetate 10:1) affording 3.5 g (43%) of 2-hydroxy-1,2-bis(3-methoxyphenyl)ethanone as a yellow solid.

Step 3. 1,2-bis(3-methoxyphenyl)-1,2-ethandione

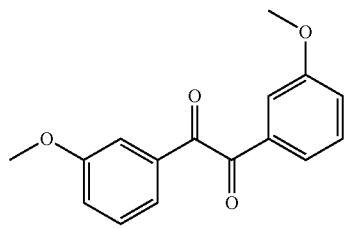 [SMILES: COc1cccc(C(=O)C(=O)c2cccc(OC)c2)c1]

A solution of 2-hydroxy-1,2-bis(3-methoxyphenyl)ethanone (3.5 g, 12.87 mmol, 1.00 equiv), NH₄NO₃ (1.04 g, 13.00 mmol, 1.00 equiv), and Cu(OAc)₂.H₂O (260 mg, 1.30 mmol, 0.10 equiv) in 80% aqueous HOAc (30 mL) was allowed to react, with stirring, for 2 hrs while the temperature was maintained at reflux in an oil bath. Upon cooling to 0° C., the solid was filtered and washed with H₂O (3×30 ml), affording 2.5 g (72%) of 1,2-bis(3-methoxyphenyl)-1,2-ethandione as a yellow solid.

Step 4. 7-hydroxy-2,3-bis(3-methoxyphenyl)quinoxaline-6-carboxylic acid

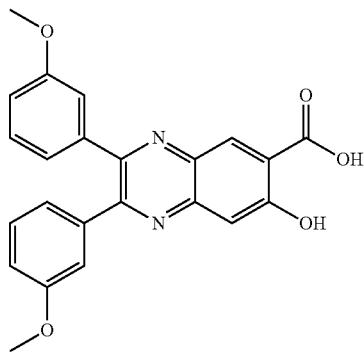 [SMILES: COc1cccc(-c2nc3cc(O)c(C(=O)O)cc3nc2-c2cccc(OC)c2)c1]

The diaryl product was obtained using the same synthetic methods as shown in Example 25, step 7, using 4,5-diamino-2-hydroxybenzoic acid (168 mg, 1.00 mmol, 1.00 equiv) and 1,2-bis(3-methoxyphenyl)-1,2-ethandione (270 mg, 1.00 mmol, 1.00 equiv) as reactants. This resulted in 250 mg (62%) of 7-hydroxy-2,3-bis(3-methoxyphenyl)quinoxaline-6-carboxylic acid as a yellow solid.

Step 5. 7-hydroxy-2,3-bis(3-hydroxyphenyl)quinoxaline-6-carboxylic acid

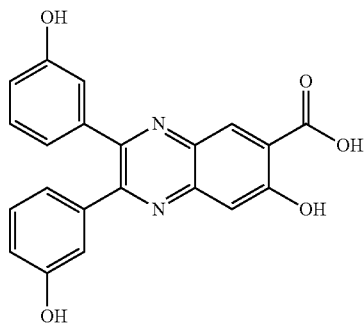 [SMILES: O=C(O)c1cc2nc(-c3cccc(O)c3)c(-c3cccc(O)c3)nc2cc1O]

The bis-phenol product was obtained using the same synthetic methods as shown in Example 28, using 7-hydroxy-2,3-bis(3-methoxyphenyl)quinoxaline-6-carboxylic acid (200 mg, 0.50 mmol, 1.00 equiv) as the reactant. This resulted in 80 mg (43%) of 7-hydroxy-2,3-bis(3-hydroxyphenyl)quinoxaline-6-carboxylic acid as a red solid.

LC-MS (ES, m/z): calculated for C₂₁H₁₄N₂O₅: 374. Found: 375 [M+H]+

¹H-NMR (300 MHz, DMSO, ppm): δ 6.815-6.940 (4H, m), 6.992-7.015 (2H, m), 7.7.144-7.204 (2H, m), 7.505 (1H, s), 8.750 (1H, s).

EXAMPLE 30

3-(4-Chlorophenyl)-2-phenylquinoxaline-6-carboxylic acid

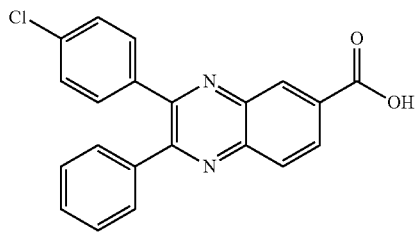 [SMILES: O=C(O)c1ccc2nc(-c3ccccc3)c(-c3ccc(Cl)cc3)nc2c1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and 4-chlorophenylboronic acid (87 mg, 0.56 mmol, 1.50 equiv) as reactants. Purification via silica gel column (dichloromethane/methanol (5:1)) afforded 43 mg (37%) of 3-(4-chlorophenyl)-2-phenylquinoxaline-6-carboxylic acid as a light yellow solid.

LC-MS (ES, m/z) [M+H]+ calculated for C₂₁H₁₃ClN₂O₂: 361. Found: 361.

¹H-NMR (300 MHz, DMSO, ppm): δ 13.571 (1H, s), 8.675 (1H, s), 8.670-7.396 (9H, m).

EXAMPLE 31

3-(4-Bromophenyl)-2-phenylquinoxaline-6-carboxylic acid

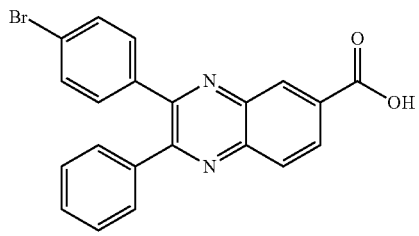

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and 4-bromophenylboronic acid (67.9 mg, 0.34 mmol, 1.50 equiv) as reactants. Purification via silica gel column (dichloromethane/methanol (5:1)) yielded 14 mg (10%) of 3-(4-bromophenyl)-2-phenylquinoxaline-6-carboxylic acid as a light yellow solid.

LC-MS (ES, m/z): [M+H]+ calculated for $C_{21}H_{13}BrN_2O_2$: 405. Found: 405.

$^1$H-NMR (300 MHz, DMSO, ppm): δ 8.674-8.669 (1H, d, 1.5 Hz), 8.363-8.329 (1H, t, 8.7 Hz), 8.261-8.232 (1H, d, 8.7 Hz), 7.622-7.388 (9H, m).

EXAMPLE 32

3-(4-Ethylphenyl)-2-phenylquinoxaline-6-carboxylic acid

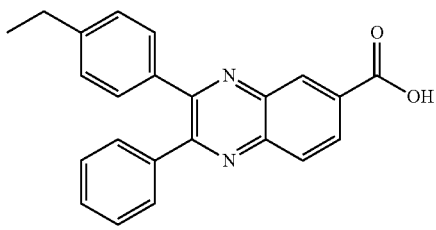 [SMILES: CCc1ccc(-c2nc3cc(C(=O)O)ccc3nc2-c2ccccc2)cc1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and 4-ethylphenylboronic acid (62.3 mg, 0.42 mmol, 1.50 equiv) as reactants. Purification via silica gel column (dichloromethane/methanol (5:1)) yielded 52 mg (49%) of 3-(4-ethylphenyl)-2-phenylquinoxaline-6-carboxylic acid as a white solid.

LC-MS (ES, m/z) [M+H]$^+$ calculated for $C_{21}H_{13}FN_2O_2$: 355. Found: 355.

$^1$H-NMR (300 MHz, DMSO, ppm): δ 8.647 (1H, s), 8.335-8.303 (1H, d, 9.6 Hz), 8.234-8.205 (1H, d, 8.7 Hz), 7.537-7.511 (2H, t), 7.448-7.364 (5H, m), 7.236-7.209 (2H, d, 8.1 Hz), 2.677-2.601 (2H, d, 15 Hz), 1.221-1.171 (3H, t).

EXAMPLE 33

3-(4-tert-Butylphenyl)-2-phenylquinoxaline-6-carboxylic acid

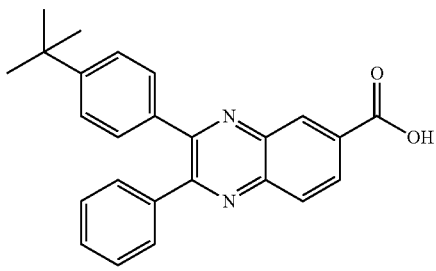 [SMILES: CC(C)(C)c1ccc(-c2nc3cc(C(=O)O)ccc3nc2-c2ccccc2)cc1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and 4-tert-butylphenylboronic acid (83 mg, 0.47 mmol, 1.50 equiv) as reactants. Purification via prep-TLC resulted in 30 mg (27%) of 3-(4-tert-butylphenyl)-2-phenylquinoxaline-6-carboxylic acid as a white solid.

LC-MS (ES, m/z): [M+H]+ calculated for $C_{25}H_{22}N_2O_2$: 383. Found: 383.

$^1$H-NMR (300 MHz, DMSO, ppm): δ 1.242-1.296 (9H, s), 7.360-7.526 (9H, m), 8.057-8.086 (1H, d, 8.7 Hz), 8.331-8.359 (1H, d, 8.4 Hz), 8.564 (1H, s).

EXAMPLE 34

3-(4-(Hydroxymethyl)phenyl)-2-phenylquinoxaline-6-carboxylic acid

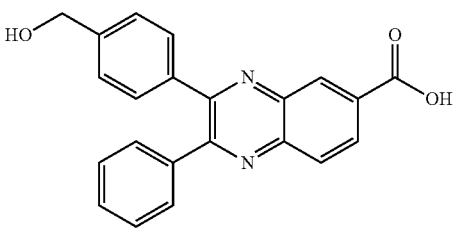 [SMILES: O=C(O)c1ccc2nc(-c3ccccc3)c(-c3ccc(CO)cc3)nc2c1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and 4-(hydroxymethyl)phenylboronic acid (66.12 mg, 0.43 mmol, 1.50 equiv) as reactants. Purification via silica gel column (dichloromethane/methanol (10:1)) afforded 80 mg (76%) of 3-(4-(hydroxymethyl)phenyl)-2-phenylquinoxaline-6-carboxylic acid as a light yellow solid.

LC-MS (ES, m/z): [M+H]$^+$ calculated for $C_{22}H_{16}N_2O_3$: 357. Found: 357.

$^1$H-NMR (300 MHz, DMSO, ppm): δ 8.594 (1H, s), 8.374-8.346 (1H, d, 8.4 Hz), 8.099-8.071 (1H, d, 8.4 Hz), 7.517-7.378 (7H, m), 8.320-7.293 (2H, d, 8.1 Hz), 4.535 (2H, s).

EXAMPLE 35

3-(4-Carboxyphenyl)-2-phenylquinoxaline-6-carboxylic acid

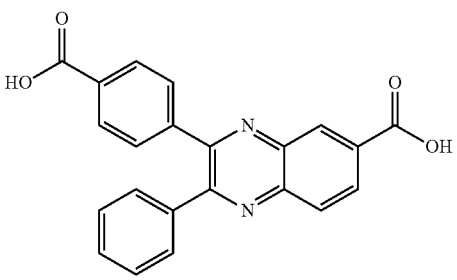 [SMILES: O=C(O)c1ccc(-c2nc3cc(C(=O)O)ccc3nc2-c2ccccc2)cc1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and 4-carboxyphenylboronic acid (73 mg, 0.44 mmol, 1.50 equiv) as reactants. Purification by prep-TLC yielded 21 mg (19%) of 3-(4-carboxyphenyl)-2-phenylquinoxaline-6-carboxylic acid as a white solid.

LC-MS (ES, m/z): [M+H]+ calculated for $C_{22}H_{15}N_2O_4$: 371. Found: 371.

¹H-NMR (300 MHz, DMSO, ppm): δ 7.376-7.533 (5H, m), 7.617-7.644 (2H, m), 7.922-7.949 (2H, m), 8.257-8.286 (1H, m), 8.338-8.372 (1H, m), 8.691 (1H, s), 13.340 (2H, s).

EXAMPLE 36

2-Phenyl-3-(4-(trifluoromethoxy)phenyl)quinoxaline-6-carboxylic acid

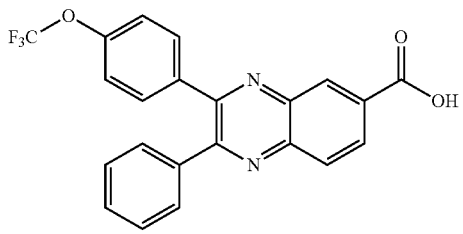 [SMILES: O=C(O)c1ccc2nc(-c3ccccc3)c(-c3ccc(OC(F)(F)F)cc3)nc2c1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and 4-(trifluoromethoxy) phenylboronic acid (89.6 mg, 0.43 mmol, 1.50 equiv) as reactants. Purification via silica gel column (dichloromethane/methanol (10:1)) yielded 57 mg (47%) of 2-phenyl-3-(4-(trifluoromethoxy)phenyl)quinoxaline-6-carboxylic acid as a white solid.

LC-MS (ES, m/z): [M+H]+ calculated. for $C_{22}H_{13}F_3N_2O_3$: 411. Found: 411.

¹H-NMR (300 MHz, DMSO, ppm): δ 8.635 (1H, s), 8.395-8.367 (1H, d, 8.4 Hz), 8.168-8.140 (1H, d, 8.4 Hz), 7.641-7.612 (2H, d, 8.7 Hz), 7.522-7.496 (2H, d, 7.8 Hz), 7.441-7.373 (5H, m).

EXAMPLE 37

2-Phenyl-3-(3-(trifluoromethoxy)phenyl)quinoxaline-6-carboxylic acid

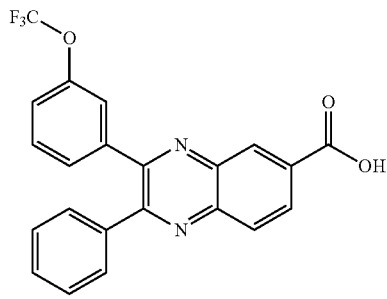 [SMILES: O=C(O)c1ccc2nc(-c3ccccc3)c(-c3cccc(OC(F)(F)F)c3)nc2c1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and 3-(trifluoromethoxy) phenylboronic acid (89.6 mg, 0.43 mmol, 1.50 equiv) as reactants. Purification via silica gel column (dichloromethane/methanol (10:1)) afforded 67 mg (55%) of 2-phenyl-3-(3-(trifluoromethoxy)phenyl)quinoxaline-6-carboxylic acid as a white solid.

LC-MS (ES, m/z): [M+H]+ calculated for $C_{22}H_{13}F_3N_2O_3$: 411. Found: 411.

¹H-NMR (300 MHz, DMSO, ppm): δ 8.637 (1H, s), 8.414-8.386 (1H, d, 8.4 Hz), 8.134-8.105 (1H, d, 8.7 Hz), 7.628-7.363 (9H, m).

EXAMPLE 38

3-(3-Fluorophenyl)-2-phenylquinoxaline-6-carboxylic acid

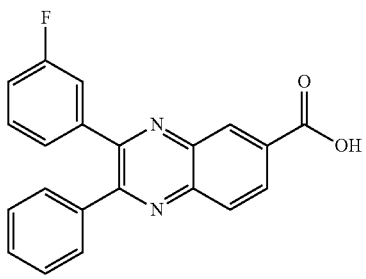 [SMILES: O=C(O)c1ccc2nc(-c3ccccc3)c(-c3cccc(F)c3)nc2c1]

The product was obtained via a Suzuki coupling reaction using the method previously shown in Example 20, Step 3, using methyl 3-chloro-2-phenylquinoxaline-6-carboxylate (90 mg, 0.30 mmol, 1.00 equiv) and 3-fluorophenylboronic acid (63.4 mg, 0.45 mmol, 1.50 equiv) as reactants. Purification via silica gel column (dichloromethane/methanol (10:1)) yielded 60 mg (55%) of 3-(3-fluorophenyl)-2-phenylquinoxaline-6-carboxylic acid as a light yellow solid.

LC-MS (ES, m/z): [M+H]+ calculated for $C_{21}H_{13}FN_2O_2$: 345. Found: 345.

¹H-NMR (300 MHz, DMSO, ppm): δ 8.615 (1H, s), 8.348-8.327 (1H, d, 6.3 Hz), 8.121-8.098 (1H, d, 6.9 Hz), 7.596-7.491 (8H, t), 7.164 (1H, s).

EXAMPLE 39

2-Phenyl-3-o-tolylquinoxaline-6-carboxylic acid

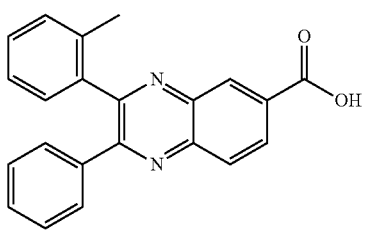 [SMILES: Cc1ccccc1-c1nc2cc(C(=O)O)ccc2nc1-c1ccccc1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and o-tolylboronic acid (78.9 mg, 0.58 mmol, 2.00 equiv) as reactants. Purification via silica gel column (dichloromethane/methanol (10:1)) afforded 85 mg (84%) of 2-phenyl-3-o-tolylquinoxaline-6-carboxylic acid as a white solid.

LC-MS (ES, m/z): [M+H]+ calculated for $C_{19}H_{12}N_2O_2S$: 341. Found: 341.

$^1$H-NMR (300 MHz, CD$_3$OD, ppm): δ 8.749 (1H, s), 8.442-8.412 (1H, d, J=9 Hz), 8.208-8.180 (1H, d, J=8.4 Hz), 7.871 (1H, s), 7.506-7.478 (2H, t), 7.360-7.190 (7H, m), 1.996 (3H, s).

EXAMPLE 40

2-Phenyl-3-m-tolylquinoxaline-6-carboxylic acid

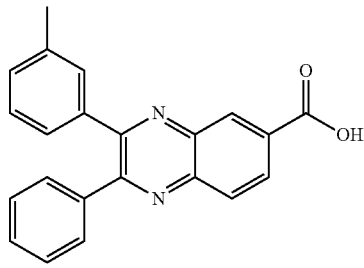 [SMILES: Cc1cccc(-c2nc3cc(C(=O)O)ccc3nc2-c2ccccc2)c1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and m-tolylboronic acid (78.9 mg, 0.58 mmol, 2.00 equiv) as reactants. Purification via silica gel column (dichloromethane/methanol (10:1)) yielded 35 mg (35%) of 2-phenyl-3-m-tolylquinoxaline-6-carboxylic acid as a light yellow solid.

LC-MS (ES, m/z): [M+H]+ calculated for C$_{19}$H$_{12}$N$_2$O$_2$S: 341. Found: 341.

$^1$H-NMR (300 MHz, CD$_3$OD, ppm): δ 8.790 (1H, s), 8.423-8.394 (1H, d, J=8.7 Hz), 8.175-8.148 (1H, d, J=8.1 Hz), 7.867 (1H, s), 7.535-7.512 (2H, d, J=6.9 Hz), 7.430-7.348 (4H, m), 7.232 (3H, d), 2.322 (3H, s).

EXAMPLE 41

3-(4-Nitrophenyl)-2-phenylquinoxaline-6-carboxylic acid

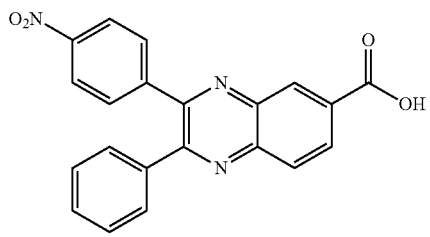 [SMILES: O=C(O)c1ccc2nc(-c3ccccc3)c(-c3ccc([N+](=O)[O-])cc3)nc2c1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and 4,4,5,5-tetramethyl-2-(4-nitrophenyl)-1,3,2-dioxaborolane (144.4 mg, 0.58 mmol, 2.00 equiv) as reactants. Purification via silica gel column (dichloromethane/methanol (10:1)) afforded 27 mg (24%) of 3-(4-nitrophenyl)-2-phenylquinoxaline-6-carboxylic acid as a yellow solid.

LC-MS (ES, m/z): [M+H]+ calculated for C$_{19}$H$_{12}$N$_2$O$_2$S: 372. Found: 372.

$^1$H-NMR (300 MHz, CDCl$_3$, ppm): δ 8.813 (1H, s), 8.468-8.441 (1H, d, J=8.1 Hz), 8.250-8.190 (3H, t), 7.800-7.771 (2H, d, J=8.7 Hz), 7.561-7.539 (2H, d, J=6.6 Hz), 7.470-7.411 (3H, m).

EXAMPLE 42

3-(Furan-3-yl)-2-phenylquinoxaline-6-carboxylic acid

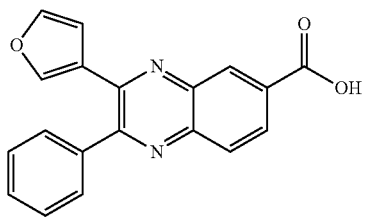 [SMILES: O=C(O)c1ccc2nc(-c3ccccc3)c(-c3ccoc3)nc2c1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and furan-3-yl boronic acid (48.8 mg, 0.44 mmol, 1.50 equiv) as reactants. Purification via silica gel column (dichloromethane/methanol (10:1)) yielded 23 mg (24%) of 3-(furan-3-yl)-2-phenylquinoxaline-6-carboxylic acid as a white solid.

LC-MS (ES, m/z): [M+H]$^+$ calculated for C$_{19}$H$_{12}$N$_2$O$_3$: 317. Found: 317.

$^1$H-NMR (300 MHz, DMSO, ppm): δ 8.581 (1H, s), 8.324-8.294 (1H, d, 9 Hz), 8.081-8.052 (1H, d, 8.7 Hz), 7.708 (1H, s), 7.598-7.567 (5H, t), 7.318 (1H, s), 6.662 (2H, s), 2.677-2.601 (2H, d, 15 Hz), 1.221-1.171 (3H, t).

EXAMPLE 43

2-Phenyl-3-(thiophen-3-yl)quinoxaline-6-carboxylic acid

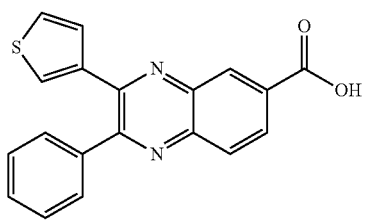 [SMILES: O=C(O)c1ccc2nc(-c3ccccc3)c(-c3ccsc3)nc2c1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and thiophen-3-ylboronic acid (55.7 mg, 0.44 mmol, 1.50 equiv) as reactants. Purification via silica gel column (dichloromethane/methanol (10:1)) afforded 40 mg (39%) of 2-phenyl-3-(thiophen-3-yl)quinoxaline-6-carboxylic acid as a white solid.

LC-MS (ES, m/z): [M+H]+ calculated for C$_{19}$H$_{12}$N$_2$O$_2$S: 333. Found: 333.

$^1$H-NMR (300 MHz, DMSO, ppm): δ 8.628 (1H, s), 8.389 (1H, s), 8.134 (1H, s), 7.510-7.317 (8H, t).

EXAMPLE 44

3-(4-Hydroxyphenyl)-2-phenylquinoxaline-6-carboxylic acid

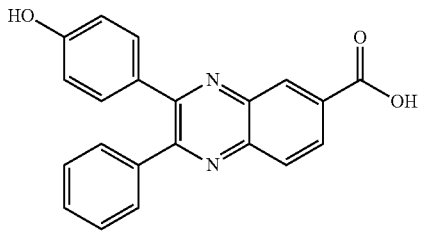 [SMILES: O=C(O)c1ccc2nc(-c3ccccc3)c(-c3ccc(O)cc3)nc2c1]

Step 1. 3-(4-methoxyphenyl)-2-phenylquinoxaline-6-carboxylic acid

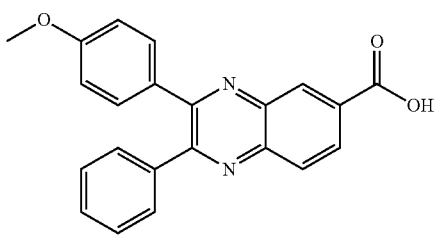 [SMILES: COc1ccc(-c2nc3cc(C(=O)O)ccc3nc2-c2ccccc2)cc1]

The product was obtained via a Suzuki coupling reaction using the method previously shown in Example 20, Step 3, using methyl 3-bromo-2-phenylquinoxaline-6-carboxylate (150 mg, 0.44 mmol, 1.00 equiv) and 4-methoxyphenylboronic acid (100 mg, 0.66 mmol, 1.50 equiv) as reactants. Purification via silica gel column (dichloromethane/methanol (10:1)) yielded 105 mg (65%) of 3-(4-methoxyphenyl)-2-phenylquinoxaline-6-carboxylic acid as a yellow solid.

LC-MS (ES, m/z): [M+H]+ calculated for $C_{22}H_{16}N_2O_3$: 357. Found: 357.

Step 2. 3-(4-Hydroxyphenyl)-2-phenylquinoxaline-6-carboxylic acid

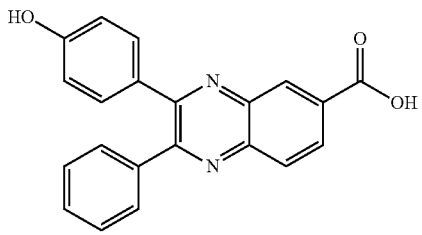 [SMILES: O=C(O)c1ccc2nc(-c3ccccc3)c(-c3ccc(O)cc3)nc2c1]

The product was obtained via the method previously shown in Example 28, using 3-(4-methoxyphenyl)-2-phenylquinoxaline-6-carboxylic acid (105 mg, 0.29 mmol, 1.00 equiv, 99%) as the reactant. Extraction with 4×40 mL of dichloromethane, followed by concentration of the organic layers and purification via silica gel column (dichloromethane/methanol (10:1)) afforded 26 mg (25%) of 3-(4-hydroxyphenyl)-2-phenylquinoxaline-6-carboxylic acid as a yellow solid.

LC-MS (ES, m/z): [M+H]+ calculated for $C_{21}H_{14}N_2O_3$: 343. Found: 343.

$^1$H-NMR (300 MHz, MeOD, ppm) δ: 8.785, 8.780 (1H, d, J=1.5 Hz), 8.374-8.368 (1H, d, J=1.8 Hz), 8.345-8.339 (1H, d, J=1.8 Hz), 8.188-8.159 (2H, d, J=8.7 Hz), 7.571-7.367 (5H, m), 6.777-6.748 (2H, d, J=8.7 Hz).

EXAMPLE 45

3-(2,4-Dimethoxyphenyl)-2-phenylquinoxaline-6-carboxylic acid

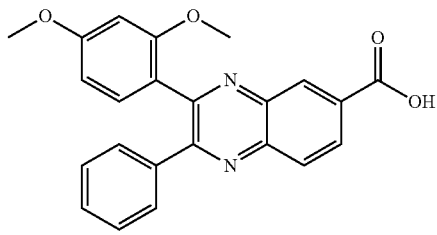 [SMILES: COc1ccc(-c2nc3cc(C(=O)O)ccc3nc2-c2ccccc2)c(OC)c1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and 2,4-dimethoxyphenylboronic acid (103.7 mg, 0.57 mmol, 1.50 equiv) as reactants. Purification via silica gel column (dichloromethane/methanol (10:1)) afforded 21 mg (18%) of 3-(2,4-dimethoxyphenyl)-2-phenylquinoxaline-6-carboxylic acid as a yellow solid.

LC-MS (ES, m/z): [M+H]+ calculated for $C_{23}H_{18}N_2O_4$: 387. Found: 387.

$^1$H-NMR (300 MHz, DMSO, ppm) δ: 8.591 (1H, s), 8.352-8.325 (1H, d, J=8.1 Hz), 8.132-8.104 (1H, d, J=8.4 Hz), 7.604-7.577 (1H, d, J=8.1 Hz), 7.474-7.450 (2H, d, J=7.2 Hz), 7.358-7.335 (3H, d, J=6.9 Hz), 6.750-6.723 (1H, d, J=8.1 Hz), 6.418 (1H, s), 3.816 (3H, s), 3.155 (3H, s).

EXAMPLE 46

3-(3-Hydroxyphenyl)-2-phenylquinoxaline-6-carboxylic acid

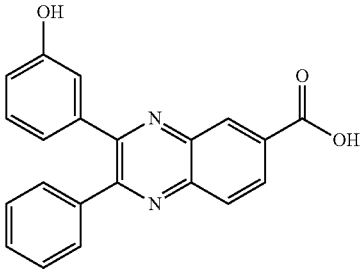

Step 1. 3-(3-Methoxyphenyl)-2-phenylquinoxaline-6-carboxylic acid

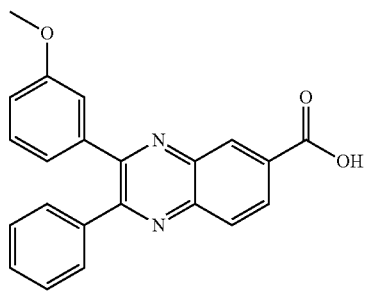 [SMILES: COc1cccc(-c2nc3cc(C(=O)O)ccc3nc2-c2ccccc2)c1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and 3-methoxyphenylboronic acid (86.13 mg, 0.57 mmol, 2.00 equiv) as reactants. Purification via silica gel column (dichloromethane/methanol (10:1)) yielded 85 mg (80%) of 3-(3-methoxyphenyl)-2-phenylquinoxaline-6-carboxylic acid as a yellow solid.

LC-MS (ES, m/z): [M+H]+ calculated for $C_{22}H_{16}N_2O_3$: 357. Found: 357.

Step 2. 3-(3-Hydroxyphenyl)-2-phenylquinoxaline-6-carboxylic acid

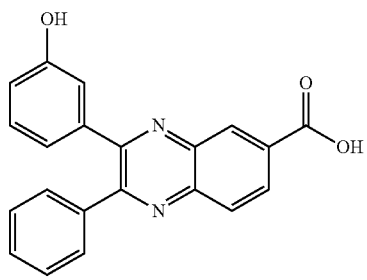 [SMILES: O=C(O)c1ccc2nc(-c3ccccc3)c(-c3cccc(O)c3)nc2c1]

The product was obtained via the method previously shown in Example 28, using 3-(3-methoxyphenyl)-2-phenylquinoxaline-6-carboxylic acid (85 mg, 0.21 mmol, 1.00 equiv, 90%) as the reactant. Purification via silica gel column (dichloromethane/methanol (10:1)) afforded 30 mg (40%) of 3-(3-hydroxyphenyl)-2-phenylquinoxaline-6-carboxylic acid as a yellow solid.

LC-MS (ES, m/z): [M+H]+ calculated for $C_{21}H_{14}N_2O_3$: 343. Found: 343.

$^1$H-NMR (300 MHz, MeOD, ppm) δ: 9.635 (1H, s), 8.644 (1H, s), 8.376-8.348 (1H, d, J=8.4 Hz), 8.165-8.136 (1H, d, J=8.7 Hz), 7.540-7.523 (2H, d, J=5.1 Hz), 7.410-7.388 (3H, d, J=6.6 Hz), 7.162-4-7.110 (1H, t), 6.997 (1H, s), 6.828-6.802 (2H, d, J=7.8 Hz).

EXAMPLE 47

2-Phenyl-3-(4-phenyl-phenyl)quinoxaline-6-carboxylic acid

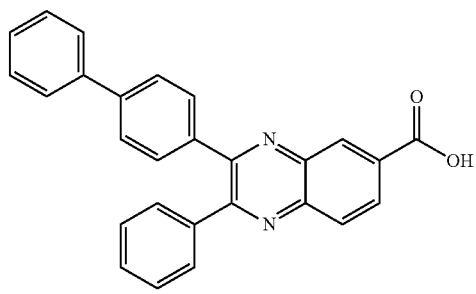 [SMILES: O=C(O)c1ccc2nc(-c3ccccc3)c(-c3ccc(-c4ccccc4)cc3)nc2c1]

The product was obtained via a Suzuki coupling reaction using the method previously shown in Example 20, Step 3, using methyl 3-bromo-2-phenylquinoxaline-6-carboxylate (100 mg, 0.29 mmol, 1.00 equiv) and 4-phenyl-phenylboronic acid (100 mg, 0.51 mmol, 1.50 equiv) as reactants. Purification via silica gel column (dichloromethane/methanol (15:1)) yielded 60 mg (51%) of 2-phenyl-3-(4-phenyl-phenyl)quinoxaline-6-carboxylic acid as a light yellow solid.

LC-MS (ES, m/z): [M+H]+ calculated for $C_{27}H_{18}N_2O_2$: 403. Found: 403.

$^1$H-NMR (300 MHz, DMSO, ppm) δ: 8.638 (1H, s), 8.137-8.109 (1H, d, J=8.4 Hz), 7.732-7.709 (1H, d, J=6.9 Hz), 7.684-7.582 (4H, m), 7.574-7.543 (4H, m), 7.503-7.387 (4H, m).

EXAMPLE 48

3-Ethyl-2-phenylquinoxaline-6-carboxylic acid

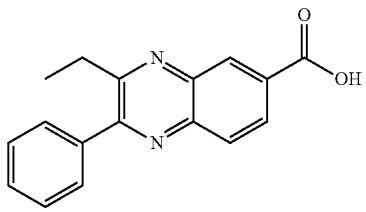 [SMILES: CCc1nc2cc(C(=O)O)ccc2nc1-c1ccccc1]

Step 1. Methyl 3-ethyl-2-phenylquinoxaline-6-carboxylate

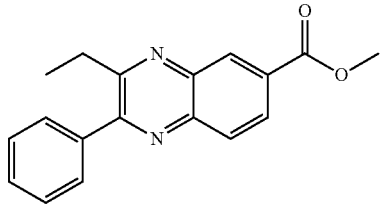 [SMILES: CCc1nc2cc(C(=O)OC)ccc2nc1-c1ccccc1]

A suspension of methyl 3-bromo-2-phenylquinoxaline-6-carboxylate (100 mg, 0.29 mmol, 1.00 equiv), X-phos (14 mg, 0.03 mmol, 0.10 equiv), $Pd_2(dba)_3$ (27 mg, 0.03 mmol, 0.10 equiv) in THF (10 mL), and $Et_2Zn$ in THF (5.8 mL, 20.00 equiv, 1M was allowed to react, with stifling, overnight while the temperature was maintained at 80° C. in an oil bath. The reaction was quenched by the addition of 2 mL of water. The resulting mixture was concentrated under vacuum and purified by prep-TLC (petroleum ether:ethyl acetate (4:1)) yielding 50 mg (35%) of methyl 3-ethyl-2-phenylquinoxaline-6-carboxylate as a yellow solid.

LC-MS (ES, m/z): M+H]+ calculated for $C_{18}H_{16}N_2O_2$: 293. Found: 293.

Step 2. 3-ethyl-2-phenylquinoxaline-6-carboxylic acid

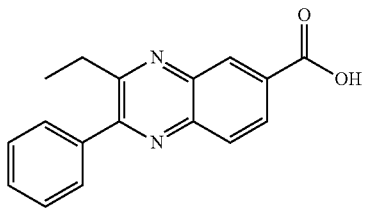 [SMILES: CCc1nc2cc(C(=O)O)ccc2nc1-c1ccccc1]

NaOH (22 mg, 0.55 mmol, 4.00 equiv) was added to a solution of methyl 3-ethyl-2-phenylquinoxaline-6-carboxylate (40 mg, 0.14 mmol, 1.00 equiv) in CH$_3$OH (20 mL), and the solution was allowed to react, with stifling, for 2 hrs at 50° C. The resulting mixture was concentrated under vacuum and combined with crude product from a previous batch prior to purification. The resulting mixture was purified by prep-HPLC, affording 11 mg (29%) of 3-ethyl-2-phenylquinoxaline-6-carboxylic acid as a white solid.

LC-MS (ES, m/z): [M+H]+ calculated for C$_{17}$H$_{14}$N$_2$O$_2$: 279. Found: 279.

$^1$H-NMR (300 MHz, CDCl$_3$, ppm): δ 1.278-1.314 (3H, m), 3.056-3.110 (2H, m), 7.566-7.657 (5H, m), 8.095-8.116 (1H, d, 6.3 Hz), 8.313-8.334 (1H, d, 6.3 Hz), 8.701-8.736 (1H, d, 10.5 Hz).

EXAMPLE 49

(3-(3-methoxyphenyl)-2-phenylquinoxalin-6-yl)methanol

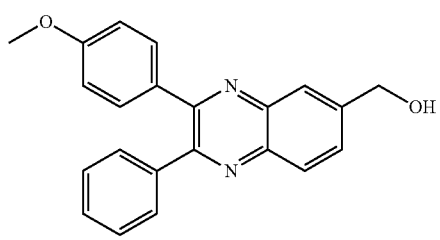 [SMILES: COc1ccc(-c2nc3cc(CO)ccc3nc2-c2ccccc2)cc1]

Step 1. Methyl 3-(4-methoxyphenyl)-2-phenylquinoxaline-6-carboxylate

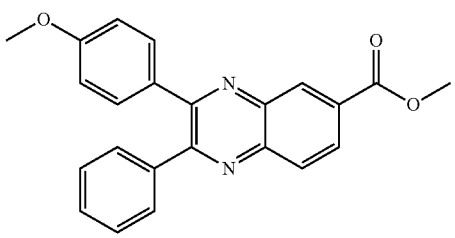

Into a 10-mL sealed tube purged and maintained with an inert atmosphere of nitrogen, was placed a solution of methyl 3-bromo-2-phenylquinoxaline-6-carboxylate (200 mg, 0.58 mmol, 1.00 equiv) in 1,4-dioxane (3 mL). To this was added 4-methoxyphenylboronic acid (133 mg, 0.88 mmol, 1.50 equiv). Addition of Pd$_2$(dba)$_3$ (32 mg, 0.03 mmol, 0.06 equiv) was next. This was followed by the addition of PCy$_3$ (22 mg, 0.08 mmol, 0.14 equiv). To the mixture was added K$_3$PO$_4$ (330 mg, 1.56 mmol, 3.00 equiv). The resulting solution was allowed to react, with stifling, overnight while the temperature was maintained at 110° C. in an oil bath. The resulting mixture was concentrated under vacuum. The residue was applied onto a silica gel column with ethyl acetate/petroleum ether (1:50). This resulted in 160 mg (74%) of methyl 3-(4-methoxyphenyl)-2-phenylquinoxaline-6-carboxylate as a yellow solid.

Step 2. (3-(3-methoxyphenyl)-2-phenylquinoxalin-6-yl)methanol

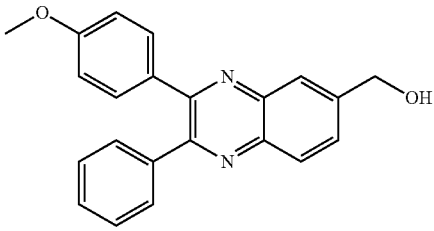 [SMILES: COc1ccc(-c2nc3cc(CO)ccc3nc2-c2ccccc2)cc1]

LiAlH$_4$ (10 mg, 0.26 mmol, 2.00 equiv) was added to a solution of methyl 3-(3-methoxyphenyl)-2-phenylquinoxaline-6-carboxylate (50 mg, 0.14 mmol, 1.00 equiv) in THF (30 mL) at 0° C. The resulting solution was allowed to react, with stifling, for 2 hrs at room temperature. The reaction was quenched by the addition of 10 mL of ethyl acetate. The solids were filtered out, and the filtrate was concentrated under vacuum, affording 30 mg (65%) of (3-(3-methoxyphenyl)-2-phenylquinoxalin-6-yl)methanol as a white solid.

LC-MS (ES, m/z): [M+H]+ calculated for C$_{22}$H$_{18}$N$_2$O$_2$: 343. Found: 343.

$^1$H-NMR (300 MHz, DMSO, ppm): δ 3.800 (3H, s), 4.809 (2H, s), 5.580 (1H, s), 6.930-6.958 (2H, d, 6.9 Hz), 7.428-7.506 (7H, m), 7.805-7.828 (1H, d, 6.9 Hz), 8.059-8.086 (2H, m).

EXAMPLE 50

3-(3-Carboxyphenyl)-2-phenylquinoxaline-6-carboxylic acid

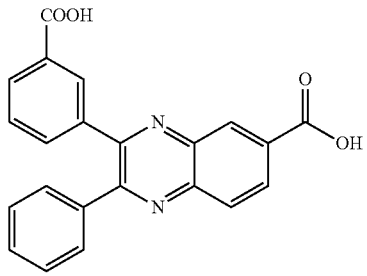 [SMILES: O=C(O)c1cccc(-c2nc3cc(C(=O)O)ccc3nc2-c2ccccc2)c1]

Step 1. Methyl 3-(3-carboxyphenyl)-2-phenylquinoxaline-6-carboxylate

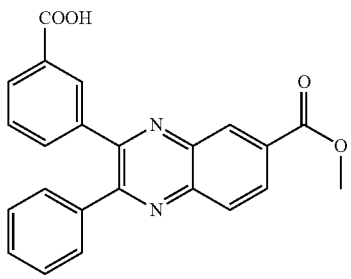 [SMILES: COC(=O)c1ccc2nc(-c3ccccc3)c(-c3cccc(C(=O)O)c3)nc2c1]

The product was obtained via a Suzuki coupling reaction using the method previously shown in Example 20, Step 3, using methyl 3-bromo-2-phenylquinoxaline-6-carboxylate (150 mg, 0.44 mmol, 1.00 equiv) and 3-carboxyphenylboronic acid (145.6 mg, 0.88 mmol, 2.00 equiv) as reactants. Purification via silica gel column (DCM/MeOH (20:1))

yielded 141.8 mg (78%) of methyl 3-(3-carboxyphenyl)-2-phenylquinoxaline-6-carboxylate as a white solid.

LC-MS (ES, m/z): [M+H]$^+$ calculated for $C_{23}H_{17}N_2O_4$: 385. Found: 385.

Step 2. 3-(3-carboxyphenyl)-2-phenylquinoxaline-6-carboxylic acid

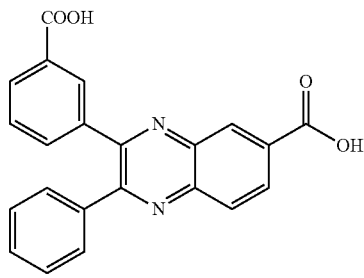 [SMILES: O=C(O)c1cccc(-c2nc3cc(C(=O)O)ccc3nc2-c2ccccc2)c1]

A solution of NaOH (68.7 mg, 1.72 mmol, 5.00 equiv) in water (3 mL) was added dropwise with stirring to a solution of methyl 3-(3-carboxyphenyl)-2-phenylquinoxaline-6-carboxylate (131.9 mg, 0.33 mmol, 1.00 equiv. in methanol (10 mL). The resulting solution was stirred overnight at 50° C. in an oil bath. The mixture was concentrated by vacuum; the pH was adjusted to 3-4 with 1N hydrochloric acid, the solid precipitate was filtered and washed with ether, affording 60 mg (49%) of 3-(3-carboxyphenyl)-2-phenylquinoxaline-6-carboxylic acid as a white solid.

LC-MS (ES, m/z): [M+H]$^+$ calculated for $C_{22}H_{15}N_2O_4$: 371. Found: 371.

$^1$H-NMR (300 MHz, DMSO, ppm): δ 13.292 (s, 1H), 8.687 (s, 1H), 8.837-8.171 (m, 2H), 7.986-7.960 (d, J=7.8 Hz, 1H), 7.672-7.646 (d, J=7.8 Hz, 1H), 7.527-7.362 (m, 6H).

EXAMPLE 51

3-(4-(N-Methylmethylsulfonamido)phenyl)-2-phenylquinoxaline-6-carboxylic acid

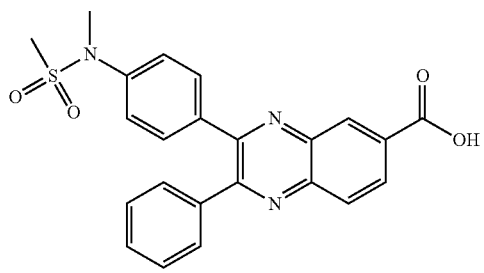 [SMILES: CN(c1ccc(-c2nc3cc(C(=O)O)ccc3nc2-c2ccccc2)cc1)S(C)(=O)=O]

Step 1. Methyl 3-(4-(t-butoxycarbonylamino)phenyl)-2-phenylquinoxaline-6-carboxylate

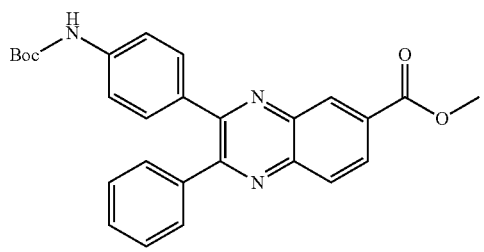 [SMILES: COC(=O)c1ccc2nc(-c3ccccc3)c(-c3ccc(NC(=O)OC(C)(C)C)cc3)nc2c1]

Into a 40-mL sealed tube purged and maintained with an inert atmosphere of nitrogen, was placed methyl 3-bromo-2-phenylquinoxaline-6-carboxylate (500 mg, 1.46 mmol, 1.00 equiv), tert-butyl 4-(4,4,5,5-tetramethyl-1,3,2-dioxaborolan-2-yl)phenylcarbamate (931 mg, 2.92 mmol, 2.00 equiv), PCy$_3$ (114.5 mg, 0.41 mmol, 0.28 equiv), Pd$_2$(dba)$_3$ (161.2 mg, 0.18 mmol, 0.12 equiv), K$_3$PO$_4$ (928.6 mg, 4.38 mmol, 3.00 equiv), dioxane (10 mL). The resulting solution was stirred overnight at 100° C. in an oil bath. The resulting mixture was concentrated under vacuum. Purification via silica gel column (ethyl acetate/petroleum ether (1:10)) afforded 368 mg (55%) of methyl 3-(4-(t-butoxycarbonyl)phenyl)-2-phenylquinoxaline-6-carboxylate as a yellow solid.

LC-MS (ES, m/z): [M+H]$^+$ calculated for $C_{27}H_{26}N_3O_4$: 456. Found: 456.

Step 2. 3-(4-(t-butoxycarbonyl(methyl)amino)phenyl)-2-phenylquinoxaline-6-carboxylic acid

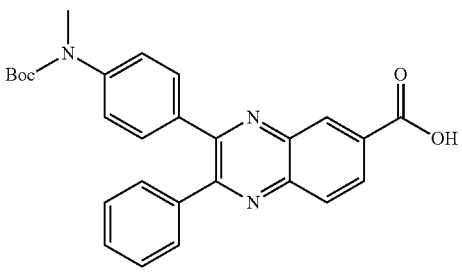 [SMILES: CN(C(=O)OC(C)(C)C)c1ccc(-c2nc3cc(C(=O)O)ccc3nc2-c2ccccc2)cc1]

Sodium hydride (60 mg, 2.50 mmol, 5.60 equiv) was added to a solution of methyl 3-(4-(t-butoxycarbonyl)phenyl)-2-phenylquinoxaline-6-carboxylate (200 mg, 0.42 mmol, 1.00 equiv, 95%) in THF (10 mL) at 0° C. under an inert atmosphere and stirred for 1 h. A solution of CH$_3$I (125 mg, 0.88 mmol, 2.00 equiv) in THF (1 mL) was added dropwise with stirring at 0° C. The resulting solution was stirred overnight at room temperature. The reaction was quenched by the addition of water. The pH value of the solution was adjusted to 3-4 with 1N HCl. The resulting mixture was concentrated under vacuum, yielding 213.5 mg (crude) of 3-(4-(t-butoxycarbonyl)phenyl)-2-phenylquinoxaline-6-carboxylic acid as a yellow solid.

Step 3. Methyl 3-(4-(t-butoxycarbonyl(methyl)amino)phenyl)-2-phenylquinoxaline-6-carboxylate

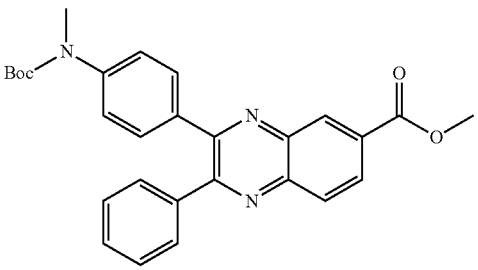 [SMILES: COC(=O)c1ccc2nc(-c3ccccc3)c(-c3ccc(N(C)C(=O)OC(C)(C)C)cc3)nc2c1]

A solution of 3-(4-(t-butoxycarbonyl(methyl)amino)phenyl)-2-phenylquinoxaline-6-carboxylic acid (213.5 mg, 0.46 mmol, 1.00 equiv, 99%) and K$_2$CO$_3$ (324.2 mg, 2.35 mmol, 5.00 equiv) in DMF (8 mL) was stirred 45 min at room temperature under an inert atmosphere. CH$_3$I (333.7 mg, 2.35 mmol, 5.00 equiv) was added dropwise, with stirring, at 0° C. The resulting solution was stirred for 1 h at room temperature, then quenched by water. The solution was extracted with 5×10 mL of CH$_2$Cl$_2$, and the organic layers combined and dried over anhydrous sodium sulfate. The solids were filtered out, and the resulting mixture was concentrated under vacuum affording 218 mg (98%) of methyl 3-(4-(t-butoxycarbonyl(methyl)amino)phenyl)-2-phenylquinoxaline-6-carboxylate as a yellow solid.

LC-MS (ES, m/z): [M+H] calculated for $C_{28}H_{29}N_3O_4$: 470. Found: 470.

Step 4. Methyl 3-(4-(methylamino)phenyl)-2-phenylquinoxaline-6-carboxylate

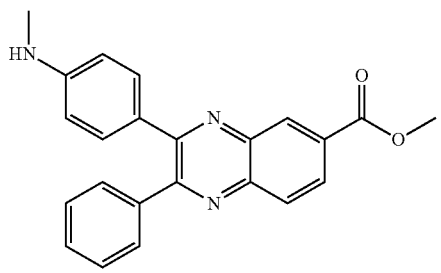 [SMILES: CNc1ccc(-c2nc3cc(C(=O)OC)ccc3nc2-c2ccccc2)cc1]

Trifluoroacetic acid (6 mL) was added dropwise with stirring to a solution of methyl 3-(4-(t-butoxycarbonyl)phenyl)-2-phenylquinoxaline-6-carboxylate (218 mg, 0.46 mmol, 1.00 equiv, 98%) in $CH_2Cl_2$ (10 mL) at 0° C. and stirred for 3 h at room temperature. The resulting mixture was concentrated under vacuum. The pH value of the solution was adjusted to 7-8 with $Na_2CO_3$ (aqueous, saturated), then extracted with 5×20 mL of dichloromethane and the organic layers combined and dried over anhydrous sodium sulfate. The solids were filtered out, and the filtrate was concentrated under vacuum, yielding 144.7 mg (86%) of methyl 3-(4-(methylamino)phenyl)-2-phenylquinoxaline-6-carboxylate as a yellow solid.

LC-MS (ES, m/z): [M+H]$^+$ calculated for $C_{23}H_{20}N_3O_2$: 370. Found: 370.

Step 5. Methyl 3-(4-(N-methylmethan-3-ylsulfonamido)phenyl)-2-phenylquinoxaline-6-carboxylate

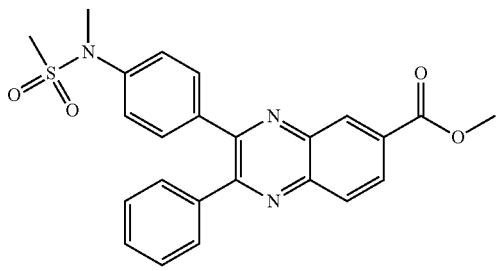 [SMILES: COC(=O)c1ccc2nc(-c3ccccc3)c(-c3ccc(N(C)S(C)(=O)=O)cc3)nc2c1]

To a solution of methyl 3-(4-(methylamino)phenyl)-2-phenylquinoxaline-6-carboxylate (144.7 mg, 0.39 mmol, 1.00 equiv) in dichloromethane (17 mL) were added sequentially, triethylamine (196.95 mg, 1.95 mmol, 5.00 equiv) and methanesulfonyl chloride (49.2 mg, 0.43 mmol, 1.10 equiv) dropwise with stirring at 0° C. The resulting solution was stirred for 1.5 h at room temperature, then concentrated under vacuum. The residue was diluted with dichloromethane, washed with $NaHCO_3$ (aqueous, saturated), and extracted with 5×20 mL of dichloromethane. The organic layers were combined, dried over anhydrous sodium sulfate, and filtered. The filtrate was concentrated under vacuum affording 216.4 mg (crude) of methyl 3-(4-(N-methylmethan-3-ylsulfonamido)phenyl)-2-phenylquinoxaline-6-carboxylate as a yellow solid.

LC-MS (ES, m/z): [M+H]$^+$ calculated for $C_{24}H_{22}N_3O_4S$: 448. Found: 448.

Step 6. 3-(4-(N-methylmethylsulfonamido)phenyl)-2-phenylquinoxaline-6-carboxylic acid

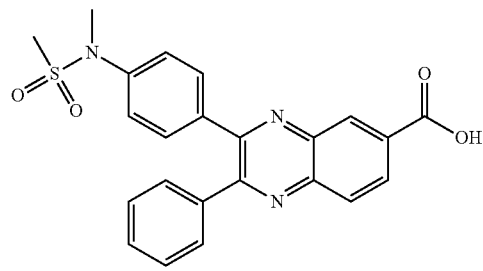 [SMILES: CN(c1ccc(-c2nc3cc(C(=O)O)ccc3nc2-c2ccccc2)cc1)S(C)(=O)=O]

The product was obtained via the method previously shown in Example 40, step 2, using methyl 3-(4-(N-methylmethan-3-ylsulfonamido)phenyl)-2-phenylquinoxaline-6-carboxylate (216.4 mg, 0.48 mmol, 1.00 equiv) as the reactant. The resulting solid was filtered and washed with methanol, yielding 35 mg (17%) of 3-(4-(N-methylmethan-3-ylsulfonamido)phenyl)-2-phenylquinoxaline-6-carboxylic acid as a light yellow solid.

LC-MS (ES, m/z): [M+H]$^+$ calculated for $C_{23}H_{20}N_3O_4S$: 434. Found: 434.

$^1$H-NMR (300 MHz, DMSO, ppm): δ 8.671-8.666 (d, J=1.5 Hz, 1H), 8.351-8.236 (m, 2H), 7.561-7.385 (m, 9H), 2.975 (s, 3H), 2.743 (s, 3H).

EXAMPLE 52

3-(4-(Isopropylsulfonamido)phenyl)-2-phenylquinoxaline-6-carboxylic acid

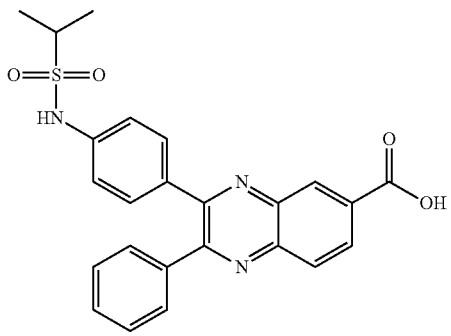 [SMILES: CC(C)S(=O)(=O)Nc1ccc(-c2nc3cc(C(=O)O)ccc3nc2-c2ccccc2)cc1]

Step 1. Methyl 2-phenyl-3-(4-(propan-2-ylsulfonamido)phenyl)quinoxaline-6-carboxylate

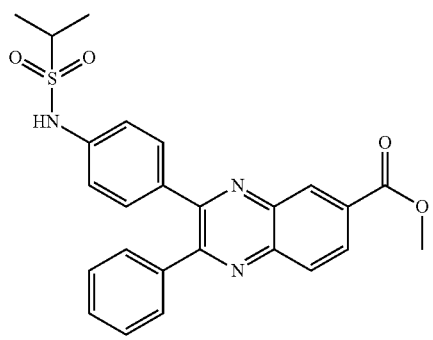 [SMILES: COC(=O)c1ccc2nc(-c3ccccc3)c(-c3ccc(NS(=O)(=O)C(C)C)cc3)nc2c1]

Propane-2-sulfonyl chloride (300 mg, 2.10 mmol, 5.00 equiv) was added to a solution of methyl 3-(4-aminophenyl)-2-phenylquinoxaline-6-carboxylate (150 mg, 0.42 mmol, 1.00 equiv) and DIEA (545 mg, 4.22 mmol, 10.00 equiv) in dichloromethane (30 mL) at 0° C., and the resulting solution was stirred overnight at room temperature. The reaction mixture was concentrated under vacuum and purified via silica gel column (ethyl acetate/petroleum ether (1:10)), affording 170 mg (87%) of methyl 2-phenyl-3-(4-(propan-2-ylsulfonamido)phenyl)quinoxaline-6-carboxylate as a yellow solid.

Step 2. 3-(4-(isopropylsulfonamido)phenyl)-2-phenylquinoxaline-6-carboxylic acid

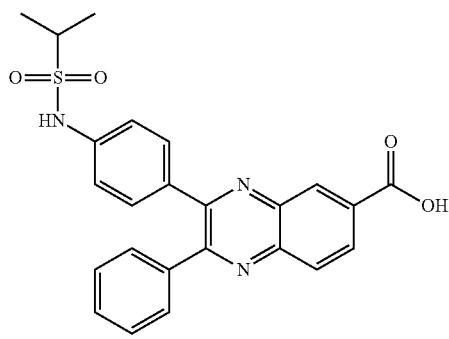 [SMILES: CC(C)S(=O)(=O)Nc1ccc(-c2nc3cc(C(=O)O)ccc3nc2-c2ccccc2)cc1]

The product was obtained via the method previously shown in Example 40, step 2, using methyl 2-phenyl-3-(4-(propan-2-ylsulfonamido)phenyl)quinoxaline-6-carboxylate (150 mg, 0.33 mmol, 1.00 equiv) as a reactant. The crude product was purified by re-crystallization from methanol, yielding 30 mg (21%) of 3-(4-(isopropylsulfonamido)phenyl)-2-phenylquinoxaline-6-carboxylic acid as a yellow solid.

LC-MS (ES, m/z): [M+H]$^+$ calculated for $C_{24}H_{22}N_3O_4S$: 448. Found: 448.

$^1$H-NMR (300 MHz, DMSO, ppm): δ 9.997 (s, 1H), 8.649 (s, 1H), 8.644-8.213 (m, 2H), 7.531-7.377 (m, 7H), 7.224-7.171 (m, 2H), 1.268-1.246 (d, 0.1=6.6 Hz, 6H).

EXAMPLE 53

2,3-Bis(4-methoxyphenyl)quinoxaline-6-sulfonamide

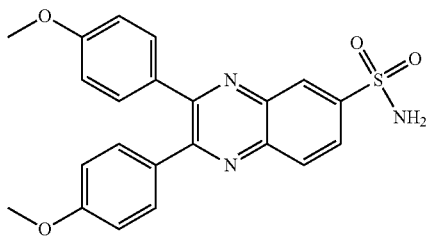 [SMILES: COc1ccc(-c2nc3ccc(S(N)(=O)=O)cc3nc2-c2ccc(OC)cc2)cc1]

Step 1. 3,4-diaminobenzenesulfonic acid

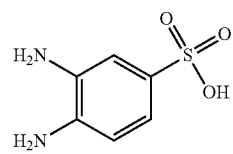

Concentrated sulfuric acid (200 mL) was added to benzene-1,2-diamine (20 g, 184.95 mmol, 1.00 equiv) at −40° C., and the solution was stirred for 30 minutes at room temperature, then overnight at 140° C. in an oil bath. Upon cooling to room temperature, the reaction was quenched by 500 g of ice. The solids were collected by filtration, and the crude product was purified by re-crystallization from water affording 9.8 g (28%) of 3,4-diaminobenzenesulfonic acid as a white solid.

Step 2.
2,3-bis(4-methoxyphenyl)quinoxaline-6-sulfonic acid

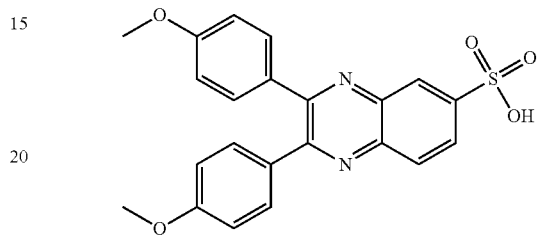

A solution of 1,2-bis(4-methoxyphenyl)ethane-1,2-dione (400 mg, 1.48 mmol, 1.00 equiv) and 3,4-diaminobenzenesulfonic acid (278 mg, 1.48 mmol, 1.00 equiv) in ethanol/water (10/10 mL) was stirred overnight at reflux in an oil bath. The resulting mixture was concentrated under vacuum, yielding 500 mg (80%) of 2,3-bis(4-methoxyphenyl)quinoxaline-6-sulfonic acid as a brown solid.

Steps 3 and 4.
2,3-bis(4-methoxyphenyl)quinoxaline-6-sulfonamide

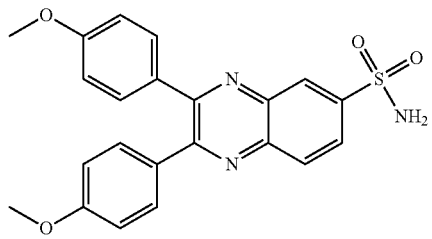 [SMILES: COc1ccc(-c2nc3ccc(S(N)(=O)=O)cc3nc2-c2ccc(OC)cc2)cc1]

DMF (2 mL) was added dropwise with stirring to a solution of 2,3-bis(4-methoxyphenyl)quinoxaline-6-sulfonic acid (137.2 mg, 0.33 mmol, 1.00 equiv) in thionyl chloride (12 mL), stirred at reflux for 3 h in an oil bath, then concentrated under vacuum. The residue was dissolved in acetonitrile (10 mL), and added dropwise to a solution of ammonia (2 g) in acetonitrile (10 mL) at 0° C. The resulting mixture was stirred for overnight at room temperature. The reaction mixture was concentrated under vacuum and purified via Prep-HPLC affording 16 mg (12%) of 2,3-bis(4-methoxyphenyl)quinoxaline-6-sulfonamide as a light yellow solid.

LC-MS (ES, m/z): [M+H]$^+$ calculated for $C_{22}H_{20}N_3O_4S$: 422. Found: 422.

$^1$H-NMR (300 MHz, DMSO, ppm): δ 8.482-8.476 (d, J=1.8 Hz, 1H), 8.298-8.269 (d, J=8.7 Hz, 1H), 8.174-8.138 (m, 1H), 7.698 (s, 2H), 7.518-7.489 (d, J=8.7 Hz, 4H), 6.988-6.961 (d, J=8.1 Hz, 4H), 3.805 (s, 3H).

EXAMPLE 54

2,3-Bis(4-methoxyphenyl)-N-methylquinoxaline-6-sulfonamide

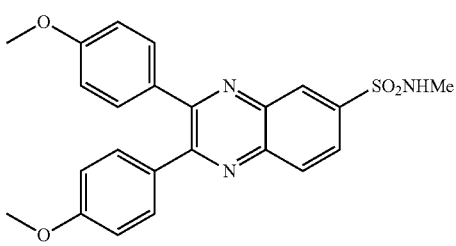

A solution of 2,3-bis(4-methoxyphenyl)quinoxaline-6-sulfonic acid (200 mg, 0.47 mmol, 1.00 equiv) in thionyl chloride (20 mL) was heated under reflux for 3 h, then concentrated under vacuum. The residue was diluted with 10 ml of $CH_2Cl_2$ and added dropwise into a solution of $MeNH_2$.HCl (318 mg, 4.75 mmol, 10.00 equiv) and DIEA (917 mg, 7.11 mmol, 15.00 equiv) in $CH_2Cl_2$ (20 mL) at 0° C. The resulting solution was stirred for overnight at room temperature, concentrated under vacuum, and purified by Prep-HPLC, yielding 100 mg (49%) of 2,3-bis(4-methoxyphenyl)-N-methylquinoxaline-6-sulfonamide as a yellow solid.

LC-MS (ES, m/z): $[M+H]^+$ calculated for $C_{23}H_{22}N_3O_4S$: 436. Found: 436.

$^1$H-NMR (300 MHz, DMSO, ppm): δ 8.439-8.433 (s, 1H), 8.324-8.295 (d, J=8.7 Hz, 1H), 8.110-8.074 (m, 1H), 7.815-7.767 (m, 1H), 7.517-7.488 (d, J=8.7 Hz, 2H), 6.988-6.958 (d, J=9 Hz, 4H), 3.805 (s, 6H), 3.333-3.311 (s, 3H).

EXAMPLE 55

2,3-Bis(4-methoxyphenyl)-6-(morpholinosulfonyl)quinoxaline

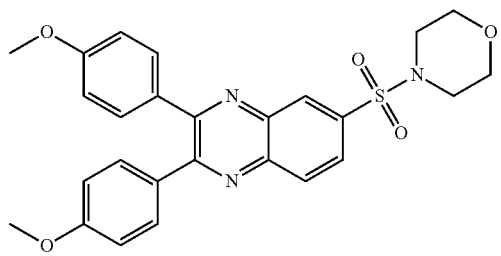 [SMILES: COc1ccc(-c2nc3ccc(S(=O)(=O)N4CCOCC4)cc3nc2-c2ccc(OC)cc2)cc1]

The product was obtained using the same synthetic methods as Example 54, using 2,3-bis(4-methoxyphenyl)quinoxaline-6-sulfonic acid (350 mg, 0.83 mmol, 1.00 equiv) and morpholine (1.44 g, 16.53 mmol, 20.00 equiv) as reactants. Purification by Prep-HPLC afforded 60 mg (34%) of 2,3-bis(4-methoxyphenyl)-6-(morpholinosulfonyl)quinoxaline as a white solid.

LC-MS (ES, m/z): $[M+H]^+$ calculated for $C_{26}H_{26}N_3O_5S$: 492. Found: 492.

$^1$H-NMR (300 MHz, DMSO, ppm): δ 8.412-0.406 (s, 1H), 8.355-0.325 (d, J=9 Hz, 1H), 8.069-0.033 (d, J=10.8 Hz, 1H), 7.534-0.505 (d, J=8.7 Hz, 4H), 6.995-6.968 (d, J=8.1 Hz, 4H), 3.809 (s, 6H), 3.659 (m, 4H), 3.019 (m, 4H).

EXAMPLE 56

(E)-3-(2,3-bis(4-methoxyphenyl)quinoxalin-6-yl)acrylic acid

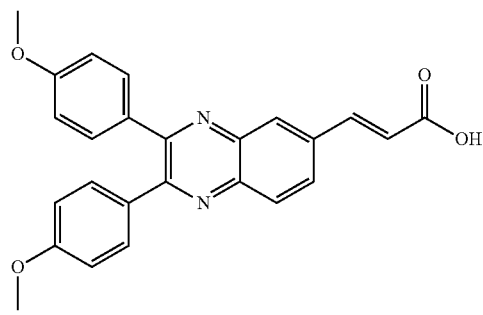 [SMILES: COc1ccc(-c2nc3ccc(/C=C/C(=O)O)cc3nc2-c2ccc(OC)cc2)cc1]

Step 1.
6-bromo-2,3-bis(4-methoxyphenyl)quinoxaline

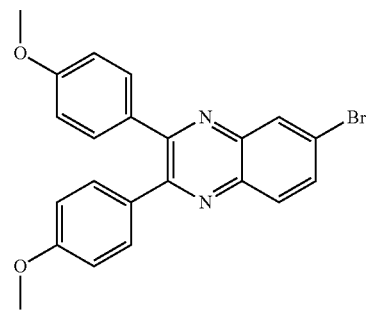 [SMILES: COc1ccc(-c2nc3ccc(Br)cc3nc2-c2ccc(OC)cc2)cc1]

A solution of 1,2-bis(4-methoxyphenyl)ethane-1,2-dione (540 mg, 2.00 mmol, 1.00 equiv) and 4-bromobenzene-1,2-diamine (380 mg, 2.03 mmol, 1.10 equiv) in acetic acid (5 mL) was stirred for 3 h at 130° C. in an oil bath, then quenched by the addition of water (30 mL). The solids were collected by filtration and washed with water (20 mL). The solid was dried in an oven under reduced pressure, yielding 400 mg (48%) of 6-bromo-2,3-bis(4-methoxyphenyl)quinoxaline as a brown solid.

Step 2. (E)-methyl 3-(2,3-bis(4-methoxyphenyl)quinoxalin-6-yl)acrylate

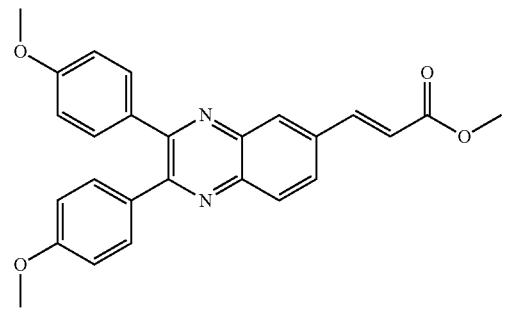 [SMILES: COC(=O)/C=C/c1ccc2nc(-c3ccc(OC)cc3)c(-c3ccc(OC)cc3)nc2c1]

A solution of 6-bromo-2,3-bis(4-methoxyphenyl)quinoxaline (100 mg, 0.24 mmol, 1.00 equiv), methyl acrylate (40.8 mg, 0.47 mmol, 2.00 equiv), $Pd(OAc)_2$ (5.3 mg, 0.02 mmol, 0.10 equiv), $PPh_3$ (24.8 mg, 0.09 mmol, 0.40 equiv) in DMF/Et₃N (4/2 mL). The resulting solution was stirred overnight at 100° C. under an inert atmosphere. The mixture was concentrated under vacuum and purified via silica gel column (ethyl acetate/petroleum ether (1:30)), yielding 80 mg (79%) of (E)-methyl 3-(2,3-bis(4-methoxyphenyl)quinoxalin-6-yl) acrylate as a yellow solid.

Step 3. (E)-3-(2,3-bis(4-methoxyphenyl)quinoxalin-6-yl)acrylic acid

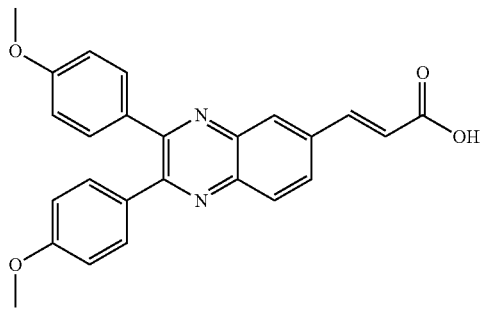 [SMILES: COc1ccc(-c2nc3ccc(/C=C/C(=O)O)cc3nc2-c2ccc(OC)cc2)cc1]

A solution of (E)-methyl 3-(2,3-bis(4-methoxyphenyl)quinoxalin-6-yl)acrylate (150 mg, 0.35 mmol, 1.00 equiv) and sodium hydroxide (70.4 mg, 1.76 mmol, 5.00 equiv) in methanol (10 mL) and H₂O (2 ml) was stirred for 2 h at 50° C. in an oil bath. The resulting mixture was concentrated under vacuum, diluted with 20 mL of water. The pH value of the solution was adjusted to 3 with 1N hydrochloric acid. The solids were collected by filtration, and purified by re-crystallization from methanol, affording 80 mg (55%) of (E)-3-(2,3-bis(4-methoxyphenyl)quinoxalin-6-yl)acrylic acid as a yellow solid.

LC-MS (ES, m/z): [M+H]⁺ calculated for $C_{25}H_{21}N_2O_4$: 413. Found: 413.

¹H-NMR (300 MHz, DMSO, ppm): δ 8.368 (s, 1H), 8.223-8.195 (d, J=4 Hz, 1H), 8.101-8.072 (d, J=7 Hz, 1H), 7.895-7.842 (d, J=0.9 Hz, 1H), 7.492-7.457 (m, 4H), 6.976-6.942 (m, 4H), 6.840-6.787 (d, J=15.9 Hz, 1H), 3.800 (s, 6H).

EXAMPLE 57

2,3-Bis(4-methoxyphenyl)quinoxaline-6-carbonitrile

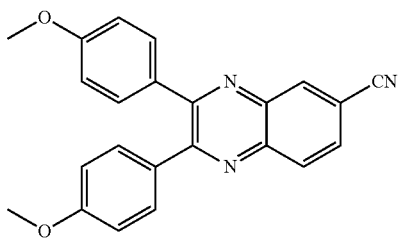 [SMILES: COc1ccc(-c2nc3ccc(C#N)cc3nc2-c2ccc(OC)cc2)cc1]

A solution of 3,4-diaminobenzonitrile (50 mg, 0.30 mmol, 1.00 equiv, 80%) and 1,2-bis(4-methoxyphenyl)ethane-1,2-dione (89 mg, 0.33 mmol, 1.00 equiv) in acetic acid (5 mL) was stirred for 30 min at 30° C. in an oil bath, then at 130° C. for 3 h. The reaction was quenched with 10 mL of water. The solids were collected by filtration and dried in an oven under reduced pressure, yielding 80 mg (72%) of 2,3-bis(4-methoxyphenyl)quinoxaline-6-carbonitrile as a yellow solid.

LC-MS (ES, m/z): [M+H]⁺ calculated for $C_{23}H_{18}N_3O_2$: 368. Found: 368.

¹H-NMR (300 MHz, CDCl₃, ppm): δ 8.698-8.702 (s, 1H), 8.229-8.258 (d, J=8.7 Hz, 1H), 8.108-8.142 (d, J=10.2 Hz, 1H), 7.468-7.515 (s, 4H), 6.957-6.982 (m, 4H), 3.802 (s, 6H).

EXAMPLE 58

2,3-Bis(4-methoxyphenyl)quinoxaline-5-carboxylic acid

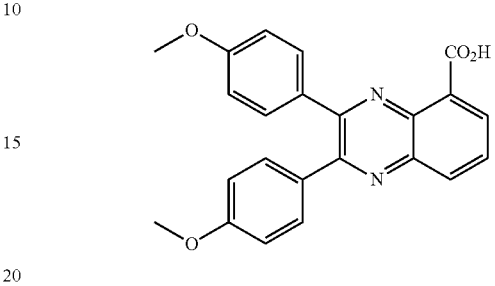

A solution of 1,2-bis(4-methoxyphenyl)ethane-1,2-dione (270 mg, 1.00 mmol, 1.00 equiv) and 2,3-diaminobenzoic acid (152 mg, 1.00 mmol, 1.00 equiv) in acetic acid (10 mL) was heated under reflux for 3 h. The reaction was quenched by the addition of 20 mL of ice/water. The solids were collected by filtration and purified by re-crystallization from methanol, affording 100 mg (26%) of 2,3-bis(4-methoxyphenyl)quinoxaline-5-carboxylic acid as a yellow solid.

LC-MS-PH (ES, m/z): [M+H]⁺ calculated for $C_{23}H_{19}N_2O_4$: 387. Found: 387.

¹H-NMR (300 MHz, DMSO, ppm): δ 14.605 (s, 1H), 8.422-8.358 (m, 2H), 8.002-7.963 (m, 1H), 7.520-7.492 (m, 4H), 7.033-6.972 (m, 4H), 3.819-3.808 (s, 6H).

EXAMPLE 59

2,3-Bis(4-ethylphenyl)-N-methoxyquinoxaline-6-carboxamide

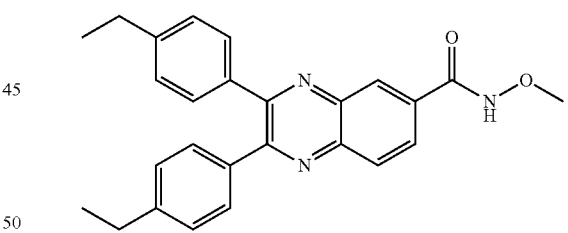

A solution of 2,3-bis(4-ethylphenyl)quinoxaline-6-carboxylic acid (150 mg, 0.39 mmol, 1.00 equiv) in thionyl chloride (20 mL) was heated under reflux for 3 h in a oil bath. The resulting solution was concentrated under vacuum and diluted with 20 ml of CH₂Cl₂. The resulting solution was added to a solution of O-methyl-hydroxylamine hydrochloride (326 mg, 3.93 mmol, 10.00 equiv) and NEt₃ (396 mg, 3.92 mmol, 10.00 equiv) in CH₂Cl₂ (20 mL) at 0° C. and stirred overnight at room temperature. The reaction mixture was concentrated under vacuum, and the crude product (100 mg) was purified by Prep-HPLC yielding 15 mg (7%) of 2,3-bis(4-ethylphenyl)-N-methoxyquinoxaline-6-carboxamide as a white solid.

LC-MS (ES, m/z): [M+H]⁺ calculated for $C_{26}H_{26}N_3O_2$: 412. Found: 412.

¹H-NMR (300 MHz, CDCl₃, ppm): δ 8.989 (s, 1H), 8.565 (s, 1H), 8.295-8.180 (m, 2H), 7.515-7.497 (d, J=5.4 Hz, 4H), 7.230-7.205 (d, J=7.5 Hz, 4H), 3.995 (s, 3H), 2.747-2.672 (m, 4H), 1.298-1.251 (m, 6H).

EXAMPLE 60

2-(4-Methoxyphenyl)-3-phenylquinoline-7-carboxylic acid

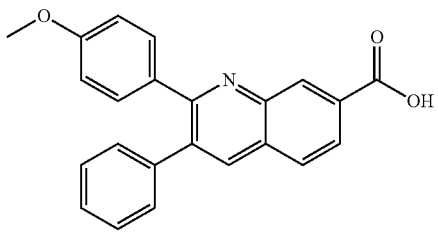 [SMILES: COc1ccc(-c2nc3cc(C(=O)O)ccc3cc2-c2ccccc2)cc1]

Step 1. Methyl 3-aminobenzoate

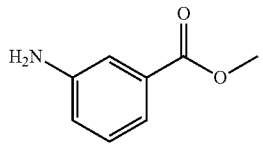

Thionyl chloride (43 g, 361.34 mmol, 5.00 equiv) was added dropwise with stirring at 0° C. to a solution of 3-aminobenzoic acid (10 g, 72.92 mmol, 1.00 equiv) in methanol (100 mL) and allowed to react, with stirring, overnight under reflux. The resulting mixture was concentrated under vacuum and quenched by the addition of 50 mL of water/ice. The resulting solids were collected via vacuum filtration and dried in an oven under reduced pressure, affording 10.3 g (93%) of methyl 3-aminobenzoate as a white solid.

Step 2. (E)-Methyl 3-(4-methoxybenzylideneamino)benzoate

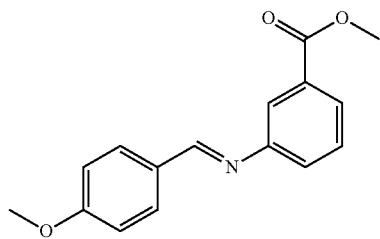

4-Methoxybenzaldehyde (2.72 g, 19.98 mmol, 1.00 equiv), methyl 3-aminobenzoate (3 g, 19.85 mmol, 1.00 equiv), and methanol (30 mL) were placed in a 50-mL round-bottom flask and allowed to react, with stirring, at room temperature overnight. The resulting solids were collected by filtration and dried in an oven under reduced pressure, yielding 3 g (56%) of (E)-methyl 3-(4-methoxybenzylideneamino)benzoate as a yellow solid.

Step 3. Methyl 2-(4-methoxyphenyl)-3-phenylquinoline-7-carboxylate

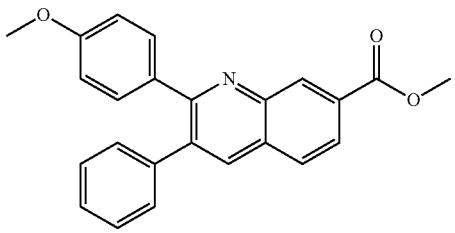

A mixture of (E)-methyl 3-(4-methoxybenzylideneamino)benzoate (1.1 g, 4.08 mmol, 1.00 equiv), 2-phenylacetaldehyde (480 mg, 4.00 mmol, 1.00 equiv), hydrochloric acid in tetrahydrofuran (0.5 mL, 10M) and DMSO (2 mL) was placed in a 10-mL sealed tube and stirred overnight at 70° C. in an oil bath. The resulting mixture was concentrated under vacuum and purified via Flash-Prep-HPLC (H₂O/CH₃CN=10% increasing to H₂O/CH₃CN=60% within 5 min; Detector, UV 254 nm) affording 70 mg (5%) of methyl 2-(4-methoxyphenyl)-3-phenylquinoline-7-carboxylate as a yellow solid.

LC-MS: (ES, m/z): 370 [M+H]⁺

Step 4. 2-(4-Methoxyphenyl)-3-phenylquinoline-7-carboxylic acid

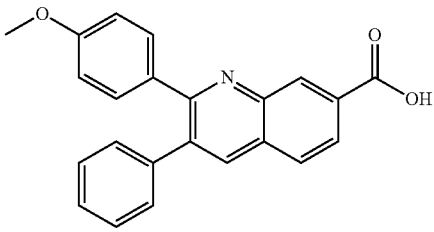 [SMILES: COc1ccc(-c2nc3cc(C(=O)O)ccc3cc2-c2ccccc2)cc1]

Methyl 2-(4-methoxyphenyl)-3-phenylquinoline-7-carboxylate (40 mg, 0.11 mmol, 1.00 equiv), LiOH (13 mg, 0.54 mmol, 5.00 equiv), methanol (5 mL), and water (0.5 mL) were placed in a 50-mL round-bottom flask and stirred for 5 hr at 50° C. in an oil bath. The resulting mixture was concentrated under vacuum, diluted with 10 mL of H₂O, and the pH adjusted to 4-5 with 1N HCl. The resulting solids were collected by filtration and dried in an oven under reduced pressure, yielding 23 mg (59%) of 2-(4-methoxyphenyl)-3-phenylquinoline-7-carboxylic acid as a yellow solid.

LC-MS: (ES, m/z): 356 [M+H]⁺

¹H-NMR (300 MHz, DMSO, ppm): δ 8.593 (s, 1H), 8.416 (s, 1H), 8.094 (s, 2H), 7.386-7.307 (m, 7H), 6.890-6.861 (d, J=8.7 Hz, 2H), 3.769 (s, 3H).

EXAMPLE 61

2,3-Bis(4-methoxyphenyl)quinoline-6-carboxylic acid

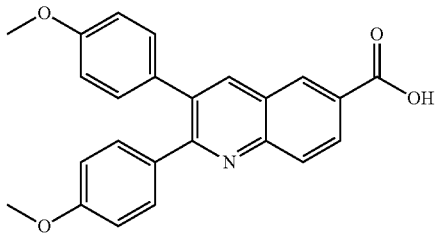 [SMILES: COc1ccc(-c2cc3cc(C(=O)O)ccc3nc2-c2ccc(OC)cc2)cc1]

Step 1. Ethyl 4-hydroxy-2,3-bis(4-methoxyphenyl) quinoline-6-carboxylate

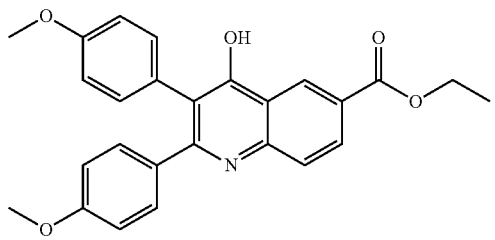 [SMILES: CCOC(=O)c1ccc2nc(-c3ccc(OC)cc3)c(-c3ccc(OC)cc3)c(O)c2c1]

Methyl 2,3-bis(4-methoxyphenyl)-3-oxopropanoate (1.3 g, 4.14 mmol, 1.00 equiv), ethyl 4-aminobenzoate (680 mg, 4.12 mmol, 1.00 equiv), $CH_3SO_3H$ (118 mg, 1.23 mmol, 0.30 equiv), and $Ph_2O$ (20 mL) were placed in a 100-mL round-bottom flask stirred for 1 h at 90° C., then at 180° C. for 3 h, in an oil bath. Upon cooling, 100 ml of petroleum ether was added. The resulting solid was collected by filtration and dried in a vacuum oven, affording 1.1 g (crude) of ethyl 4-hydroxy-2,3-bis(4-methoxyphenyl)quinoline-6-carboxylate as a brown solid.
LC-MS (ES, m/z): 430 [M+H]+

Step 2. Ethyl 4-chloro-2,3-bis(4-methoxyphenyl) quinoline-6-carboxylate

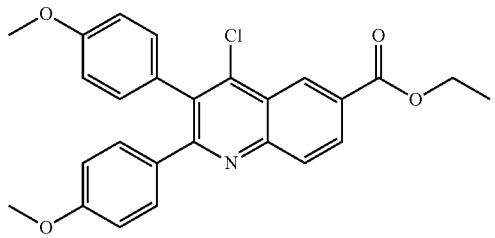 [SMILES: CCOC(=O)c1ccc2nc(-c3ccc(OC)cc3)c(-c3ccc(OC)cc3)c(Cl)c2c1]

A solution of ethyl 4-hydroxy-2,3-bis(4-methoxyphenyl) quinoline-6-carboxylate (1 g, 2.33 mmol, 1.00 equiv) in $POCl_3$ (10 mL) was heated to reflux for 4 h in an oil bath. The resulting mixture was concentrated under vacuum, then diluted with 30 mL of ethyl acetate, and washed with 1×50 mL of sodium bicarbonate (aq.). The organic layer was concentrated under vacuum and purified by column chromatography (ethyl acetate/petroleum ether (1:10)) yielding 0.8 g (77%) of ethyl 4-chloro-2,3-bis(4-methoxyphenyl)quinoline-6-carboxylate as a yellow solid.
LC-MS: (ES, m/z): 448 [M+H]+

Step 3. Ethyl 2,3-bis(4-methoxyphenyl)quinoline-6-carboxylate

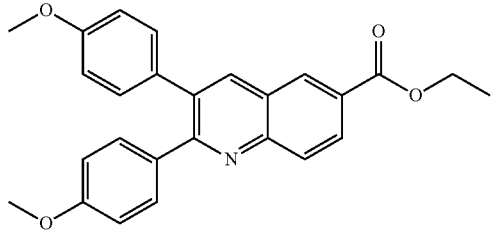 [SMILES: CCOC(=O)c1ccc2nc(-c3ccc(OC)cc3)c(-c3ccc(OC)cc3)cc2c1]

A suspension of ethyl 4-chloro-2,3-bis(4-methoxyphenyl) quinoline-6-carboxylate (150 mg, 0.33 mmol, 1.00 equiv), acetic acid (10 mL), $NH_4OAc$ (102 mg, 1.67 mmol, 5.00 equiv), and palladium on carbon (150 mg) were placed in a 25-mL round-bottom flask and stirred overnight at 40° C. in an oil bath under an atmosphere of $H_2(g)$. The resulting mixture was concentrated, then diluted with 30 ml of ethyl acetate and washed with 10 ml of $NaHCO_3$ (aq.). The organic layer was concentrated in vacuo and purified via silica gel chromatography (PE:EA=30:1) affording 100 mg of ethyl 2,3-bis(4-methoxyphenyl)quinoline-6-carboxylate as yellow solid.
LC-MS-PH-BioE-1163-3: (ES, m/z): 414 [M+H]+

Step 4. 2,3-Bis(4-methoxyphenyl)quinoline-6-carboxylic acid

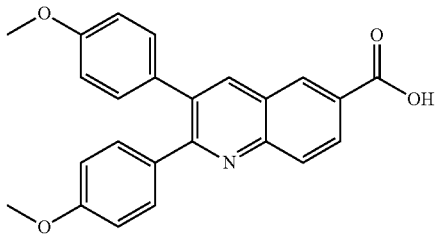 [SMILES: COc1ccc(-c2cc3cc(C(=O)O)ccc3nc2-c2ccc(OC)cc2)cc1]

A solution of ethyl 2,3-bis(4-methoxyphenyl)quinoline-6-carboxylate (83 mg, 0.20 mmol, 1.00 equiv) and sodium hydroxide (40 mg, 1.00 mmol, 5.00 equiv) in methanol (10 mL) and water (1 mL) were placed in a 25-mL round-bottom flask and stirred for 3 h at 50° C. in an oil bath. The resulting mixture was concentrated under vacuum, diluted with 10 mL of $H_2O$, and the pH adjusted to 4-5 with 1N HCl. The resulting solids were collected by filtration and dried in an oven under reduced pressure. The crude product (80 mg) was purified by Flash-Prep-HPLC ($CH_3CN/H_2O$; Detector, UV 254 nm), affording 60 mg (78%) of 2,3-bis(4-methoxyphenyl)quinoline-6-carboxylic acid as a yellow solid.
LC-MS (ES, m/z): 386 [M+H]+
1H-NMR (300 MHz, DMSO, ppm): δ 8.703-8.699 (s, 1H), 8.495 (s, 1H), 8.218-8.183 (d, J=10.5 Hz, 1H), 8.110-8.080 (d, J=9 Hz, 1H), 7.398-7.369 (d, J=8.7 Hz, 2H), 7.234-7.205 (d, J=8.7 Hz, 2H), 6.954-6.871 (m, 4H), 3.776-3.766 (s, 6H)

The activity of the compounds in Examples 1-61 as PASK modulators is illustrated in the following assays. The other compounds listed above, which have not yet been made and/or tested, are predicted to have activity in these assays as well.

Biochemical Assay for hPASK Activity

The assay for purified hPASK activity utilizes the Kinase-Glo Luminescent Kinase Assay (Promega), which quantifies the amount of ATP remaining in solution following kinase reaction. The assay is carried out in a 96-well plate format and is performed by adding a volume of Kinase-Glo Reagent (Promega, catalog #V3771) equal to the volume of solution in the well of a completed kinase reaction. Kinase-Glo reagent contains Luciferase and its substrate. After addition to a kinase reaction it allows to measure luminescence. The amount of ATP left in solution at the time of Kinase-Glo Plus addition is directly proportional to the luminescence that is measured in each well, and inversely correlated with kinase activity.

Purified hPASK from insect cells (0.02 μg) is added to a 50 μL reaction mix containing 40 mM Hepes (pH 7.0), 100 mM KCl, 5 mM MgCl2, 1 mM DTT and 1 ug of MBP protein. Inhibitory compounds are then added and the mixture is incubated for 10 min at 25° C. before adding 5 μL of ATP (at desired concentration). The reaction is allowed to proceed at 25° C. for 1 hour before adding 50 μL of Kinase-Glo reagent.

The luminescence is measured as soon as 10 minutes after Kinase-Glo reagent is added. Results are shown below in Table 1.

| Example # | Full Length $IC_{50}$<br>+ indicates ≤10 μM<br>− indicates ≥10 μM | $IC_{50}$ Kinase Domain<br>+ indicates ≤10 μM<br>− indicates ≥10 μM |
|---|---|---|
| 1 | + | + |
| 2 | + | + |
| 3 | − | − |
| 4 | − | − |
| 5 | + | − |
| 7 | + | − |
| 8 | + | + |
| 9 | + | + |
| 10 | + | + |
| 11 | − | − |

| Example # | $IC_{50}$ Kinase Domain<br>+ indicates ≤10 μM<br>− indicates ≥10 μM |
|---|---|
| 33 | + |
| 50 | + |
| 51 | + |
| 52 | + |
| 53 | + |
| 54 | − |
| 55 | + |
| 56 | − |
| 58 | + |
| 59 | + |

Purified PASK (UniProt #Q96RG2; human recombinant N-terminal GST tagged construct, residues 879-1323) from insect cells (final concentration 5 nM) is added to freshly prepared Base Reaction Buffer containing 20 mM Hepes (pH 7.5), 10 mM MgCl2, 1 mM EGTA, 0.02% Brij35, 0.02 mg/ml BSA, 0.1 mM $Na_3VO_4$, 2 mM DTT, 1% DMSO and Myelin Basic Protein (20 μM final). Test compounds in DMSO are then added and the mixture, followed by delivery of $^{33}$P-ATP (specific activity 0.01 μCi/μl final) to initiate the reaction. The kinase reaction is incubated for 120 min at room temperature. The entire reaction mixture is washed through onto a P81 Phosphocellulose paper and washed three times for 10 minutes in 75 mM phosphoric acid and once in methanol prior to drying and scintillation counting. When the assay was repeated for a given compound, the activity data is based on the average of all trials. Results are shown below in Table 2.

| Example # | $IC_{50}$ Kinase Domain<br>+ indicates ≤10 μM<br>− indicates ≥10 μM |
|---|---|
| 12 | + |
| 13 | + |
| 14 | − |
| 15 | + |
| 16 | + |
| 17 | + |
| 18 | + |
| 19 | + |
| 20 | + |
| 21 | + |
| 22 | + |
| 23 | + |
| 24 | − |
| 25 | + |
| 26 | − |
| 27 | + |
| 28 | + |
| 29 | − |
| 30 | + |
| 31 | + |
| 32 | + |
| 33 | + |
| 34 | + |
| 35 | − |
| 36 | + |
| 37 | + |
| 38 | + |
| 39 | + |
| 40 | + |
| 41 | + |
| 42 | + |
| 43 | + |
| 44 | + |
| 45 | + |
| 46 | + |
| 47 | + |
| 48 | − |

The aim of the FRET assay is to determine the inhibition potential of test compounds on targeted kinase. This assay platform provides a homogenous screening method for measuring kinase activity by quantitating the amount of phospho-substrate in solution following a kinase reaction.

In the presence of kinase and ATP, the Ulight-peptide is phosphorylated and captured by an anti-phospho-substrate antibody, which brings the Eu chelate donor and Ulight acceptor dyes into close proximity. Upon excitation at 340 nm, the Eu chelate transfers its energy to the Ulight dye, resulting in a fluorescent light emission at 665 nm.

Titration of Kinase at 1 mM ATP was achieved via the following protocol. After making serial three-fold dilutions of PASK (Invitrogen) in reaction buffer across the plate; 5 μl of kinase dilution and 5 μl substrate/ATP mix were added to the wells of the white Optiplate-384 (PerkinElmer). The contents of the plate were and incubated at RT for 1 h. The reaction was stopped by adding 5 μl of stop solution to each test well followed by mixing and incubation at RT for 10 minutes. 5 μl of detection mix (detection antibody diluted in detection buffer) was added; the contents of the plate were mixed and then incubated in the dark for 1 hour at RT. The signal was recorded at TR-FRET mode (665 nm/615 nm). The results were graphed to calculate the $EC_{50}$.

Titration of ATP at the $EC_{50}$ Concentration of Kinase to determine ATP Km,app. was performed using the following method. After making serial dilutions of ATP (Invitrogen), 5 μl of ATP dilution and 5 μl substrate/kinase mix were added to the wells of the white Optiplate-384 (PerkinElmer). The contents of the plate were and incubated at RT for 1 h. The reaction was stopped by adding 5 μl of stop solution to each test well followed by mixing and incubation at RT for 10 minutes. 5 μl of detection mix (detection antibody diluted in detection buffer) was added; the contents of the plate were mixed and then incubated in the dark for 1 hour at RT. The signal was recorded at TR-FRET mode (665 nm/615 nm). The results were graphed to calculate the $EC_{50}$ as the ATP Km,app.

Compound screening was done via the following method. 10 mM stock solution of test compound in DMSO was prepared by dissolving test compound in DMSO at RT for 1 hour, and then sonicating at 100% output for 8 minutes. If compound is not soluble under this condition, it was diluted to 3 mM. Kinase reaction buffer was prepared containing 10 mM $MgCl_2$, 50 mM HEPES, 1 mM EGTA, 0.01% TWEEN-20, 2 mM DTT. Serial dilutions of the test compounds were prepared at 4× final assay concentrations using Freedom EVO200® dispensing system as follows: $12 \times 10^{-5}$M, $4 \times 10^{-5}$ M, $1.33 \times 10^{-5}$ M, $4.44 \times 10^{-6}$ 141, $1.48 \times 1.0^{-6}$ M, $4.92 \times 10^{-7}$M, $1.65 \times 10^{-7}$ M. $5.48 \times 10^{-7}$ M, $1.82 \times 10'$M, $6.09 \times 10^{-9}$, $2.03 \times 10^{-9}$ M. Test compounds (2.5 μl at 4× the final assay concentration) was added to wells using Freedom EVO200® dispensing system. As a positive control, 2.5 μl of positive compound was added to assay wells, and 2.5 μl of DMSO to assay wells as vehicle control. Kinase solution was prepared in reaction buffer at 2× final assay concentration. Kinase solution (5 μl) was added to each well of the assay plate. The substrate and ATP solution was prepared in kinase reaction buffer at 4× final assay concentration. The kinase reaction was started by adding 2.5 μl of substrate ATP mix solution to each well of the assay plate. The plate is mixed on a plate shaker; then covered and allowed to react for 2 hours in the dark at 25° C. without shaking. The reaction was stopped by adding 5 μl of stop solution to each test well followed by mixing and incubation at RT for 10 minutes in the dark. 5 μl of detection mix (detection antibody diluted in detection buffer) was added; the contents of the plate were mixed and then incubated in the dark for 1 hour at RT. The signal was recorded at TR-FRET mode (665 nm/615 nm).

| Example # | $IC_{50}$ Kinase Domain<br>+ indicates ≤10 μm<br>− indicates >10 μm |
|---|---|
| 33 | + |
| 52 | + |
| 60 | + |
| 61 | + |

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A method of inhibiting PASK comprising contacting PASK with a compound having structural Formula IIa

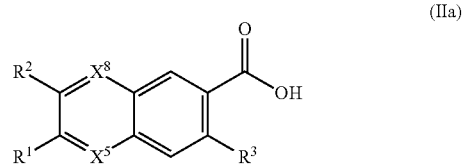

(IIa)

or a pharmaceutically acceptable salt, or ester thereof, wherein:
 $X^5$ and $X^8$ are N;
 $R^1$ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, hetearylalkyl, CN, alkoxy, alkylamino, dialkylamino, hydroxyalkyl, nitro, COOH, $NR^6SO_2R^4$, $NHSO_2NHR^4$, $NHCOR^4$, $NHCONHR^4$, $CONHR^4$, $CONR^{4a}R^{4b}$, hydroxy, $OCF_3$;
 $R^2$ is chosen from alkyl, aryl and heteroaryl, any of which may be optionally substituted with one or more substituents chosen from hydrogen, halo, alkyl, alkenyl, alkynyl, cycloalkyl, haloalkyl, aryl, aralkyl, heterocyclyl, heteroaryl, hetearylalkyl, CN, alkoxy, alkylamino, dialkylamino, hydroxyalkyl, nitro, COOH, $NR^6SO_2R^5$, $NHSO_2NHR^5$, $NHCOR^5$, $NHCONHR^5$, $CONHR^5$, $CONR^{5a}R^{5b}$, hydroxy, $OCF_3$;
 $R^3$ is chosen from hydrogen, hydroxyl, $C_1$-$C_5$ alkyl, and $C_1$-$C_5$ alkoxy;
 $R^4$, $R^{4a}$ and $R^{4b}$ are independently chosen from $C_1$-$C_6$ alkyl, aryl, heteroaryl, aralkyl and heteroaralkyl, any of which may be optionally substituted;
 $R^5$, $R^{5a}$, and $R^{5b}$ are independently chosen from $C_1$-$C_6$ alkyl, aryl, heteroaryl, aralkyl and heteroaralkyl, any of which may be optionally substituted; and
 $R^6$ is chosen from hydrogen and $C_1$-$C_5$ alkyl.

* * * * *